(12) United States Patent
Tsangaris et al.

(10) Patent No.: US 8,128,728 B2
(45) Date of Patent: Mar. 6, 2012

(54) GAS HOMOGENIZATION SYSTEM

(75) Inventors: Andreas Tsangaris, Ottawa (CA); Margaret Swain, Ottawa (CA)

(73) Assignee: Plasco Energy Group, Inc., Kanata, Ontario (CA)

( * ) Notice: Subject to any disclaimer, the term of this patent is extended or adjusted under 35 U.S.C. 154(b) by 454 days.

(21) Appl. No.: 11/745,400

(22) Filed: May 7, 2007

(65) Prior Publication Data

US 2007/0266632 A1    Nov. 22, 2007

Related U.S. Application Data

(60) Provisional application No. 60/798,223, filed on May 5, 2006, provisional application No. 60/864,116, filed on Nov. 2, 2006, provisional application No. 60/911,179, filed on Apr. 11, 2007, provisional application No. 60/797,973, filed on May 5, 2006.

(30) Foreign Application Priority Data

Jun. 5, 2006    (WO) ................ PCT/CA2006/000881

(51) Int. Cl.
   *B01D 50/00*    (2006.01)
(52) U.S. Cl. ........... 95/8; 48/128; 48/174; 95/10; 95/14; 95/15; 95/19; 95/23; 95/287; 96/417; 96/420; 96/421; 96/422; 55/482; 55/482.1
(58) Field of Classification Search ............ 55/DIG. 34, 55/315.1, 385.1; 96/417, 420, 421, 422, 96/423, 108, 111, 112, 113, 109; 48/197 R, 48/202, 209, 210; 110/250, 216, 238, 346; 201/19; 252/373; 373/22, 24; 95/56, 90, 95/107, 8, 10, 12, 14, 15, 17, 19, 22, 23, 95/273; 137/2, 835, 88; 366/151.1
See application file for complete search history.

(56) References Cited

U.S. PATENT DOCUMENTS 4,141,694 A    2/1979    Camacho
(Continued)

FOREIGN PATENT DOCUMENTS

CA    2106746 C    3/1994
(Continued)

OTHER PUBLICATIONS

Presentation to the Hera Group, presented by Alisdair McLean of Plasco Energy Group, "Plasma Gasification of MSW" (Nov. 28, 2006), online: <http://www.conama8.org/modulodocumentos/documentos/SDs/SD32/SD32_ppt_AlisdairMclean.pdf>.

(Continued)

*Primary Examiner* — Duane Smith
*Assistant Examiner* — Minh-Chau Pham
(74) *Attorney, Agent, or Firm* — Christopher & Weisberg, P.A.

(57) ABSTRACT

A system and process for gas homogenization is disclosed. This has application in the areas of generation of gas and its conversion to electricity in downstream applications. The homogenization system minimizes variance in the gas characteristics (composition, flow, pressure, temperature), thereby rendering a steady stream of gas of consistent quality to the downstream machinery. This homogenization system can be adjusted to optimize the output gas stream for specific end-applications, or to optimize the output gas stream for different input feedstocks. This ensures that overall conversion efficiencies are maximized while keeping the process cost-effective. Such a uniform, steady output gas stream has a wide range of applications in the broad areas of generation of electricity (e.g. using internal combustion engines and combustion turbine engines), chemical synthesis (e.g. of compounds such as ethanol, methanol, hydrogen, methane, carbon monoxide, hydrocarbons), fuel-cell technologies and in polygeneration processes (processes that result in co-production of electricity and synthetic fuels).

9 Claims, 32 Drawing Sheets

U.S. PATENT DOCUMENTS

| | | | |
|---|---|---|---|
| 4,181,504 A | 1/1980 | Camacho | |
| 4,208,191 A | 6/1980 | Sze | |
| 4,272,255 A | 6/1981 | Coates | |
| 4,410,336 A | 10/1983 | Blaskowski | |
| 4,472,172 A | 9/1984 | Sheer et al. | |
| 4,606,799 A | 8/1986 | Pirklbauer et al. | |
| 4,696,679 A * | 9/1987 | Albulescu et al. | 48/203 |
| 5,280,757 A | 1/1994 | Carter et al. | |
| 5,331,906 A | 7/1994 | Sonoda et al. | |
| 5,486,269 A | 1/1996 | Nilsson | |
| 5,666,891 A | 9/1997 | Titus et al. | |
| 5,756,957 A | 5/1998 | Titus et al. | |
| 5,785,923 A | 7/1998 | Surma et al. | |
| 5,798,497 A | 8/1998 | Titus et al. | |
| 5,865,206 A | 2/1999 | Steigman et al. | |
| 6,155,182 A | 12/2000 | Tsangaris et al. | |
| 6,200,430 B1 | 3/2001 | Robert | |
| 6,215,678 B1 | 4/2001 | Titus et al. | |
| 6,380,507 B1 | 4/2002 | Childs | |
| 6,394,042 B1 | 5/2002 | West | |
| 6,398,921 B1 | 6/2002 | Moraski | |
| 6,630,113 B1 | 10/2003 | Surma | |
| 6,686,556 B2 | 2/2004 | Mitchell | |
| 6,810,821 B2 | 11/2004 | Chan | |
| 6,817,388 B2 | 11/2004 | Tsangaris et al. | |
| 6,863,268 B2 | 3/2005 | Zhang | |
| 6,887,284 B2 | 5/2005 | Hudson | |
| 2002/0144981 A1 | 10/2002 | Mitchell | |
| 2003/0192609 A1 | 10/2003 | Enerson | |
| 2004/0251241 A1 | 12/2004 | Blutke et al. | |
| 2007/0258869 A1 | 11/2007 | Tsangaris et al. | |
| 2007/0266633 A1 | 11/2007 | Tsangaris et al. | |
| 2007/0266634 A1 | 11/2007 | Tsangaris et al. | |
| 2007/0284453 A1 | 12/2007 | Tsangaris et al. | |
| 2007/0289216 A1 | 12/2007 | Tsangaris et al. | |
| 2008/0104887 A1 | 5/2008 | Tsangaris et al. | |
| 2008/0147241 A1 | 6/2008 | Tsangaris et al. | |
| 2008/0202028 A1 | 8/2008 | Tsangaris et al. | |
| 2008/0209807 A1 | 9/2008 | Tsangaris et al. | |
| 2008/0210088 A1* | 9/2008 | Pledger | 95/56 |
| 2008/0210089 A1* | 9/2008 | Tsangaris et al. | 95/90 |
| 2008/0222956 A1 | 9/2008 | Tsangaris et al. | |
| 2008/0277265 A1 | 11/2008 | Tsangaris et al. | |
| 2009/0020456 A1 | 1/2009 | Tsangaris et al. | |
| 2010/0154304 A1 | 6/2010 | Tsangaris et al. | |
| 2010/0275781 A1 | 11/2010 | Tsangaris et al. | |
| 2011/0036014 A1 | 2/2011 | Tsangaris et al. | |
| 2011/0062013 A1 | 3/2011 | Tsangaris et al. | |
| 2011/0078952 A1 | 4/2011 | Tsangaris et al. | |

FOREIGN PATENT DOCUMENTS

| | | |
|---|---|---|
| CA | 2343035 A1 | 3/2000 |
| CA | 2349608 A1 | 5/2000 |
| CA | 2332685 A1 | 9/2001 |
| CA | 2457075 A1 | 2/2003 |
| CA | 2407102 A1 | 4/2003 |
| CA | 2484472 A1 | 11/2003 |
| CA | 2424805 A1 | 10/2004 |
| CA | 2501841 A1 | 9/2005 |
| CA | 2559875 A1 | 10/2005 |
| CA | 2610806 A1 | 12/2006 |
| CA | 2610808 A1 | 12/2006 |
| CA | 2714911 A1 | 1/2008 |
| CA | 2716912 A1 | 9/2008 |
| CN | 1258712 A | 7/2000 |
| CN | 1382202 A | 11/2002 |
| CN | 1644661 A | 7/2005 |
| DE | 19652770 A1 | 6/1998 |
| DE | 19916931 A1 | 10/2000 |
| DE | 10047787 A1 | 3/2002 |
| EP | 0045256 A2 | 2/1982 |
| EP | 0153235 A1 | 8/1985 |
| EP | 0330872 A2 | 9/1989 |
| EP | 0412587 A1 | 2/1991 |
| EP | 0625869 A2 | 11/1994 |
| EP | 0675324 A1 | 10/1995 |
| EP | 0837041 A1 | 4/1998 |
| EP | 1004746 A1 | 5/2000 |
| EP | 1136542 A1 | 9/2001 |
| EP | 1227141 A2 | 7/2002 |
| EP | 1475429 A1 | 11/2004 |
| EP | 1696177 A1 | 8/2006 |
| FR | 2709980 A1 | 3/1995 |
| GB | 191300500 | 10/1913 |
| GB | 683647 | 12/1952 |
| GB | 2422602 A | 8/2006 |
| JP | 4952465 A | 5/1974 |
| JP | 2122109 A | 5/1990 |
| JP | 566004 A | 3/1993 |
| JP | 571717 A | 3/1993 |
| JP | 933028 A | 2/1997 |
| JP | 9101399 A | 4/1997 |
| JP | 102539 A | 1/1998 |
| JP | 10132230 A | 5/1998 |
| JP | 11515086 A | 12/1999 |
| JP | 2001158887 A | 6/2001 |
| JP | 2003260454 A | 9/2003 |
| KR | 1020050025290 A | 3/2005 |
| NL | 8200417 A | 9/1983 |
| RU | 2125082 C1 | 1/1999 |
| WO | 9404631 A1 | 3/1994 |
| WO | 0181828 A1 | 11/2001 |
| WO | 02096576 A1 | 12/2002 |
| WO | 03018467 A2 | 3/2003 |
| WO | 03018721 A1 | 3/2003 |
| WO | 2004041974 A1 | 5/2004 |
| WO | 2004072207 A1 | 8/2004 |
| WO | 2004072210 A1 | 8/2004 |
| WO | 2004087840 A1 | 10/2004 |
| WO | 2005047435 A2 | 5/2005 |
| WO | 2005118750 A1 | 12/2005 |
| WO | 2006081661 A1 | 8/2006 |
| WO | 2006128285 A1 | 12/2006 |
| WO | 2006128286 A1 | 12/2006 |
| WO | 2009009891 A1 | 1/2009 |

OTHER PUBLICATIONS

Presentation to the Ottawa Centre of Research and Innovation (OCRI), presented by Rod Bryden of the Plasco Energy Group, "A Leap Forward" (Oct. 26, 2006).

Meeting of the Environmental Advisory Committee, City of Ottawa Committee Meeting Minutes, Doc. Minutes 27, (Ottawa: May 11, 2006), online: <http://www.ottawa.ca/ calendar/ottawa/citycouncil/a-eac/2006/05-11/minutes27.htm>.

Joint Meeting of Corporate Services and Economic Development Committee and Planning and Environment Committee, Evaluation Project—Plasma Waste Conversion, Doc. ACS2005-CMR-OCM-0012, (Ottawa: Sep. 7, 2005), online:<http://ottawa.ca/calendar/ottawa/citycouncil /occ/2005/09-28/csedc/ACS2005-CMR-OCM-0012>.

Plasco Energy Group, "Plasco Energy" (Apr. 2, 2006), online: Plasco Energy Group <http://web.archive.org/web/20060412190747/www.plascoenergygroup.com/>.

Ontario, Ministry of the Environment, Certificate of Approval—Air, No. 6925-6REN9E (Dec. 1, 2006).

Ontario, Ministry of the Environment, Provisional Certificate of Approval—Waste Disposal Site, No. 3166-6TYMDZ (Dec. 1, 2006).

European Search Report and Written Opinion dated Sep. 15, 2010 for European Application No. EP07797357, Filing Date May 7, 2007 (15 pages).

Dighe, Dr. Shyam "Westinghouse Plasma Coal Gasification & Vitrification Technology" Presentation to Electric Power Generation Association, Oct. 16-17, 2002. Hershey, PA.

Kerr, R et al., "The Long Lake Project—The First Field Integration of SAGD and Upgrading", SPE International Thermal Operations and Heavy Oil Symposium and International Horizontal Well Technology Conference, Nov. 4-7, 2002, Calgary, Alberta, Canada, Nov. 7, 2002 Retrieved from the Internet: www.longlake.ca/project/bitumen.html.

Klein, "Gasification: An Alternative Process for Energy Recovery and Disposal of Municipal Solid Wastes" May 2002, pp. 1-50.

Physical Chemistry, 2nd edition; Alberty et al. John Wiley & Sons, Inc.; Chapter 5, pp. 131-168; 1996.

Physical Chemistry, 2nd edition; Alberty et al. John Wiley & Sons, Inc.; Chapter 6, pp. 169-218; 1996.

Tsangaris Andreas, U.S. Appl. No. 60/746,632, filed on May 5, 2006, Entitled "Continuous Control System for Regulating the Conversion of a Carbonaceous Feedstock into an Output Gas of Specified Composition", consisting of 72 pages.

* cited by examiner

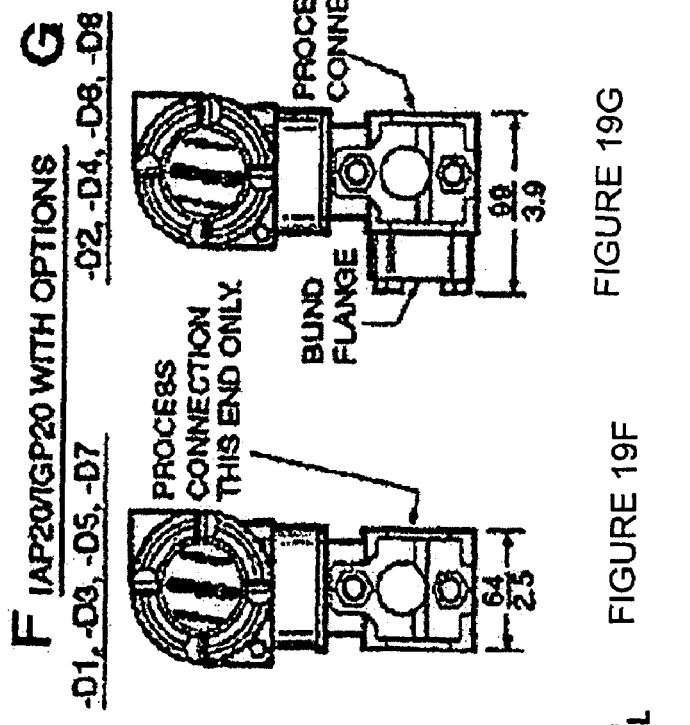
FIGURE 19F
FIGURE 19G
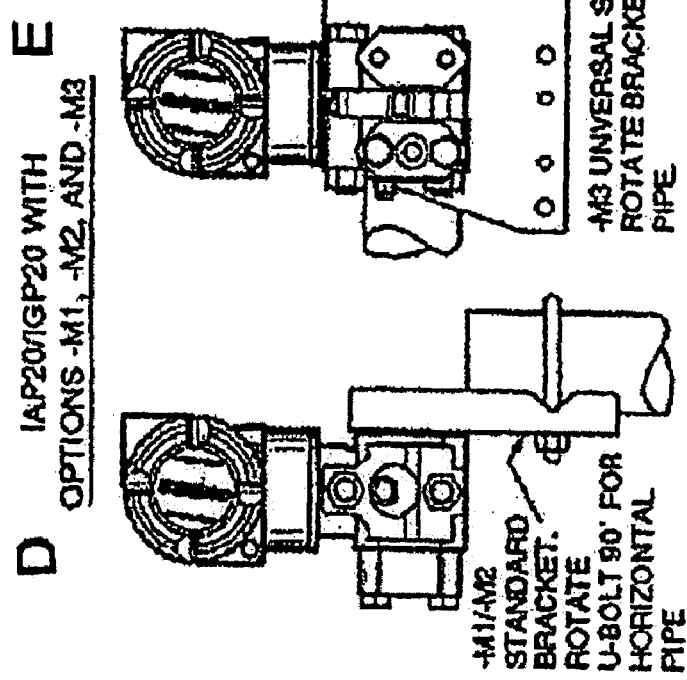
FIGURE 19D
FIGURE 19E

Dual-axial compressor

Single-stage compressor

Two-stage compressor

GAS HOMOGENIZATION SYSTEM

CROSS REFERENCE TO RELATED APPLICATIONS

This application claims benefit of priority under 35 U.S.C. §119(e) from U.S. Provisional Application Ser. No. 60/798,223, filed May 5, 2006. This application also claims benefit of priority to International Patent Application No. PCT/CA2006/000881, filed Jun. 5, 2006. This application also claims benefit of priority under 35 U.S.C. §119(e) from U.S. Provisional Application Ser. No. 60/864,116, filed Nov. 2, 2006. This application also claims benefit of priority under 35 U.S.C. §119(e) from U.S. Provisional Application Ser. No. 60/911,179, filed Apr. 11, 2007. This application also claims benefit of priority under 35 U.S.C. §119(e) from U.S. Provisional Application Ser. No. 60/797,973, filed May 5, 2006. The contents of all of the aforementioned applications are hereby expressly incorporated by reference in their entirety and for all purposes.

FIELD OF THE INVENTION

The invention pertains to the field of gas production and conversion to energy in downstream applications. In particular, the invention relates to a gas homogenization system useful in generating a steady stream of gas of substantially consistent characteristics.

BACKGROUND

Gasification is a process that enables the conversion of carbonaceous feedstock, such as municipal solid waste (MSW) or coal, into a combustible gas. The gas can be used to generate electricity, steam or as a basic raw material to produce chemicals and liquid fuels.

Possible uses for the gas include: the combustion in a boiler for the production of steam for internal processing and/or other external purposes, or for the generation of electricity through a steam turbine; the combustion directly in a gas turbine or a gas engine for the production of electricity; fuel cells; the production of methanol and other liquid fuels; as a further feedstock for the production of chemicals such as plastics and fertilizers; the extraction of both hydrogen and carbon monoxide as discrete industrial fuel gases; and other industrial applications.

Generally, the gasification process consists of feeding carbonaceous feedstock into a heated chamber (the gasifier) along with a controlled and/or limited amount of oxygen and optionally steam. In contrast to incineration or combustion, which operate with excess oxygen to produce $CO_2$, $H_2O$, $SO_x$, and NOx, gasification processes produce a raw gas composition comprising CO, $H_2$, $H_2S$, and $NH_3$. After cleanup, the primary gasification products of interest are $H_2$ and CO.

Useful feedstock can include any municipal waste, waste produced by industrial activity and biomedical waste, sewage, sludge, coal, heavy oils, petroleum coke, heavy refinery residuals, refinery wastes, hydrocarbon contaminated soils, biomass, and agricultural wastes, tires, and other hazardous waste. Depending on the origin of the feedstock, the volatiles may include $H_2O$, $H_2$, $N_2$, $O_2$, $CO_2$, CO, $CH_4$, $H_2S$, $NH_3$, $C_2H_6$, unsaturated hydrocarbons such as acetylenes, olefins, aromatics, tars, hydrocarbon liquids (oils) and char (carbon black and ash).

As the feedstock is heated, water is the first constituent to evolve. As the temperature of the dry feedstock increases, pyrolysis takes place. During pyrolysis the feedstock is thermally decomposed to release tars, phenols, and light volatile hydrocarbon gases while the feedstock is converted to char.

Char comprises the residual solids consisting of organic and inorganic materials. After pyrolysis, the char has a higher concentration of carbon than the dry feedstock and may serve as a source of activated carbon. In gasifiers operating at a high temperature (>1,200° C.) or in systems with a high temperature zone, inorganic mineral matter is fused or vitrified to form a molten glass-like substance called slag. Since the slag is in a fused, vitrified state, it is usually found to be non-hazardous and may be disposed of in a landfill as a non-hazardous material, or sold as an ore, road-bed, or other construction material. It is becoming less desirable to dispose of waste material by incineration because of the extreme waste of fuel in the heating process and the further waste of disposing, as a residual waste, material that can be converted into a useful syngas and solid material.

The means of accomplishing a gasification process vary in many ways, but rely on four key engineering factors: the atmosphere (level of oxygen or air or steam content) in the gasifier; the design of the gasifier; the internal and external heating means; and the operating temperature for the process. Factors that affect the quality of the product gas include: feedstock composition, preparation and particle size; gasifier heating rate; residence time; the plant configuration including whether it employs a dry or slurry feed system, the feedstock-reactant flow geometry, the design of the dry ash or slag mineral removal system; whether it uses a direct or indirect heat generation and transfer method; and the syngas cleanup system. Gasification is usually carried out at a temperature in the range of about 650° C. to 1200° C., either under vacuum, at atmospheric pressure or at pressures up to about 100 atmospheres.

There are a number of systems that have been proposed for capturing heat produced by the gasification process and utilizing such heat to generate electricity, generally known as combined cycle systems.

The energy in the product gas coupled with substantial amounts of recoverable sensible heat produced by the process and throughout the gasification system can generally produce sufficient electricity to drive the process, thereby alleviating the expense of local electricity consumption. The amount of electrical power that is required to gasify a ton of a carbonaceous feedstock depends directly upon the chemical composition of the feedstock.

If the gas generated in the gasification process comprises a wide variety of volatiles, such as the kind of gas that tends to be generated in a low temperature gasifier with a "low quality" carbonaceous feedstock, it is generally referred to as off-gas. If the characteristics of the feedstock and the conditions in the gasifier generate a gas in which CO and $H_2$ are the predominant chemical species, the gas is referred to as syngas. Some gasification facilities employ technologies to convert the raw off-gas or the raw syngas to a more refined gas composition prior to cooling and cleaning through a gas quality conditioning system.

Utilizing plasma heating technology to gasify a material is a technology that has been used commercially for many years. Plasma is a high temperature luminous gas that is at least partially ionized, and is made up of gas atoms, gas ions, and electrons. Plasma can be produced with any gas in this manner. This gives excellent control over chemical reactions in the plasma as the gas might be neutral (for example, argon, helium, neon), reductive (for example, hydrogen, methane, ammonia, carbon monoxide), or oxidative (for example, oxygen, carbon dioxide). In the bulk phase, a plasma is electrically neutral.

Some gasification systems employ plasma heat to drive the gasification process at a high temperature and/or to refine the offgas/syngas by converting, reconstituting, or reforming longer chain volatiles and tars into smaller molecules with or without the addition of other inputs or reactants when gaseous molecules come into contact with the plasma heat, they will disassociate into their constituent atoms. Many of these atoms will react with other input molecules to form new molecules, while others may recombine with themselves. As the temperature of the molecules in contact with the plasma heat decreases all atoms fully recombine. As input gases can be controlled stoichiometrically, output gases can be controlled to, for example, produce substantial levels of carbon monoxide and insubstantial levels of carbon dioxide.

The very high temperatures (3000 to 7000° C.) achievable with plasma heating enable a high temperature gasification process where virtually any input feedstock including waste in as-received condition, including liquids, gases, and solids in any form or combination can be accommodated. The plasma technology can be positioned within a primary gasification chamber to make all the reactions happen simultaneously (high temperature gasification), can be positioned within the system to make them happen sequentially (low temperature gasification with high temperature refinement), or some combination thereof.

The gas produced during the gasification of carbonaceous feedstock is usually very hot but may contain small amounts of unwanted compounds and requires further treatment to convert it into a useable product. Once a carbonaceous material is converted to a gaseous state, undesirable substances such as metals, sulfur compounds and ash may be removed from the gas. For example, dry filtration systems and wet scrubbers are often used to remove particulate matter and acid gases from the gas produced during gasification. A number of gasification systems have been developed which include systems to treat the gas produced during the gasification process.

These factors have been taken into account in the design of various different systems which are described, for example, in U.S. Pat. Nos. 6,686,556, 6,630,113, 6,380,507; 6,215,678, 5,666,891, 5,798,497, 5,756,957, and U.S. Patent Application Nos. 2004/0251241, 2002/0144981. There are also a number of patents relating to different technologies for the gasification of coal for the production of synthesis gases for use in various applications, including U.S. Pat. Nos. 4,141,694; 4,181,504; 4,208,191; 4,410,336; 4,472,172; 4,606,799; 5,331,906; 5,486,269, and 6,200,430.

Prior systems and processes have not adequately addressed the problems that must be dealt with on a continuously changing basis. Some of these types of gasification systems describe means for adjusting the process of generating a useful gas from the gasification reaction. Accordingly, it would be a significant advancement in the art to provide a system that can efficiently gasify carbonaceous feedstock in a manner that maximizes the overall efficiency of the process, and/or the steps comprising the overall process.

As noted above, gas from a gasification system can be exploited for a variety of applications such as the conversion of the gas to energy in the form of electricity or chemical applications such as fuel cells or chemical feedstock. The equipment, which is used to directly convert gas into electricity currently comprises gas turbines and gas engines. These machines are designed to function within a very strict range of characteristics and are often very sensitive to changes in certain gas characteristics. In addition to affecting the efficiency of engine operation, a deviation in the gas characteristics may even have a negative effect on engine operation. For example, changes in the gas characteristics can affect the emissions, efficiency, knock and combustion stability, as well as increase the maintenance requirements of the engine. Accordingly, these gas-utilizing machines work most effectively when the characteristics of the gas are maintained within the specified limits.

The characteristics of the gas produced by a gasification system, such as chemical composition, flow rate, temperature, pressure, and relative humidity will naturally vary over time largely due to variations in the feedstock composition and the reaction conditions that occur, for example, during the gasification process. Some characteristics of the gas will vary on a minute-to-minute basis and some characteristics on a second-to-second basis. A steady stream of gas with consistent characteristics will be produced only if the gas is allowed to mix thoroughly to ensure a homogeneous gas composition and the other characteristics such as temperature, pressure and flow rate are adjusted.

U.S. Pat. No. 6,398,921 describes a gasification process for producing fuel gas for use in internal combustion engines for the generation of electricity. Prior to fueling the engine, the fuel gas is cleaned, compressed, and stored in a tank for limited surge storage. Although the fuel gas is regulated to the inlet pressure required for the engine, the fuel gas is not regulated for other characteristics, namely its composition. Accordingly, there remains a need for a gas homogenization system, which minimizes variance in the gas characteristics (composition, flow rate, pressure, temperature), thereby rendering a steady stream of gas of consistent quality required by downstream machinery.

This background information is provided for the purpose of making known information believed by the applicant to be of possible relevance to the invention. No admission is necessarily intended, nor should be construed, that any of the preceding information constitutes prior art against the invention.

SUMMARY OF THE INVENTION

This invention provides a gas homogenization system for homogenizing the chemical composition of an input gas and adjusting other characteristics such as flow rate, pressure, and temperature of the gas, thereby creating a regulated gas to meet downstream requirements. This system enables a continual and steady stream of gas of defined characteristics to be delivered to downstream applications, for example, a gas turbine, engine or other suitable applications.

In particular, the gas homogenization system of the invention provides a gas homogenization chamber having dimensions that are designed to accommodate a gas residence time sufficient to attain a homogeneous gas of a consistent output composition. Other elements of the gas homogenization system are designed and configured such that the regulated gas meets the performance requirements of a downstream application. The system may also comprise a feedback control system to optimize the energetics and output of the process.

An object of the invention is to provide a gas homogenization system. In accordance with an aspect of the invention, there is provided a gas homogenization system for regulating gas characteristics, comprising: a homogenization chamber comprising a gas inlet and a gas outlet; one or more sensing elements associated with the homogenization chamber for monitoring one or more characteristics of the gas; one or more response elements associated with the homogenization chamber for affecting a change to the one or more characteristics of the gas; and one or more process devices operatively connected to the one or more response elements for adjusting the one or more characteristics of the gas; wherein the homogenization chamber is designed to accommodate a residence time sufficient to enable monitoring and regulation of the one or more gas characteristics.

In accordance with another aspect of the invention, there is provided a gas homogenization system for regulating gas characteristics, comprising: a homogenization chamber comprising a gas inlet and a gas outlet; a gas inlet mechanism in fluid communication with the gas inlet of the homogenization chamber, comprising: one or more inlet conduits, and one or more sensing elements for monitoring of data relating to chemical composition, temperature, flow rate, and pressure parameters of the gas; a regulated gas outlet mechanism in fluid communication with the gas outlet of the homogenization chamber for directing output of stabilized gas to a downstream application, the outlet mechanism comprising one or more outlet conduits; one or more process devices associated with the system to regulate the chemical composition, temperature, flow rate, and pressure parameters of the gas; and one or more response elements operatively associated with the one or more process devices for affecting the system to optimize the chemical composition, temperature, flow rate, and pressure parameters of the gas; wherein the homogenization chamber is designed to accommodate a residence time sufficient to enable monitoring and regulation of the gas composition, temperature, flow rate, and pressure.

In accordance with an aspect of the invention, there is provided a process for converting an input gas to a regulated gas using the gas homogenization system according to the invention, the process comprising the steps of: providing an input gas; monitoring the gas within the system for chemical composition, temperature, flow rate, and pressure by way of the one or more sensing elements; and providing instructions to the one or more response elements for adjusting the one or more process devices to optimize the chemical composition, temperature, flow rate, and/or pressure parameters of the gas thereby producing a regulated gas that satisfies the requirements of the downstream application.

BRIEF DESCRIPTION OF THE FIGURES

These and other features of the invention will become more apparent in the following detailed description in which reference is made to the appended drawings.

FIGS. 19A-K illustrate mounting and bracketing devices for the pressure transmitter, in accordance with embodiments of the invention.

DETAILED DESCRIPTION OF THE INVENTION

Definitions

Figure 1A:
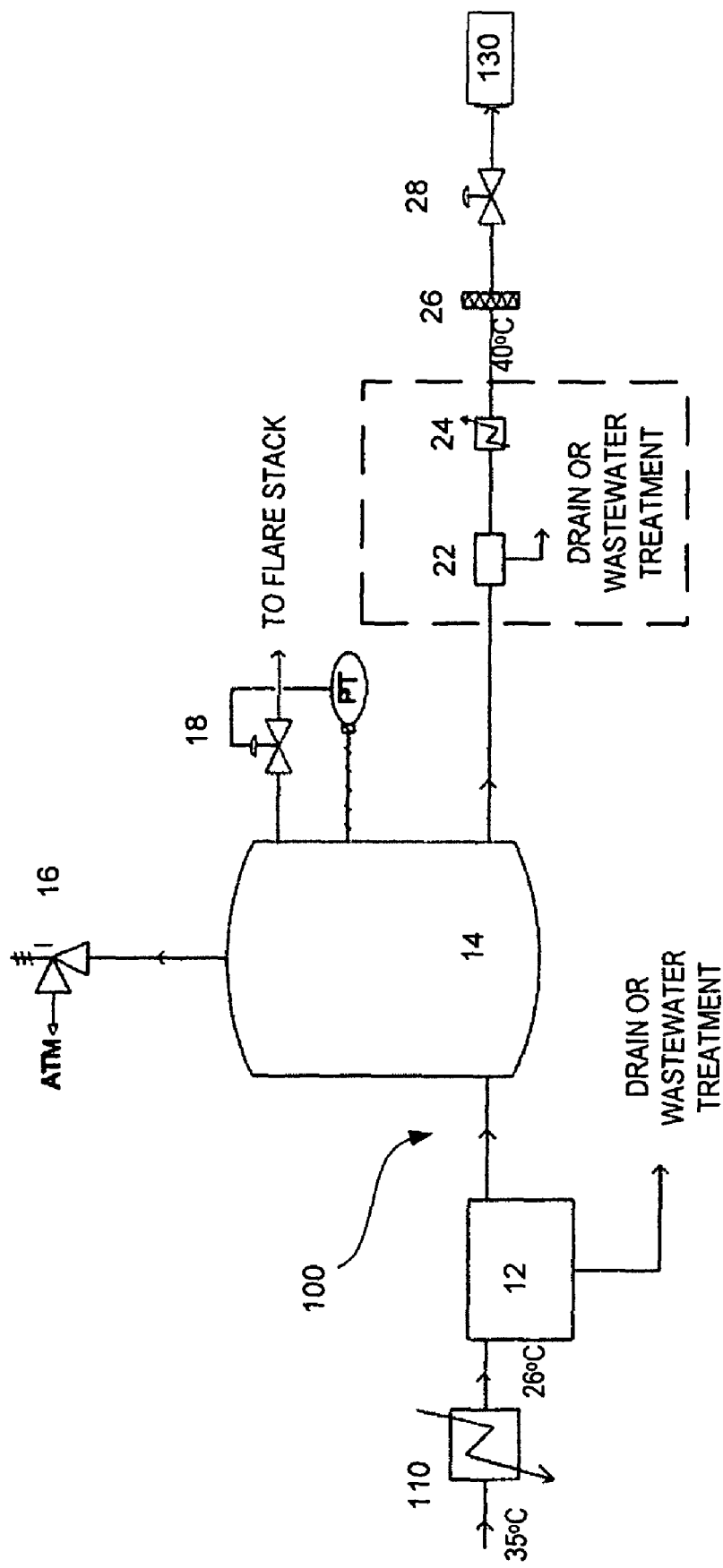
FIG. 1A is an illustration of a gas homogenization system, in accordance with one embodiment of the invention, where gas is delivered from a single source to a single homogenization chamber and then delivered to a single engine by way of a gas conditioning skid.

As used herein, the term "about" refers to approximately a +/−10% variation from the stated value.

The term "composition of the gas," refers to the entire composition of chemical species within a gas. In practice, however, this term will generally be used to express the species and concentrations of the chemical constituents that are most relevant to the downstream applications. For example, gas composition desirable for a gas turbine will generally be described in terms of the amount of nitrogen, carbon monoxide, carbon dioxide, water and/or hydrogen in the synthesis gas. The chemical composition may also be identified as lacking specific chemical species, i.e. species that would be undesirable to transfer to the downstream application, such as a gas being, 'free of $H_2S$." The chemical composition of gas can vary widely, depending on the composition of the feedstock used to generate the gas and the manner in which the gasification process, the gas cleanup and conditioning were carried out. Depending on the context, which will be apparent to one skilled in the art, the composition of the gas will or will not contemplate trace elements.

The term, "characteristics of the gas," refers to the relevant chemical and physical qualities of the gas, including its chemical composition, temperature, pressure, rate of flow etc. Depending upon the context, one skilled in the art can appreciate that it may include color, odor, etc.

LHV means low heating value.

HHV means high heating value

As used herein, the term "sensing element" is defined to describe any element of the system configured to sense a characteristic of a process, a process device, a process input or process output, wherein such characteristic may be represented by a characteristic value useable in monitoring, regulating and/or controlling one or more local, regional and/or global processes of the system. Sensing elements considered within the context of a gasification system may include, but are not limited to, sensors, detectors, monitors, analyzers or any combination thereof for the sensing of process, fluid and/or material temperature, pressure, flow, composition and/or other such characteristics, as well as material position and/or disposition at any given point within the system and any operating characteristic of any process device used within the system. It will be appreciated by the person of ordinary skill in the art that the above examples of sensing elements, though each relevant within the context of a gasification system, may not be specifically relevant within the context of the present disclosure, and as such, elements identified herein as sensing elements should not be limited and/or inappropriately construed in light of these examples.

As used herein, the term "response element" is defined to describe any element of the system configured to respond to a sensed characteristic in order to operate a process device operatively associated therewith in accordance with one or more pre-determined, computed, fixed and/or adjustable control parameters, wherein the one or more control parameters are defined to provide a desired process result. Response elements considered within the context of a gasification system may include, but are not limited to static, preset and/or dynamically variable drivers, power sources, and any other element configurable to impart an action, which may be mechanical, electrical, magnetic, pneumatic, hydraulic or a combination thereof, to a device based on one or more control parameters. Process devices considered within the context of a gasification system, and to which one or more response elements may be operatively coupled, may include, but are not limited to, material and/or feedstock input means, heat sources such as plasma heat sources, additive input means, various gas blowers and/or other such gas circulation devices, various gas flow and/or pressure regulators, and other process devices operable to affect any local, regional and/or global process within a gasification system. It will be appreciated by the person of ordinary skill in the art that the above examples of response elements, though each relevant within the context of a gasification system, may not be specifically relevant within the context of the present disclosure, and as such, elements identified herein as response elements should not be limited and/or inappropriately construed in light of these examples.

Unless defined otherwise, all technical and scientific terms used herein have the same meaning as commonly understood by one of ordinary skill in the art to which this invention belongs.

Overview

The invention provides a homogenization system for homogenizing the chemical composition of a gas and for adjusting other gas characteristics such as flow rate, pressure, and temperature to meet the requirements of downstream applications. The resulting output gas stream called the regulated gas is substantially continual and steady and has substantially well-controlled characteristics suitable for a downstream application.

This invention provides a system comprising one or more chambers of various sizes and shapes wherein the primary objective of the chamber is to homogenize the composition of a gas to attain a consistent output stream of gas, for example, by reducing fluctuations in the concentration of its relevant chemical constituents. The concentration of chemical constituents in the output gas will only vary within the range allowable for the relevant chemical constituents. The shape of the chamber can range from a standard gas storage tank, with fixed or floating roof, down to wide diameter pipe. An important consideration for the homogenization chamber is its volume which will ensure that the gas achieves a critical residence time to enable sufficient homogenization of its chemical constituents. Other considerations include pressure and temperature (especially environmental) requirements.

Downstream applications, such as gas engines and gas turbines, can tolerate only a limited rate of change and limited overall change of gas characteristics, such as gas pressure and the lower heating value (LHV), outside of which the performance, reliability or emissions of the application may be affected. Accordingly, it is advantageous to stabilize the variance as much as possible to optimize application performance. The system of this invention provides the ability to deliver a regulated gas that only varies within the rates and ranges allowed by an application, and does so such that the gas quality is in a range that the system can produce energy in substantially the most cost effective manner possible. Accordingly, in one embodiment, the regulated gas of the invention is gas within which the rate of change of the gas LHV and pressure, and the overall change of LHV and pressure are within the tolerance limits of a downstream application.

Prior to defining the components and process associated with the gas homogenization system, a brief overview of the input gas and regulated gas characteristics are provided below.

Input Gas Characteristics

The composition of the gas, which will enter the homogenization system of the invention, is determined by the gasification process. Adjustments made during the gasification process permit the gas to be optimized for specific end-applications (e.g., gas turbines for electricity generation), or optimized for gas generation from different feedstocks, i.e., different sources of carbon, such as coal or municipal solid waste (MSW). Accordingly, the composition of the gas can be tailored for particular energy generating technologies (for example, for specific gas engines or gas turbines) and, for best overall conversion efficiency, according to the different types of feedstock used, by adjusting the operational parameters of the gasification process.

The gas entering the system may be derived from a gasification system. Examples of suitable input gases include those derived from a gasifier, a gas conditioning system (GCS), a solid residue gas conditioner, and the like. In one embodiment, the input gas is a clean gas derived from a $H_2S$ scrubber, a HCl scrubber or an activated carbon bed.

The gas leaving the gasification system, may be within a defined range of a target composition, however, over time the gas may fluctuate in its characteristics due to variability in the gasification process such as feedstock composition and feed rate, airflow and temperature fluctuations.

Composition and Variances

Typically the main components of the gas as it leaves a gasification system tend to be carbon monoxide, nitrogen, carbon dioxide, hydrogen, and water. Much smaller amounts of methane, ethylene, hydrogen chloride and hydrogen sulfide may also be present.

The exact proportions of the different chemical constituents depend on the type of feedstock used. For example, gas produced from coal (which is generally considered to be a relatively even composition of carbonaceous feedstock compared to municipal solid waste), under a specific set of operating conditions, yields about 26% carbon monoxide, about 11.5% carbon dioxide, about 28% hydrogen and about 31% water vapour. Gasification of sub-bituminous coal (which has a composition suitable for about 23.1 MJ/kg-25.1% moisture content), under another set of operating conditions, yields about 18.2%, about 6.9%, about 17.8% and about 15.1%, carbon monoxide, carbon dioxide, hydrogen and water, respectively. In fact, there are several different types of coal, ranging from peat to lignite (moisture around about 70%, energy content around about 8-10 MJ/kg), to black coal (moisture around about 3% and energy content about 24-28 MJ/kg) to anthracite (virtually no moisture and energy content up to about 32 MJ/kg), that may each exhibit substantial variability in the gas produced therefrom.

Pressure and Temperature

Similar to the control of gas composition, the pressure and temperature of the gas can also be monitored and controlled in the gasification system in order to maintain these parameters within the tolerance limits prescribed by a downstream application. Despite these controls, however, fluctuations in both the pressure and temperature of the gas will typically occur over time. In the case of pressure, fluctuations may occur on a per second basis; and with temperature, on a per minute basis. In one embodiment of the invention, the pressure variance limit is selected to be <than about 0.145 psi/second.

Regulated Gas Characteristics

As noted above, the regulated gas exiting the gas homogenization system of the invention has substantially stabilized characteristics that meet the specifications of a downstream application. Typically, machine manufacturers will provide the requirements and tolerances allowed by specific machinery; such gas parameters for a gas engine or gas turbine would be known to a person skilled in the art. In one embodiment of the invention, a gas engine may require a regulated gas composition LHV to have a maximum of about 1% change in about 30 seconds. In one embodiment of the invention, gas engines can accept gas with HHV as low as about 50 BTU/scf, so long as it contains a minimum of about 12% Hydrogen. In one embodiment of the invention, the regulated gas requires the Wobbe Index (defined as T(degrees R)/sq.rt (specific gravity)) to be +/−4% of the design value for use with turbine engines. In addition, a turbine engine may also require a minimum LHV of about 300 Btu/scf and a minimum pressure of about 475 psig. In one embodiment of the invention, the engine will require a regulated gas temperature greater than or equal to the dew point temperature plus about 20° F. where relative humidity is at a maximum of about 80%.

Gas Homogenization System

As mentioned above, the invention provides a system that collects gas and attenuates fluctuations in the chemistry of the gas composition in a homogenization chamber. Other elements of the system optionally adjust characteristics of the gas such as flow rate, humidity, temperature and pressure to be within ranges that are acceptable to a downstream application. The system thereby regulates the characteristics of the gas to produce a continual stream of gas with substantially consistent characteristics for delivery to a downstream application, such as a gas engine or a gas turbine. The system may also comprise a feedback control system to optimize the energetics and output of the process.

FIG. 1A illustrates a gas homogenization system 100 configured in accordance with one embodiment of the invention for the production of a regulated gas. The gas homogenization system 100 comprises: a chiller 110, a gas/liquid separator 12; a homogenization chamber 14, to which a relief valve 16 and a pressure control valve 18 are connected; a gas conditioning skid 20, comprising a gas/liquid separator 22 and a heater 24; a filter 26; and a pressure regulating valve 28. The regulated gas may subsequently be directed through a suitable conduit to an engine 30.

As indicated by the arrows in FIG. 1A, a gas enters the homogenization system 100 at the chiller 110, where the temperature of the gas is appropriately adjusted. The gas is then delivered to the separator 12, by suitable conduit means, where the humidity of the gas is regulated. Following this, the gas enters the homogenization chamber 14, by way of gas inlet conduit means. Once in the homogenization chamber 14, the gas is mixed or blended, resulting in a gas having a stabilized composition. The gas flow rate and pressure of the mixed or blended gas are further regulated upon exit of the mixed or blended gas from the homogenization chamber.

Suitable conduit means then carry the mixed or blended gas to the gas conditioning skid 20, where regulation of the temperature and humidity of the mixed or blended gas is undertaken. The mixed or blended gas, carried by suitable conduit means, is then filtered 26 and regulated for pressure 28. The resulting regulated gas, now meeting the desired requirements for a downstream application, may be directed through suitable conduit means to the engine 30.

Typically, gas will be conveyed from a gasification process to the homogenization chamber as it is generated. To ensure a uniform input gas flow rate, a draft induction device may also be employed. Similarly, to ensure that factors such as gas composition, flow rate, temperature and pressure of the input gas stream are compliant with the desired range of target characteristics, the input gas may be monitored by a monitoring system, as would be known to the skilled technician, prior to homogenization. Given the outcome of the analysis of these factors, gas may then be directed to the homogenization chamber.

Figure 1B:
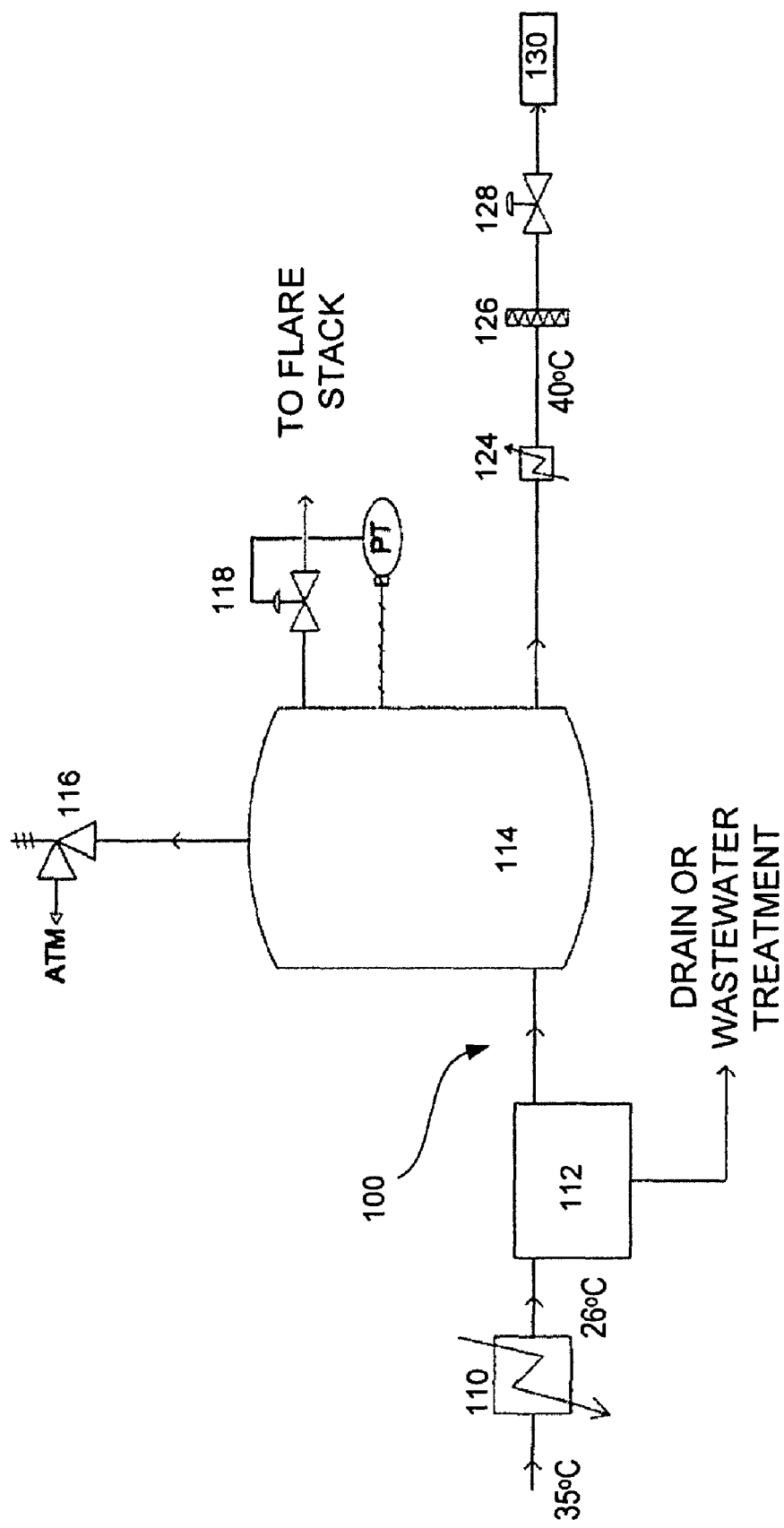
FIG. 1B is an illustration of a gas homogenization system, in accordance with one embodiment of the invention, where gas is delivered from a single source to a single homogenization chamber and then delivered to a single engine by way of a heater, filter and a pressure regulator valve.

FIG. 1B illustrates a gas homogenization system 100, in accordance with one embodiment of the invention which is configured for the production of a regulated gas. The gas homogenization system 100 comprises a chiller 110; a gas/liquid separator 112; a homogenization chamber 114, to which a relief valve 116 and a pressure control valve 118 are connected; a heater 124; a filter 126; and a pressure regulating valve 128. The regulated gas may subsequently be directed through a suitable conduit to an engine 130.

Figure 2:
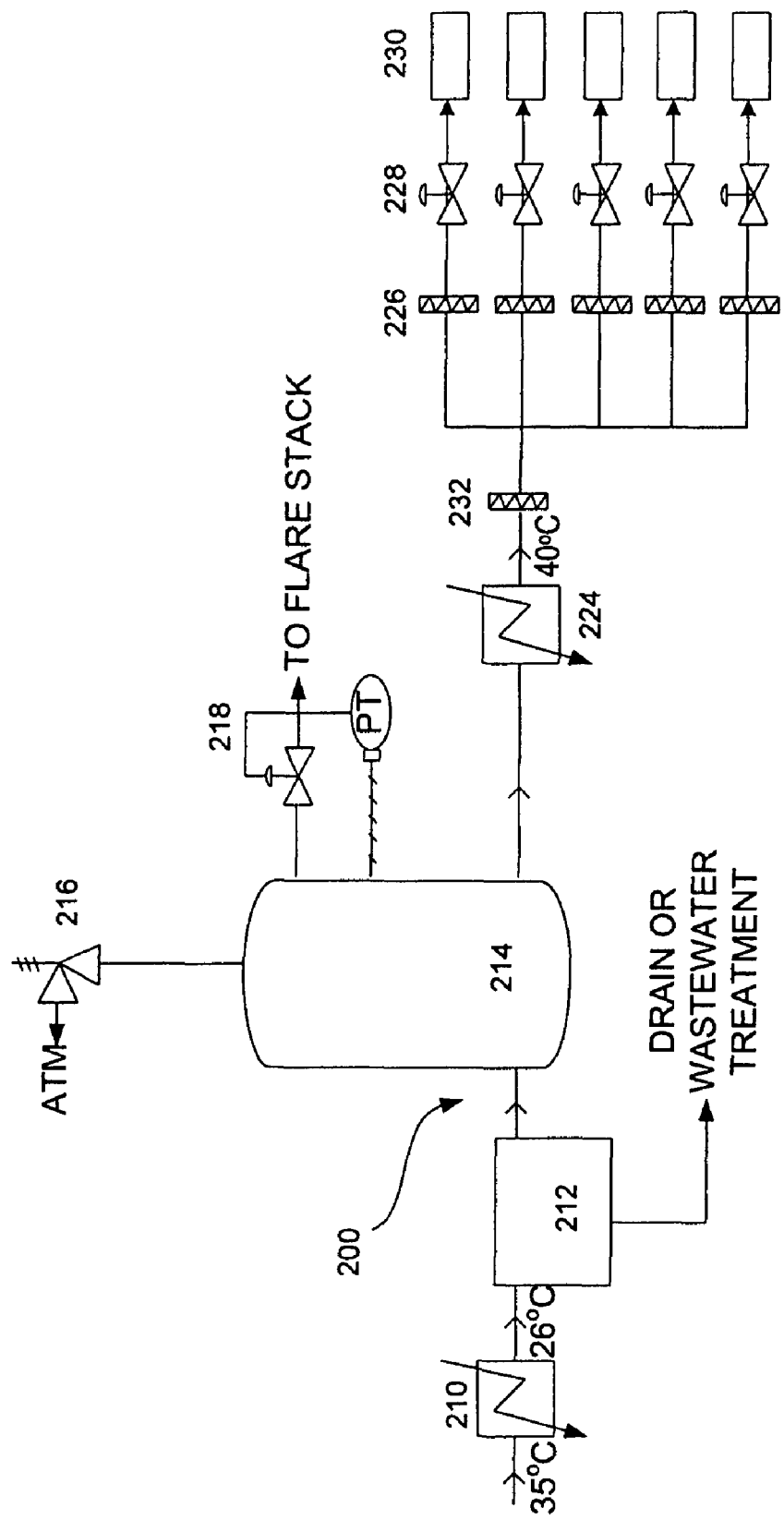
FIG. 2 is an illustration of a gas homogenization system, in accordance with one embodiment of the invention, where gas is delivered from a single source to a single homogenization chamber and then delivered to multiple engines by way of a heater and a plurality of filters and pressure regulator valves.

FIG. 2 illustrates a gas homogenization system 200 configured in accordance with one embodiment of the invention which is configured for the production of a regulated gas. The gas homogenization system 200 comprises: a chiller 210; a gas/liquid separator 212; a homogenization chamber 214, to which a relief valve 216 and a pressure control valve 218 are connected; a heater 224; a filter 232; a series of filters 226; and a series of pressure regulating valves 228. Thus, the gas is derived from a single source and the regulated gas is delivered to a series of engines 230 by way of a single homogenization chamber 214.

Figure 3:
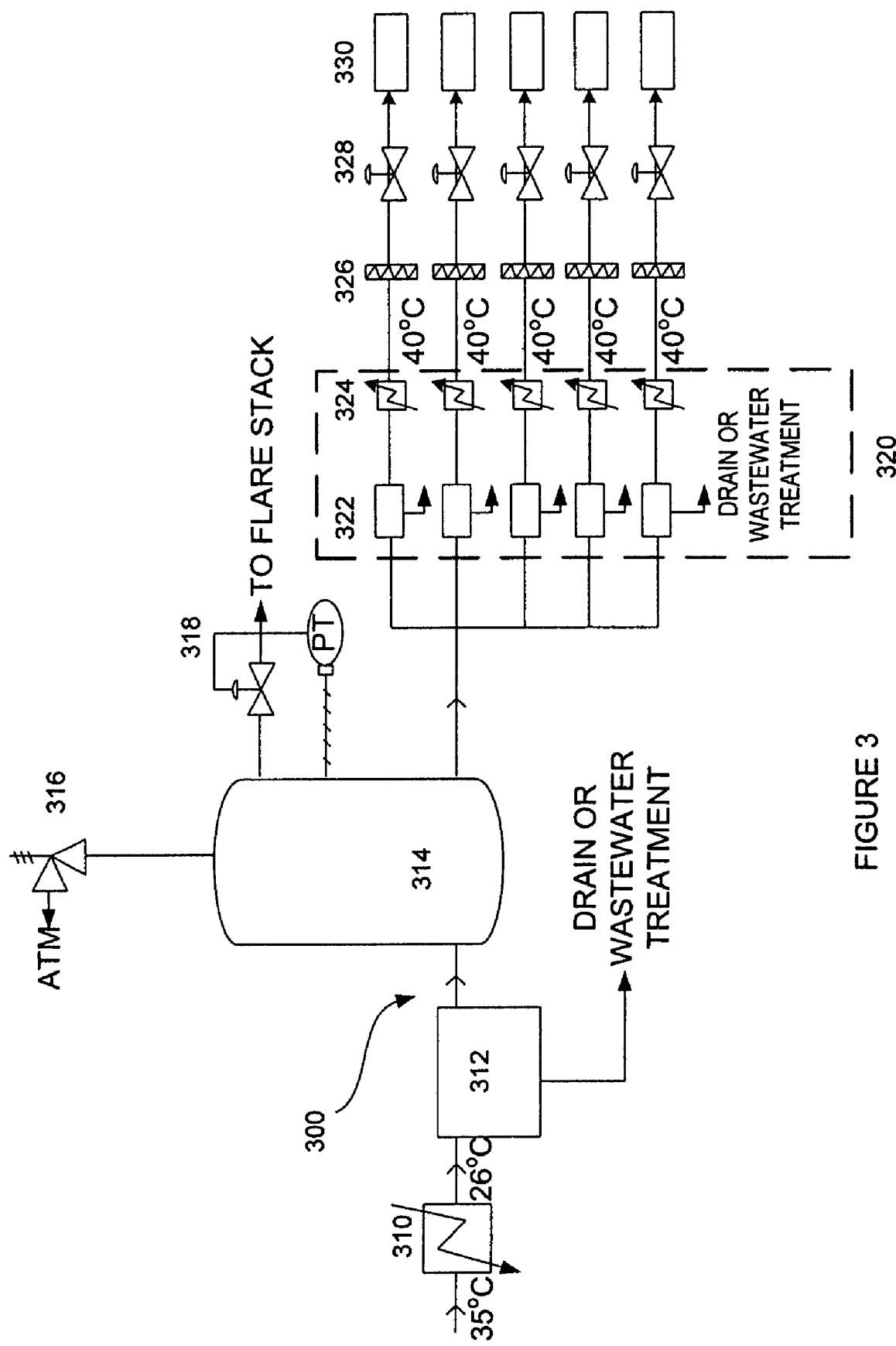
FIG. 3 is an illustration of a gas homogenization system, in accordance with one embodiment of the invention, where gas is delivered from a single source to a single homogenization chamber and then delivered to multiple engines, each engine having its own gas conditioning skid.

FIG. 3 illustrates a gas homogenization system 300 configured in accordance with one embodiment of the invention which is configured for the production of a regulated gas. The gas homogenization system 300 comprises: a chiller 310; a gas/liquid separator 312; a homogenization chamber 314, to which a relief valve 316 and a pressure control valve 318 are connected; a series of gas conditioning skids 320, each skid comprising a gas/liquid separator 322 and a heater 324; a series of filters 326; and a series of pressure regulating valves 328. Thus, the regulated gas is delivered from a single source to a series of engines 330 by way of a single homogenization chamber 314 and a series of gas conditioning skids 320.

Figure 4:
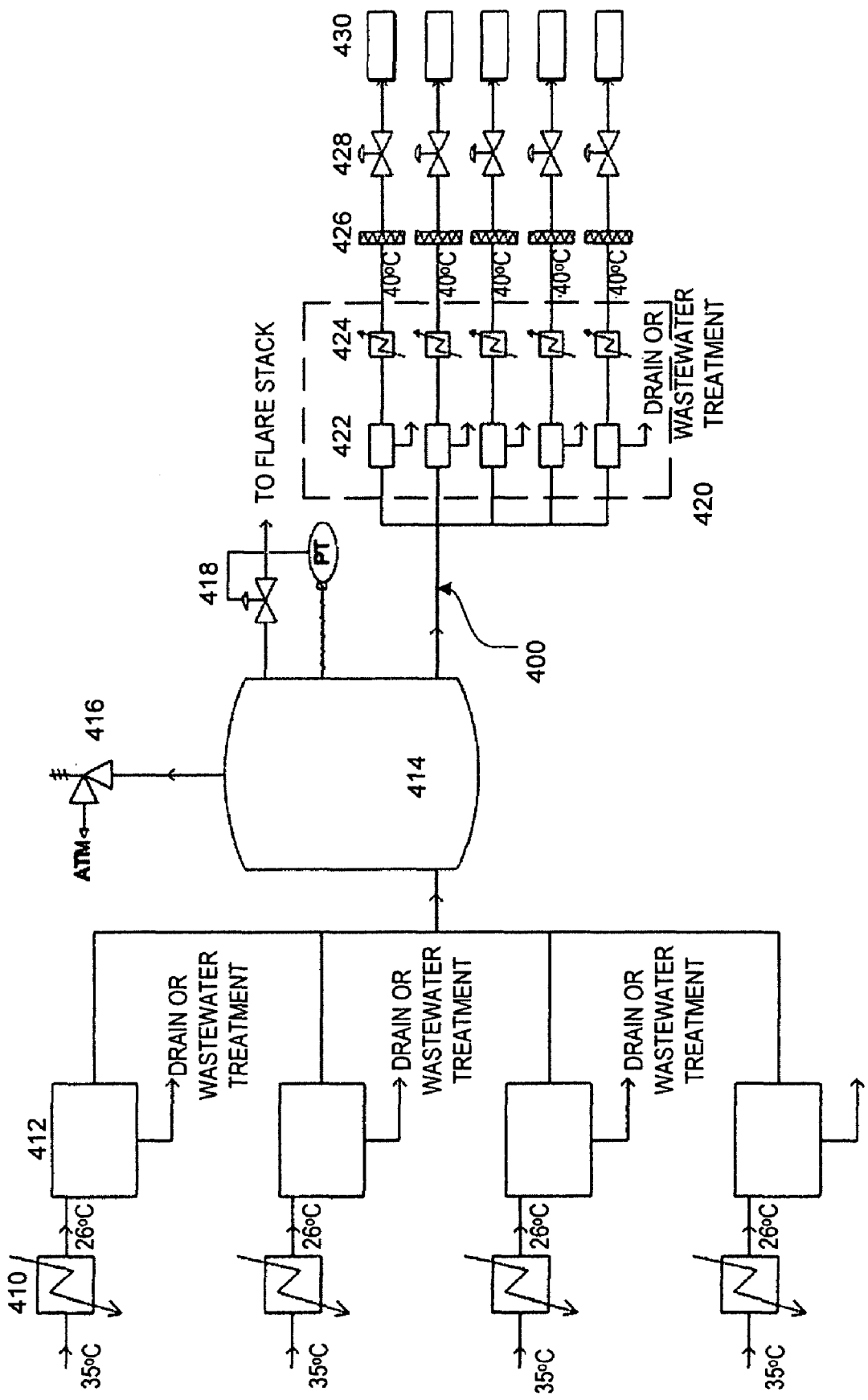
FIG. 4 is an illustration of a gas homogenization system, in accordance with one embodiment of the invention, where gas is delivered from multiple sources to a single homogenization chamber and then delivered to multiple engines, each engine having its own gas conditioning skid.

FIG. 4 illustrates a gas homogenization system 400 configured in accordance with one embodiment of the invention which is configured for the production of a regulated gas. The gas homogenization system 400 comprises a series of chillers 410 and a series of gas/liquid separators 412, which feed into a single homogenization chamber 414; a series of gas conditioning skids 420, each skid comprising a gas/liquid separator 422 and a heater 424; a series of filters 426; and a series of pressure regulating valves 428. Thus, the regulated gas is generated from multiple gas sources and delivered to a series of engines 430, by way of a single homogenization chamber 414.

Figure 5:
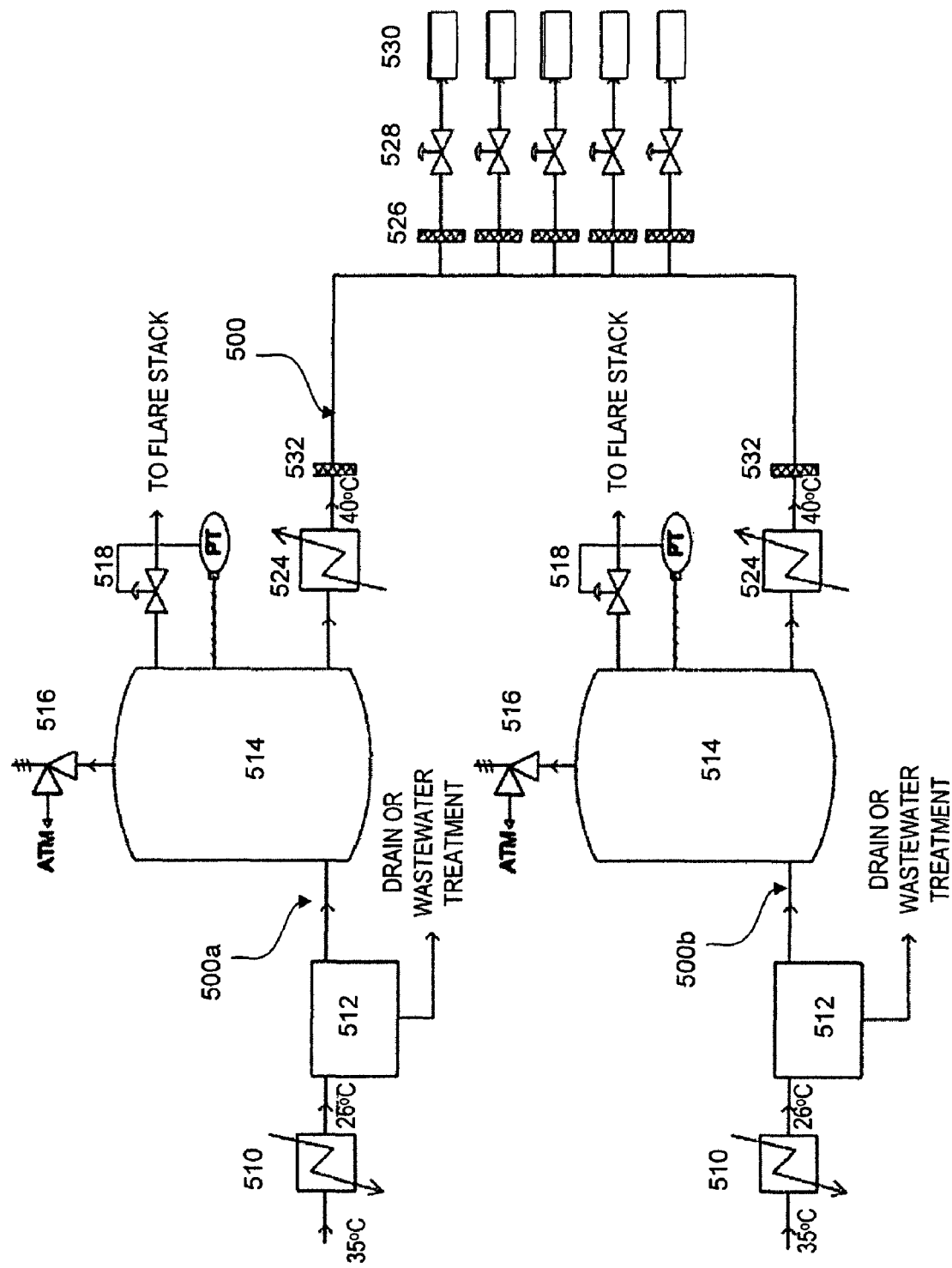
FIG. 5 is an illustration of a gas homogenization system, in accordance with one embodiment of the invention, where gas is delivered to multiple engines from two parallel streams, each stream comprising a single source of gas delivered to a single homogenization chamber.

FIG. 5 illustrates a gas homogenization system 500 configured in accordance with one embodiment of the invention which is configured for the production of a regulated gas. The gas homogenization system 500 comprises: two parallel streams of components 500a and 500b, each stream comprising a chiller 510, a gas/liquid separator 512, a homogenization chamber 514, a heater 524, and a filter 532. The regulated gas from the two streams 500a and 500b are combined and delivered to a series of engines 530 by way of a series of filters 526, and a series of pressure regulating valves 528.

The above figures relate to exemplary configurations of the gas homogenization system and are, therefore, not intended to limit the scope of the invention in any way. As would be apparent to a worker skilled in the art, other suitable configurations of a gas homogenization system would be useful in producing a regulated gas that satisfies the requirements of a downstream application. Accordingly, such configurations are also herein contemplated.

1) Homogenization Chamber

As previously mentioned, the gas homogenization chamber of the invention receives gas produced from a gasification system and encourages mixing or blending of the gas to attenuate fluctuations in the chemical composition of the gas within the homogenization chamber. Fluctuations in other gas characteristics, such as pressure, temperature and flow rate, can also be reduced during mixing of the gas.

In one embodiment of the invention, the dimensions of the chamber are designed according to the performance characteristics of an upstream gasification system and the requirements of a downstream application, with the objective of substantially minimizing the size of the chamber as much as possible. The gas homogenization chamber is designed to receive gas from a gasification process and retain the gas for a certain residence time to allow for sufficient mixing or blending of the gas in order to dampen disturbances and/or fluctuations and achieve a volume of gas with a substantially consistent chemical composition.

In one embodiment of the invention, the dimensions of a homogenization chamber can be calculated based on the total system response time which includes the process residence time between the converter and the analyzer sample probe, plus the total system response time for the sample system, analysis and transmission time to a plant control system (PCS).

Residence Time

The residence time is the average amount of time that gas remains in the homogenization chamber before being directed to a downstream application. The residence time is substantially proportional to the response time of the related gasification system to dampen the effect of the rate of change of the fluctuations in the gasification reaction in order to achieve gas characteristics that fall within accepted tolerance values. For example, the gas composition is retained in the homogenization chamber long enough to determine whether it falls within the gas composition tolerance allowed for the particular downstream application as well as to make any adjustments to the gasification process to adjust for the deviance. In this way, the system can affect the rate of change in gas characteristics so that upstream controls with fast process lags will be able to meet the specifications of a downstream application. In one embodiment, the residence time is determined by about 1% maximum change in the lower heating value (LHV) per 30 seconds and a maximum change in pressure of about 0.145 psi/second.

Residence time of the gas in the homogenization chamber is determined by the amount of variance in the gas characteristics. That is, the smaller the variance in gas characteristics, the shorter the residence time required in the homogenization chamber to correct for this variance.

Depending on the different embodiments of the present invention, the residence time can vary from less than about one minute to about 20 minutes. In one embodiment, the residence time ranges from about 15 to about 20 minutes. In one embodiment the residence time ranges from about 10 to about 15 minutes. In one embodiment, the residence time ranges from about 5 to about 10 minutes. In one embodiment of the invention, the residence time ranges from about 3 to about 5 minutes. In one embodiment of the invention, the residence time ranges from about 1 to about 3 minutes. In one embodiment of the invention, the residence time ranges from amounts less than about one minute.

In one embodiment, the residence time is about 20 minutes. In one embodiment the residence time is about 18 minutes. In one embodiment, the residence time is about 15 minutes. In one embodiment, the residence time is about 13 minutes. In one embodiment, the residence time is about 10 minutes. In one embodiment, the residence time is about 8 minutes. In one embodiment, the residence time is about 6 minutes. In one embodiment, the residence time is about 4 minutes. In one embodiment, the residence time is about 3 minutes. In one embodiment, the residence time is about 2 minutes. In one embodiment, the residence time is about 1 minute. In one embodiment, the residence time is less than about 1 minute.

Volume Capacity

As mentioned earlier, the volume capacity of the homogenization chamber is related to the residence time required for a specific downstream application and fluctuations that are expected because of heterogeneity of the feedstock. In one embodiment of the invention, the variable gas volume ranges from about 0-290 m$^3$. In one embodiment, the variable gas volume ranges from about 0-1760 m$^3$. In one embodiment, the variable gas volume ranges from about 0-2050 m$^3$. In one embodiment, the variable gas volume ranges from about 0-30,000 m$^3$. In one embodiment of the invention, the homogenization chamber has a maximum capacity of about 290 m$^3$. In one embodiment, the homogenization chamber has a maximum capacity of about 1800 m$^3$. In one embodiment of the invention, the homogenization chamber has a maximum capacity of about 2300 m$^3$. In one embodiment of the invention, the homogenization chamber has a maximum capacity of about 30,000 m$^3$.

Design Pressure and Possibilities of Low Pressure and High Pressure Chambers/Systems The downstream application selected can directly impact the operating pressure of the homogenization chamber. For example, a gas engine will require a gas pressure of about 1.2-3.0 psig while a gas turbine will require a gas pressure of about 250-600 psig. The mechanical design pressure of the homogenization chamber is correspondingly calculated to accommodate the required operating pressure for a selected application. In one embodiment, the homogenization chamber has a mechanical design pressure suitable for maintaining the gas pressure for use in a gas engine. In one embodiment, the homogenization chamber has a mechanical design pressure suitable for maintaining the gas pressure for use in a gas turbine. In one embodiment the homogenization chamber has a mechanical design pressure of about 5.0 psig. In one embodiment of the invention, the homogenization chamber has a mechanical design pressure of about 10.0 psig. In one embodiment of the invention, the homogenization chamber has a mechanical design pressure of about 25.0 psig. In one embodiment of the invention, the homogenization chamber has a mechanical design pressure in the range of about 100 to about 600 psig.

One skilled in the art can also appreciate that to meet the requirements of downstream applications, such as a gas engine, a lower pressure system would be more advantageous than for other applications, such as a gas turbine, where a higher pressure gas stream would be more appropriate.

Design Temperature

The homogenization chamber has a mechanical design temperature tolerance that will accommodate the gas being contained and the specifications of the downstream application. Typically, these temperatures will range from about −40° C. to about 300° C. In one embodiment of the invention, the mechanical design temperature of the chamber ranges from about −37° C. to about 93° C.

Type and Shape of Homogenization Chambers

A person skilled in the art will appreciate that the homogenization chamber can be formed in a variety of shapes provided functional requirements of the homogenization system, discussed above, are satisfied. One skilled in the art will also appreciate that the shape and size of the chamber will depend on the gas throughput and residence time required for a specific design, as discussed above. Cost and maintenance are additional considerations in selecting a type of homogenization chamber.

Different types of homogenization chambers include, but are not limited to gasometers, gas holders, variable volume and fixed volume tanks, such as standard fuel tanks and surge tanks. Thus, in accordance with one embodiment of the invention, the homogenization chamber is a standard fuel tank. In accordance with one embodiment of the invention, the homogenization chamber is a fixed volume tank such as a surge tank. In accordance with one embodiment of the invention, the homogenization chamber is a variable volume tank. In accordance with one embodiment of the invention, the homogenization chamber is a gasometer or gas holder.

Figure 6:
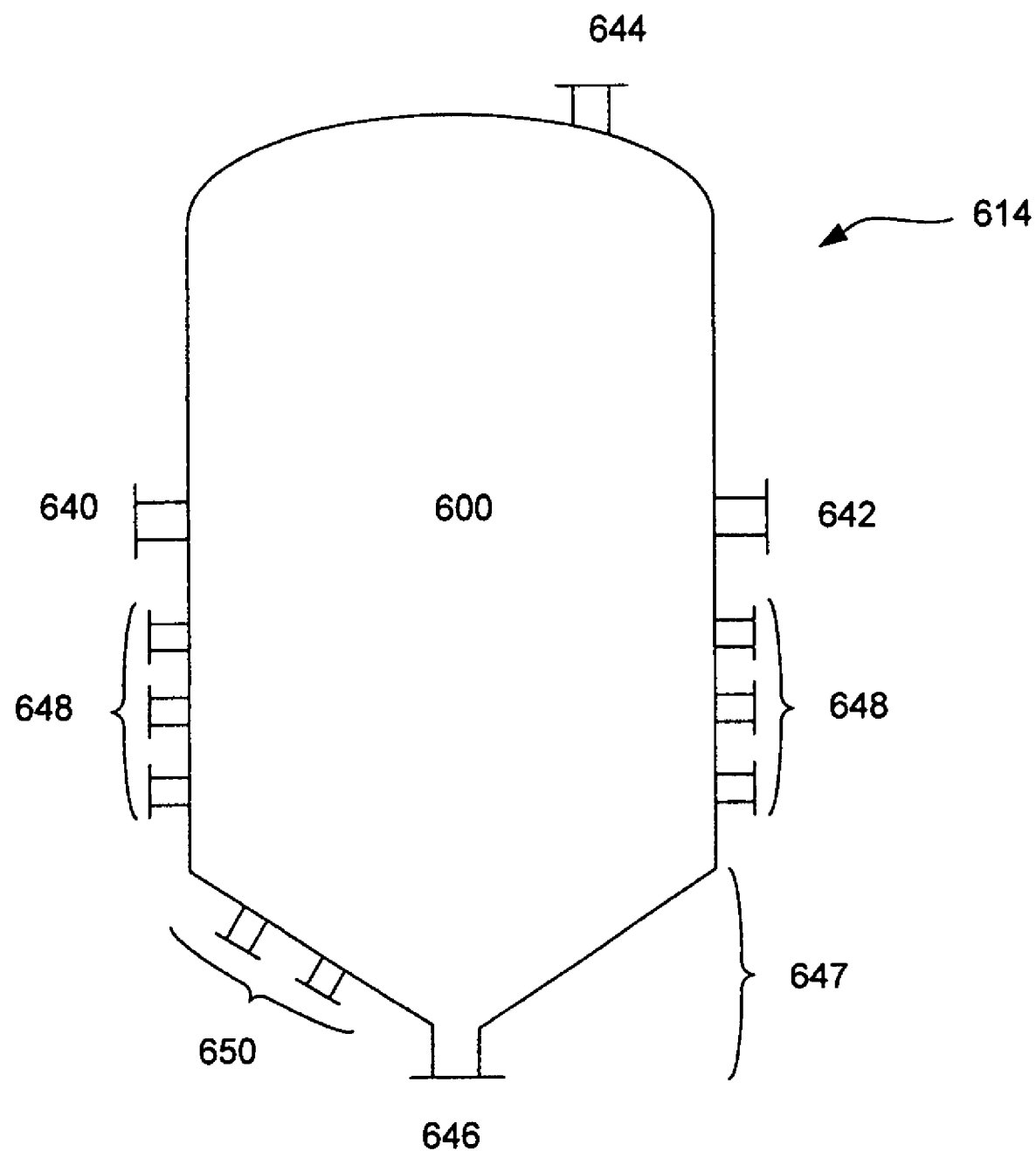
FIG. 6 is an illustration of a constant-volume homogenization chamber, in accordance with one embodiment of the invention.

With reference to FIG. 6, a homogenization chamber 614, in accordance with one embodiment of the invention, comprises a fixed-volume tank 600, a gas inlet 640, a gas outlet 642, a relief gas outlet 644, a drain 646, one or more pressure/temperature nozzles 648 and one or more level switch nozzles 650. The drain 646 of the tank 600 is a feature of the conical bottom drainage system 647, which may be associated with insulation means or other suitable means, such as immersion heaters, to prevent freezing of the condensate in colder climates. Optionally, the tank 600 comprises fins or baffles to enhance mixing of the gas, wherein the selection, shape, number and placement of which would be understood by those of skill in the art.

Figure 7:
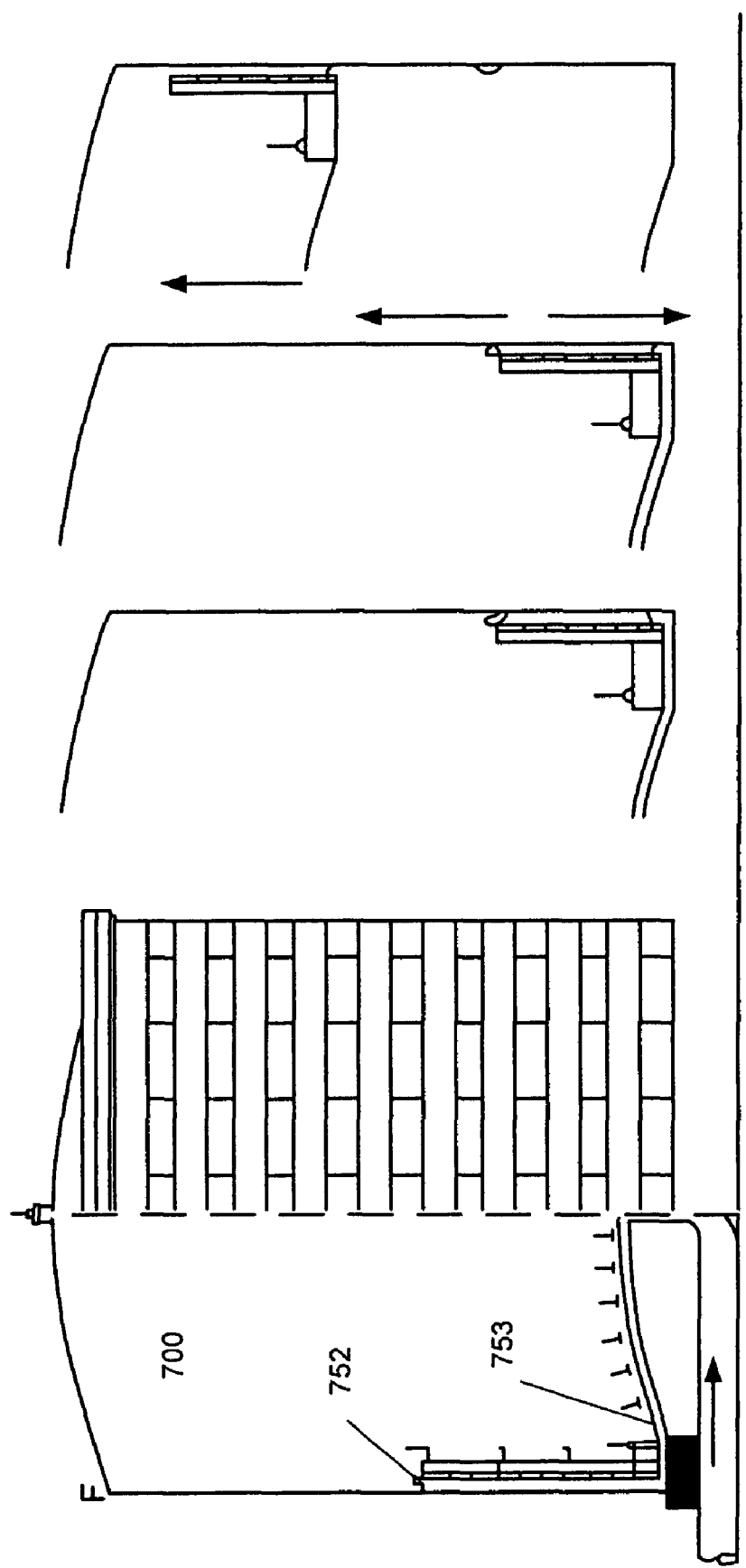
FIG. 7 is an illustration of the design and functionality of a variable-volume homogenization chamber, in accordance with one embodiment of the invention.

Referring to FIG. 7, homogenization chamber 714, in accordance with one embodiment of the invention, will now be described. The homogenization chamber 714 (also known as a floating roof homogenization chamber), is able to accommodate small fluctuations in pressure. The homogenization chamber 714, comprises a variable volume tank 700 having a gas inlet 751, and a diaphragm 753 connected to a piston 752, which act together to increase or decrease the tank volume.

Figure 8:
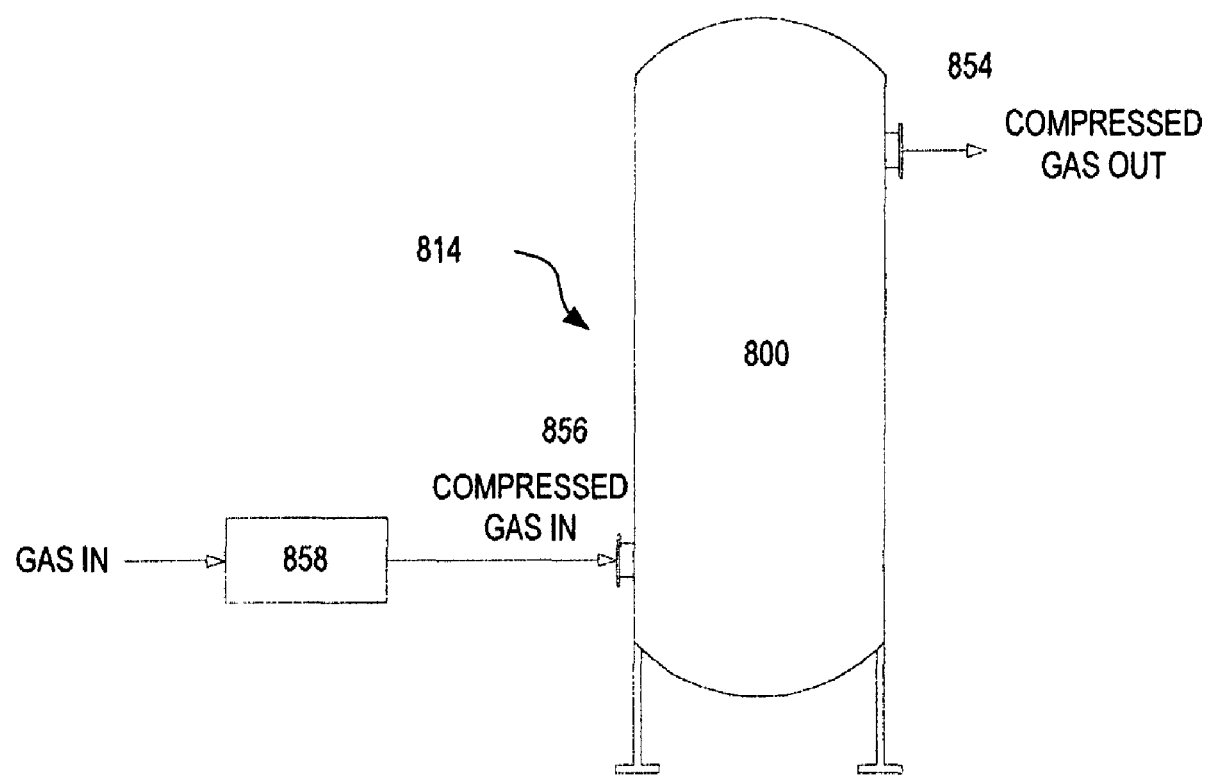
FIG. 8 is an illustration of a homogenization chamber configured as pressure vessel and compressor combination, in accordance with one embodiment of the invention.

With reference to FIG. 8, a homogenization chamber 814, in accordance with one embodiment of the invention, will now be described. The homogenization chamber 814 (also known as a pressure vessel), comprises a gas outlet 854 and a gas inlet 856. The gas inlet is connected to a compressor 858, which functions to compress the gas prior to storage in the pressure vessel 800. A worker skilled in the art will readily understand that since the gas is compressed prior to storage in the pressure vessel, the pressure vessel can be smaller than traditional low pressure tanks.

Figure 9:
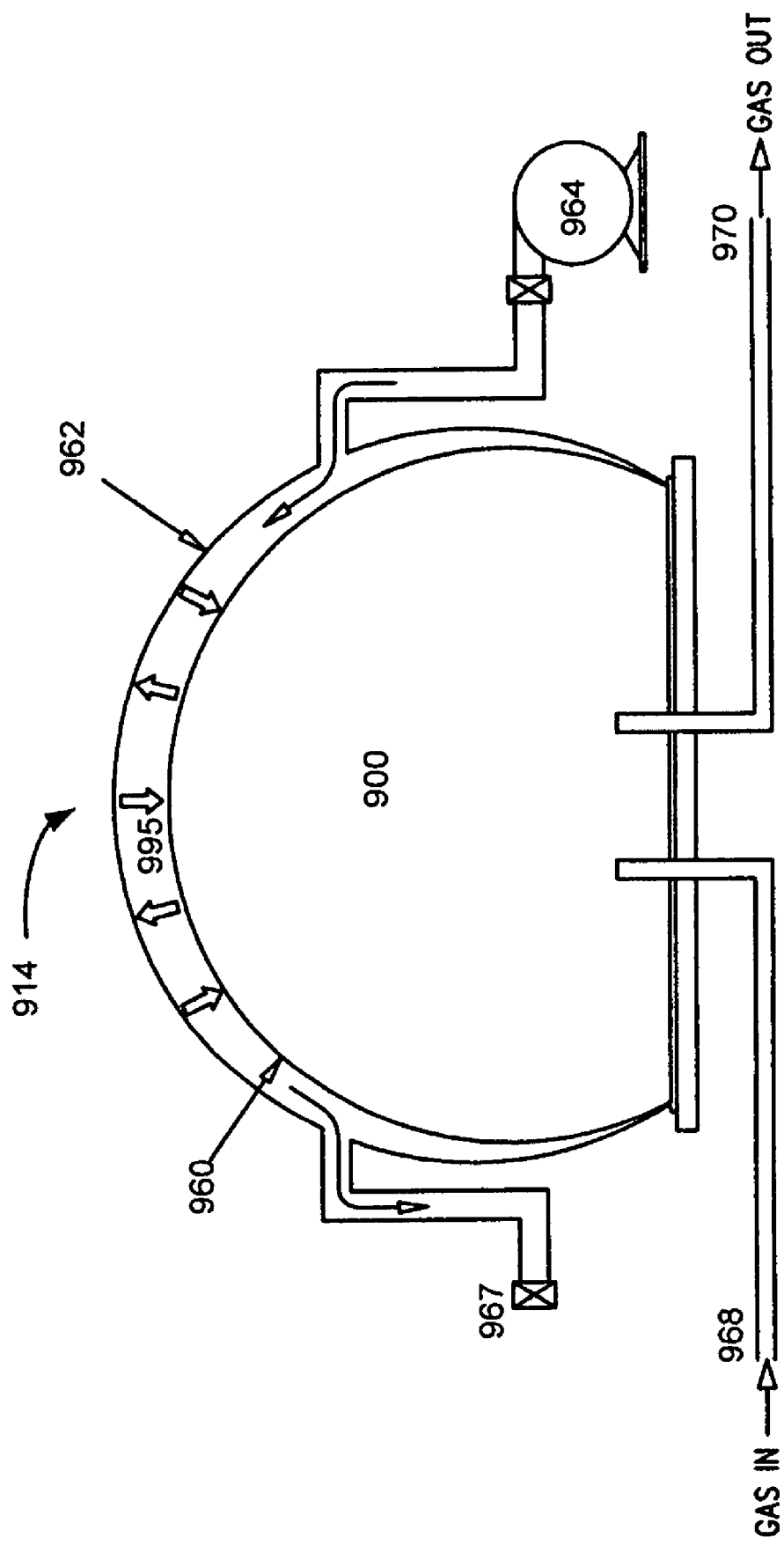
FIG. 9 is an illustration of a homogenization chamber configured as a double membrane gas holder, in accordance with one embodiment of the invention.

With reference to FIG. 9, a homogenization chamber 914, in accordance with one embodiment of the invention, comprises a gas holding chamber 900 connected to a gas inlet 968 and a gas outlet 970 and defined by an inner membrane 960 and an outer membrane 962. When gas exits the holding chamber 900, a blower 964, associated with the outer membrane 962, provides inflation to the region 965 between the membranes. When gas is added to the holding chamber 900, a regulator 967, adjusts the pressure of the inflated region 965.

Figures 10A, 10B:
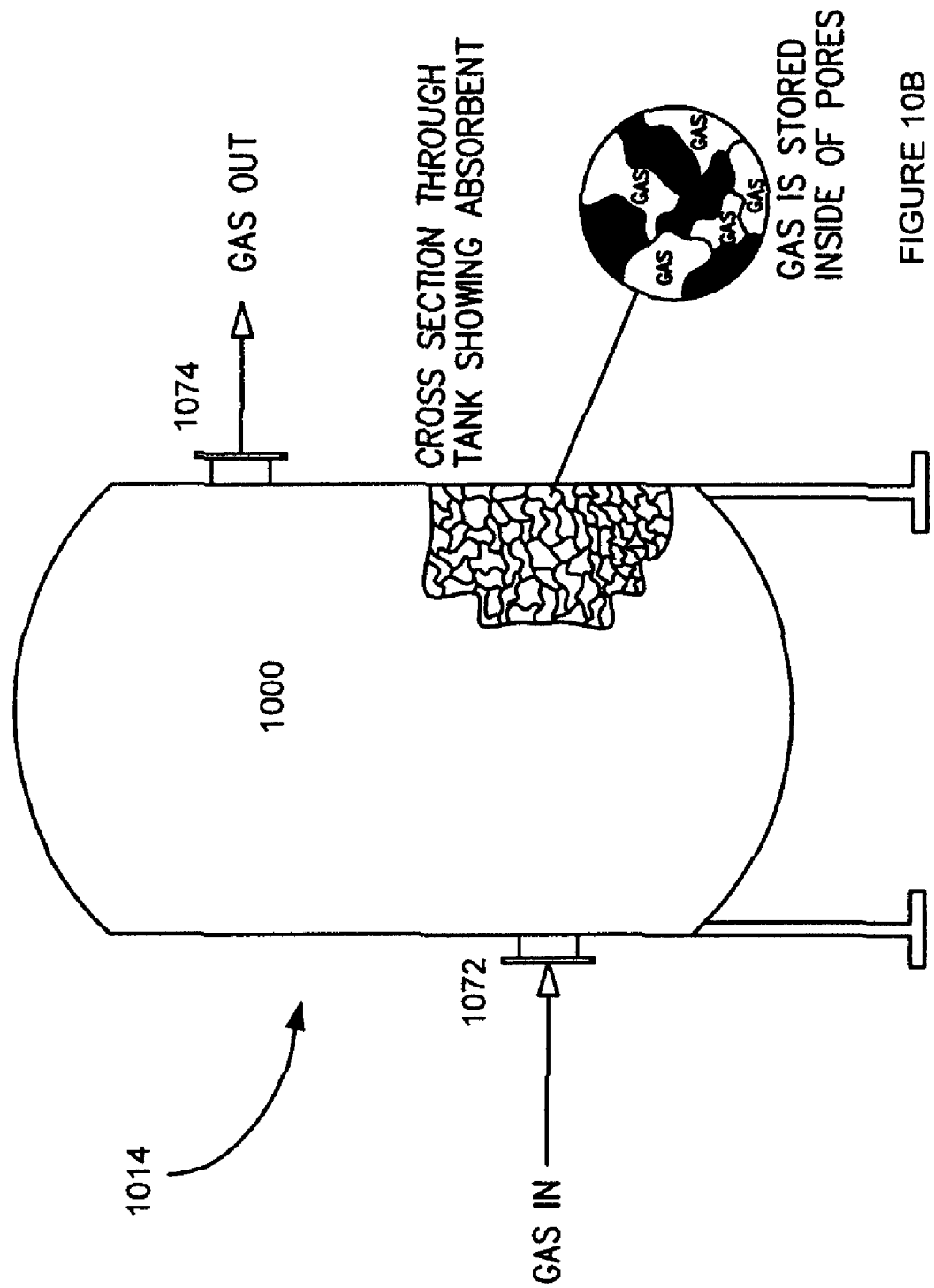
FIG. 10A is an illustration of a homogenization chamber configured as an absorption-type gas holder, in accordance with one embodiment of the invention.
FIG. 10B is a cross-sectional view of the absorption-type gas holder showing the design of the absorbent material.

Referring to FIG. 10A, a homogenization chamber 1014, in accordance with one embodiment of the invention, will now be described. In this embodiment, the homogenization chamber 1014 is an absorption type gas holder comprising a constant volume tank 1000 having a gas inlet 1072 and a gas outlet 1074. Typically, a gas absorption holder occupies less space than a traditional low pressure storage tank, due to the high density storage of the absorbent. FIG. 10B illustrates a cross sectional view of the tank 1000, which acts to absorb gas molecules.

Figure 11:
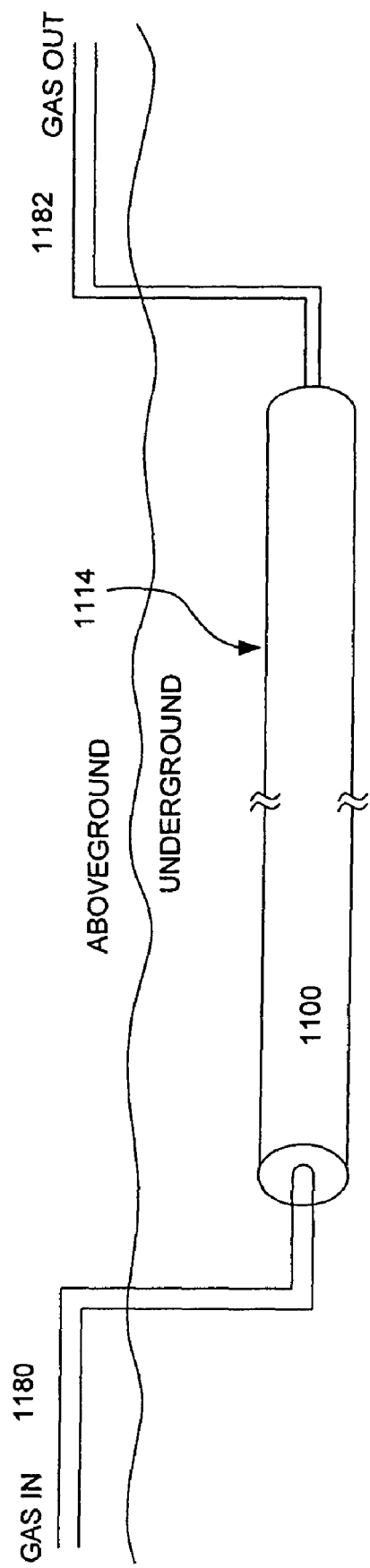
FIG. 11 is an illustration of a homogenization chamber configured as an underground constant volume large diameter pipe, in accordance with one embodiment of the invention.

With reference to FIG. 11, a homogenization chamber 1114, in accordance with one embodiment of the invention, will now be described. In this embodiment, the homogenization chamber is a pipe with a diameter that is sized to provide the required residence time. The fixed-volume, pipe 1100 comprises a gas inlet means 1180 and gas outlet means 1182. This embodiment of a homogenization chamber can be particularly suited for applications that require minimal residence time for homogenizing the gas.

Typically, a homogenization chamber of the invention will be located above ground. However, it is contemplated that for aesthetic reasons, or in those jurisdictions which do not allow above ground containment of fuel, a homogenization chamber may be located underground. Thus, in one embodiment, the homogenization chamber is underground. In one embodiment, the homogenization chamber is above ground. In one embodiment of the invention, the homogenization chamber is positioned such that a portion thereof is underground.

Figure 12:
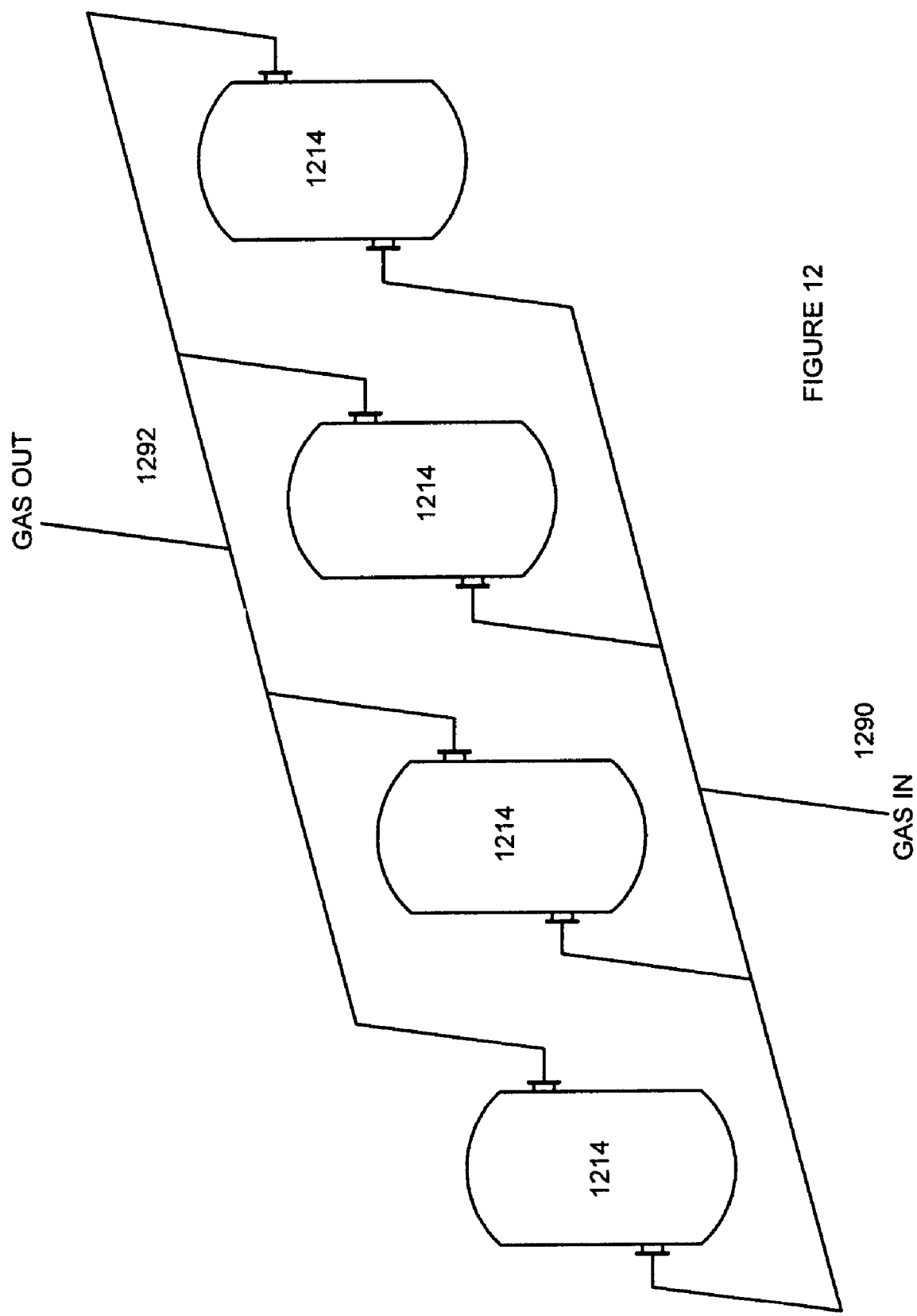
FIG. 12 is an illustration of a plurality of constant-volume homogenization chambers arranged in parallel, in accordance with one embodiment of the invention.

It is further contemplated that a homogenization chamber of the invention can be configured as a homogenization system with more than one chamber or may be configured as one or more single homogenization chambers fluidly interconnected in parallel. FIG. 12 is an illustration of a plurality of fixed-volume, homogenization chambers installed in parallel, each homogenization chamber 1214 being connected to a single gas inlet manifold 1290 and a single gas outlet manifold 1292. A worker skilled in the art will readily appreciate that each of the fixed-volume, homogenization chamber used in FIG. 12 could be independently selected as one of the above-mentioned embodiments, for example, a pressure vessel, a double-membrane gas holder, a multiple-absorption type gas holder etc., provided there is a single gas inlet and a single gas outlet for the entire system. A worker skilled in the art would be able to ascertain the suitability of such designs for a given purpose.

Materials

It is known that gas from a gasification system can be highly toxic and flammable, and in most cases will be contained outdoors exposed to various environmental conditions such as extreme temperature changes, rain, sun, snow, wind and the like. Accordingly, a homogenization chamber will be manufactured from a suitably safe material. Non-limiting examples of materials include plastics (PVC), steel, composite materials such as fiberglass reinforced plastic or steel, and steel alloys. Gas homogenization chambers comprising a combination of these materials are also herein contemplated, as are metals comprising suitable internal coatings. Coated metals, for example, can be useful for those chambers located underground due to the added environmental protection provided by such a coating. Coated metals may also be required to satisfy governmental regulations.

Gas Monitoring within the Homogenization Chamber

One skilled in the art will appreciate that the gas characteristics of the input gas will be monitored during the gas homogenization process in order to determine whether the gas meets the downstream requirements and what adjustments are required in order to satisfy such requirements. Monitoring of the gas characteristics may occur within the homogenization chamber or prior to gas delivery to the homogenization chamber. The gas monitoring equipment may take the form of sensing elements, response elements, and controllers that can monitor and/or regulate the composition, flow rate, temperature and pressure of the gas.

The monitoring of the gas characteristics may be part of a process control system (see FIG. 15 and Control System section provided below). Thus, in one embodiment of the invention, a feedback loop can be implemented in which the gas produced is analyzed in real-time and the operation of the gasification system is adjusted accordingly in order to make the necessary adjustments.

In one embodiment, the homogenization chamber comprises one or more sensing elements for analyzing gas characteristics such as gas composition, temperature, flow rate and pressure, the configuration of each sensing element would be readily understood by a worker skilled in the art. For example, temperature can be measured using a thermocouple, or other temperature sensor format; pressure can be measured using an absolute pressure sensor, a gauge pressure sensor, vacuum pressure sensor, differential pressure sensor or other pressure sensor; flow rate can be measured using a flowmeter or other flow rate sensor; gas composition can be measured using a gas composition sensor based on acoustic properties, or other gas composition sensor as would be readily understood.

In one embodiment, a particular sensing element can be configured to measure multiple characteristics of the gas, wherein these types of sensors would be readily understood by a worker skilled in the art.

In one embodiment, the homogenization chamber further includes one or more controllers configured to generate instructions for transmission to one or more response elements in order to regulate gas characteristics such as gas composition, temperature, flow rate and pressure. Response elements contemplated within the present context, as defined and described above, can include, but are not limited to, various control elements operatively coupled to process-related devices configured to affect a given process by adjustment of a given control parameter related thereto. For instance, process devices operable within the present context via one or more response elements, may include, but are not limited to flow valves, pressure valves, heaters, blowers and the like.

In one embodiment of the invention, the feedback frequency associated with the feedback loop can directly depend on the parameters set by the controller, and possible rate at which these parameters can be adjusted within the system. The feedback frequency can be variable depending on the conditions being monitored or the feedback frequency can be a fixed frequency, or a random frequency.

In one embodiment of the invention, multiple sensing elements are positioned within the homogenization chamber in order to provide the capability of gas characteristic sampling at different locations within the chamber, thereby providing a means for evaluation of homogeneity of the gas therein. Furthermore, one or more redundant sensing elements can be positioned within the homogenization chamber in order to ensure accurate operation of the one or more sensing elements, for example fault detection. In addition, in one embodiment, two or more sensing elements are used to evaluate the same parameter and the measured value of the parameter is defined as a correlation between the readings determined by the two or more sensing elements.

In one embodiment of the invention, a controller is operatively coupled to one or more sensing elements associated with the homogenization chamber in order to determine control instructions for modification of one or more parameters associated with the gas. For example a controller can comprise one or more of a variety of types of computing devices, computers, microprocessors, microcontrollers or other computing device format which includes a central processing units (CPU) and peripheral input/output devices to monitor parameters from peripheral devices that are operatively coupled to the controller. For example the peripheral devices can include the one or more sensing elements and/or one or more response elements. These input/output devices can also permit the CPU to communicate and control peripheral devices that are operatively coupled to the controller. The controller can be operatively coupled to a memory device. For example, the memory device can be integrated into the controller or it can be a memory device connected to the computing device via a suitable communication link. The memory device can be configured as an electronically erasable programmable read only memory (EEPROM), electronically programmable read only memory (EPROM), non-volatile random access memory (NVRAM), read-only memory (ROM), programmable read-only memory (PROM), flash memory or any other non-volatile memory for storing data. The memory can be used to store data and control instructions, for example, program code, software, microcode or firmware, for monitoring or controlling the one or more sensing elements which are associated with the homogenization chamber and are coupled to the controller and which can be provided for execution or processing by the CPU. Optionally, the controller also provides a means of converting user-specified operating conditions into control signals to control the response elements coupled to the controller. The controller can receive user-specified commands by way of a user interface, for example, a keyboard, a touchpad, a touch screen, a console, a visual or acoustic input device as is well known to those skilled in this art.

Control System

Figure 15:
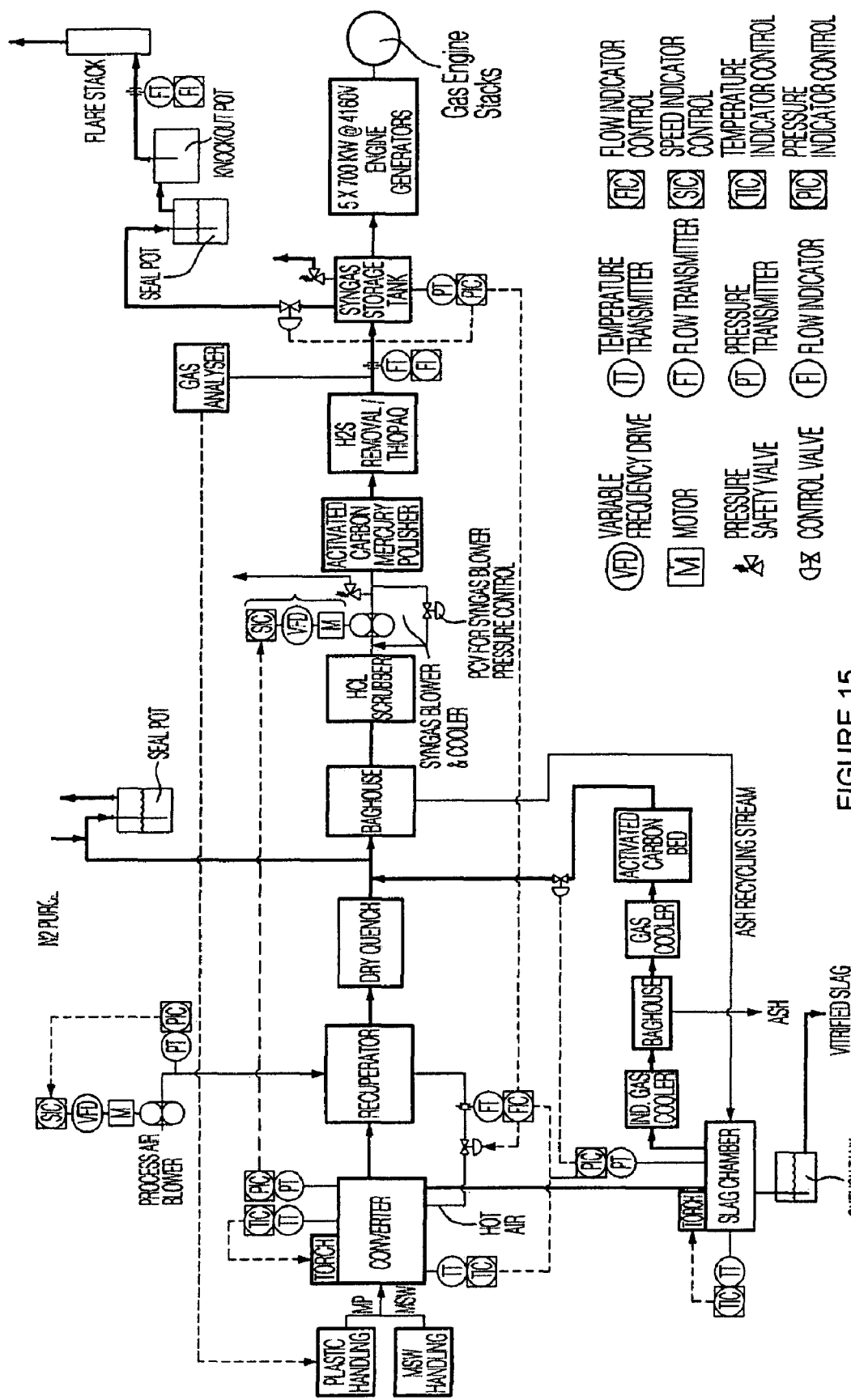
FIG. 15 is a flow diagram of a gasification process according to one embodiment of the invention.
Figure 16A:
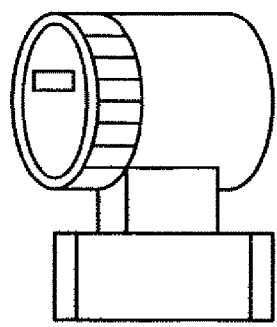
FIGS. 16A-D illustrate pressure regulating devices, in accordance with embodiments of the invention.
Figure 16B:
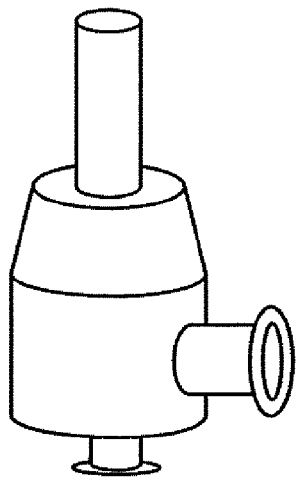
Figure 16C:
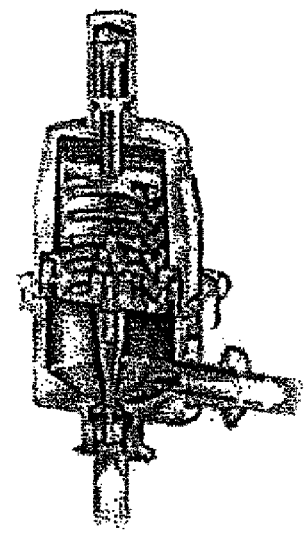
Figure 16D:
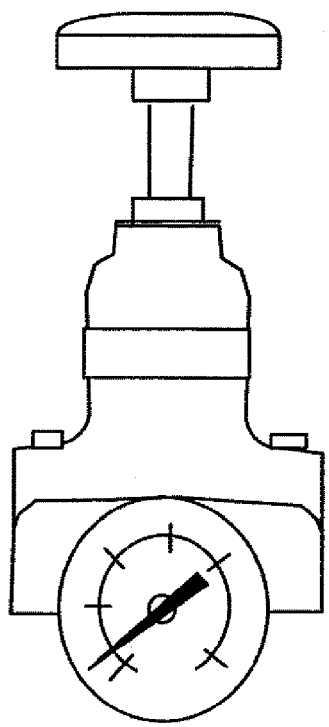
Figure 17A:
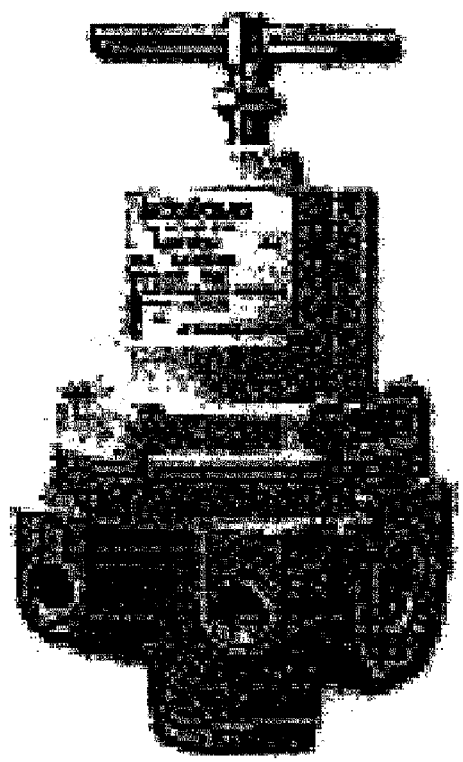
FIGS. 17A-D present flow regulating devices, in accordance with embodiments of the invention.
Figure 17D:
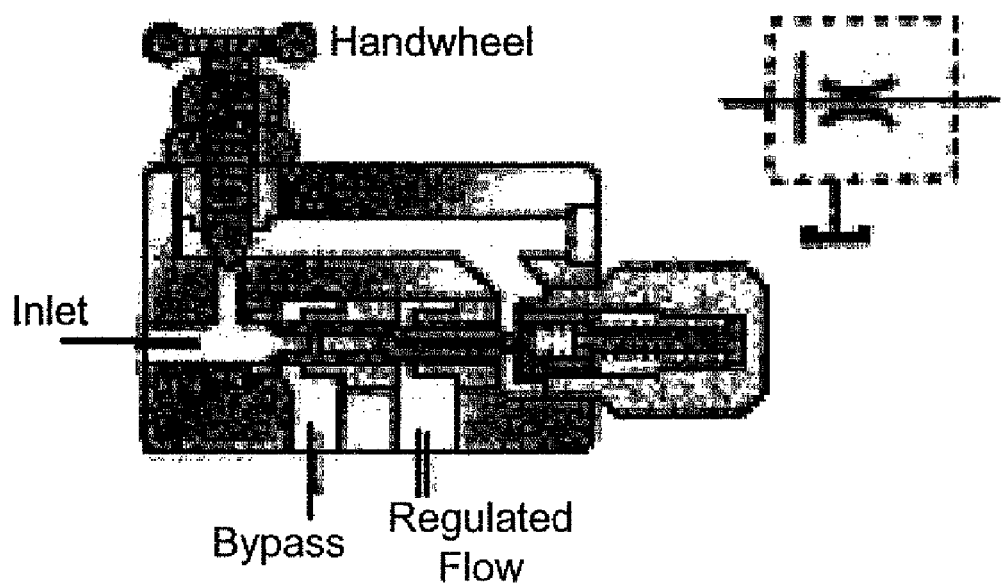
Figure 17B:
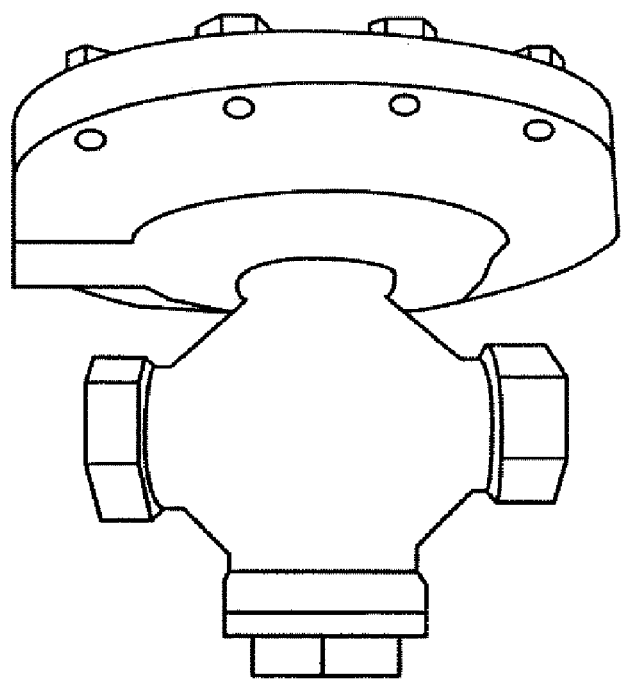
Figure 17C:
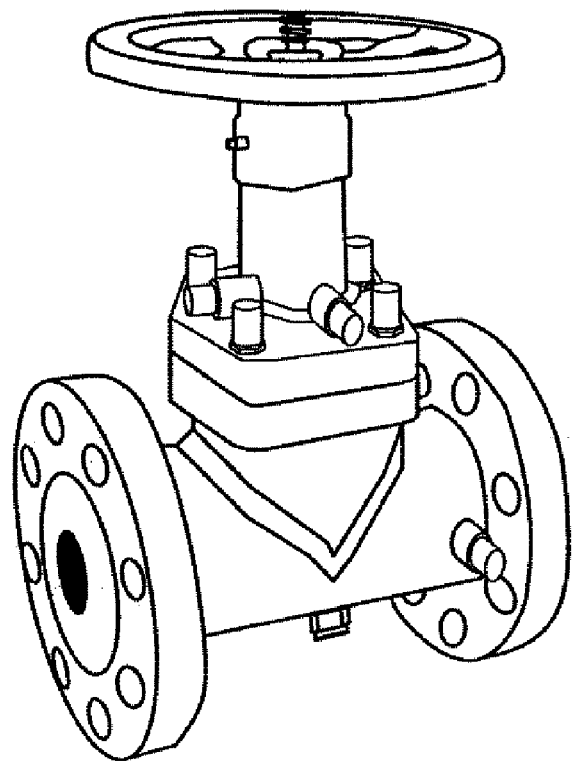
Figure 18:
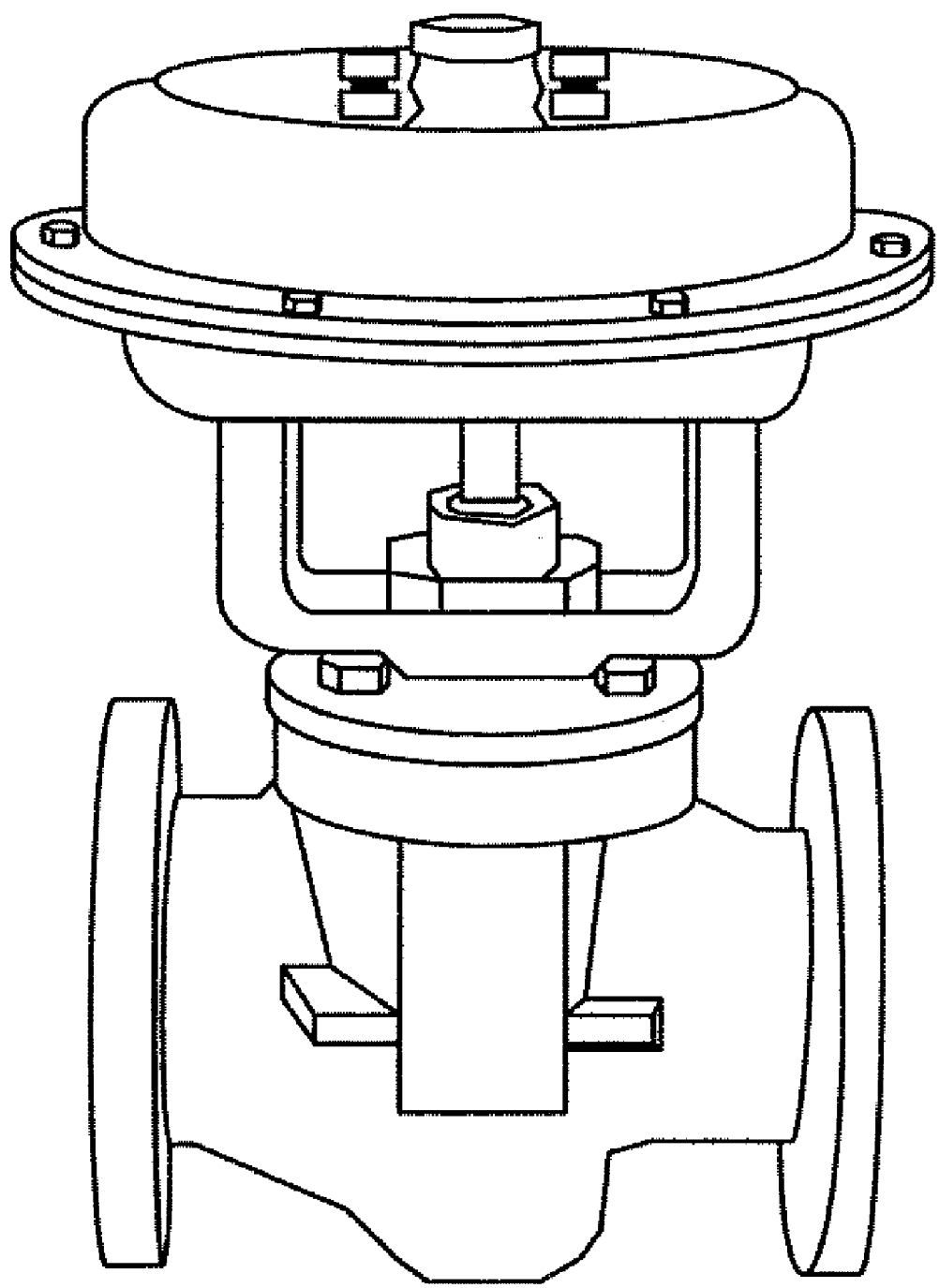
FIG. 18 presents a control valve in accordance with one embodiment of the invention.
Figures 19A, 19B, 19C:
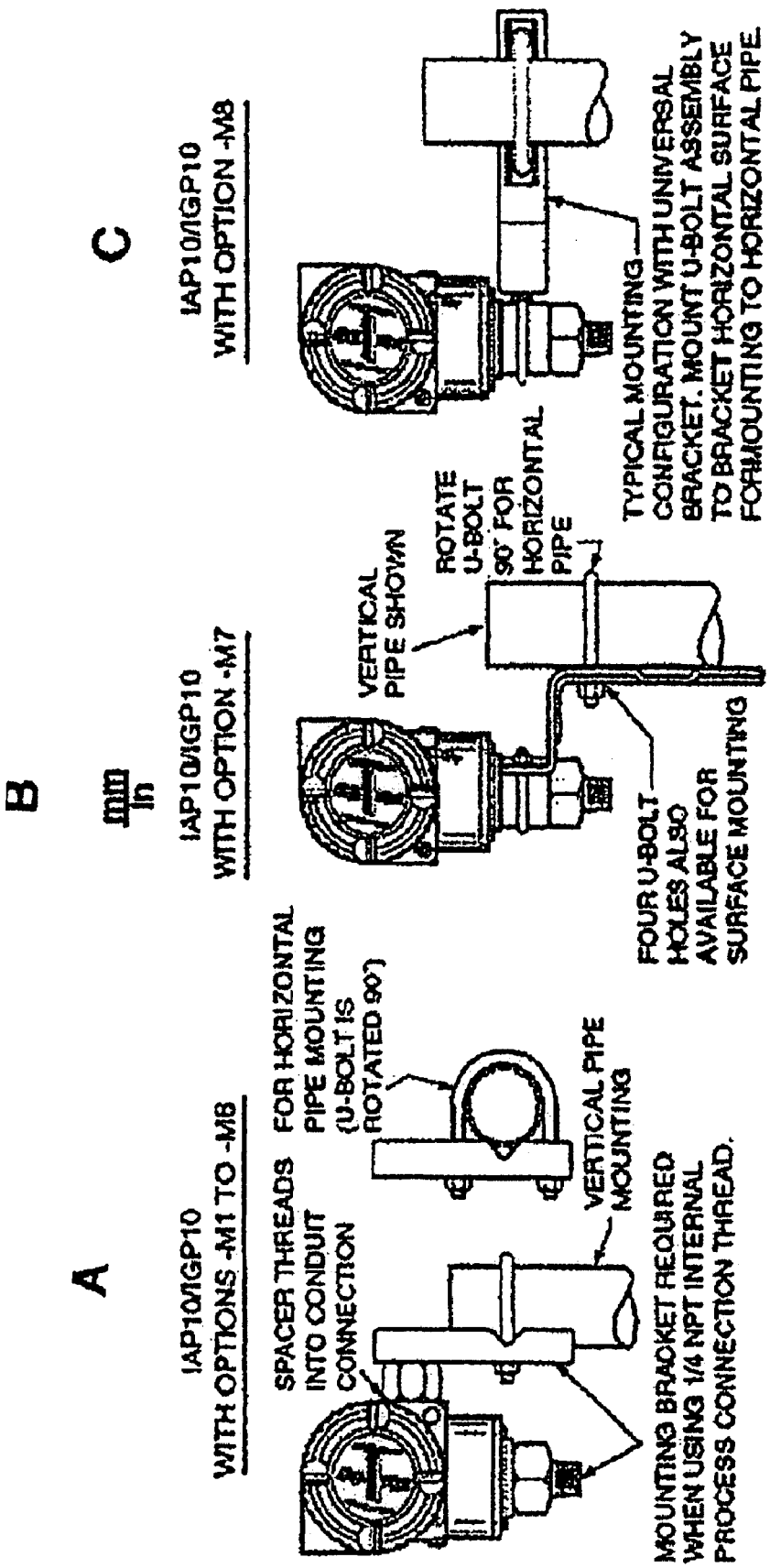
Figure 19K:
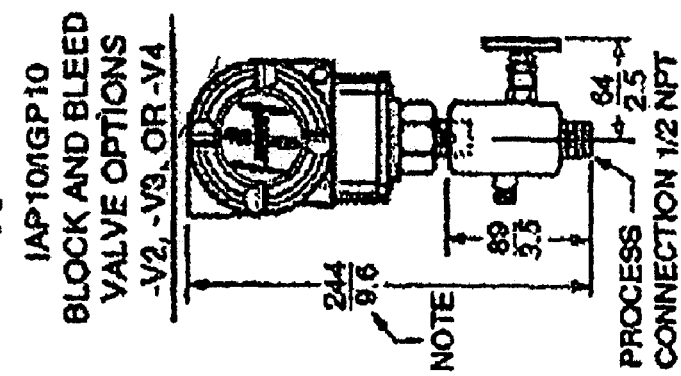
Figure 19J:
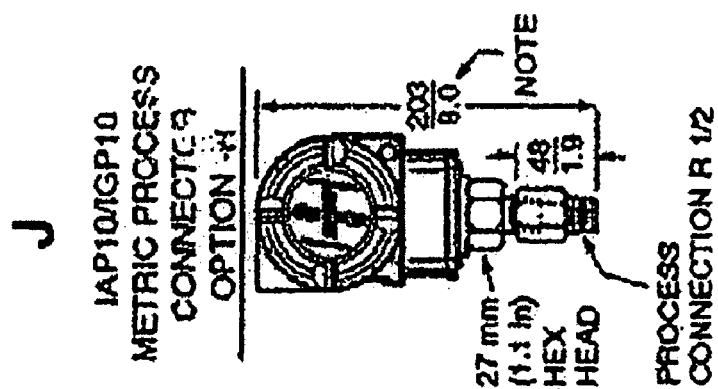
Figure 19I:
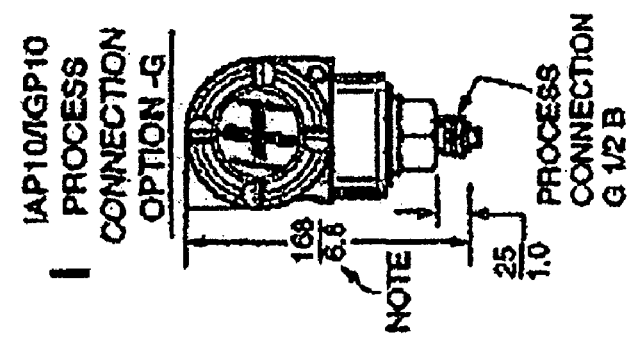
Figure 19H:
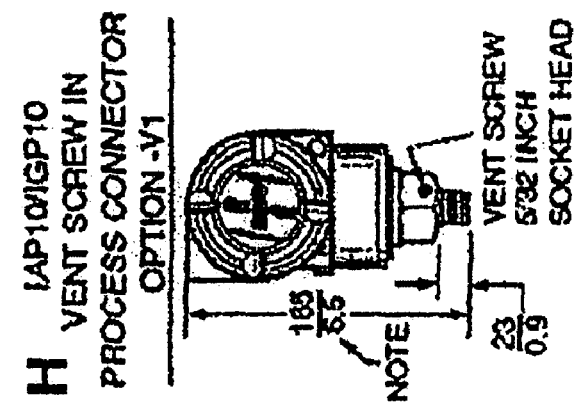
Figure 20A:
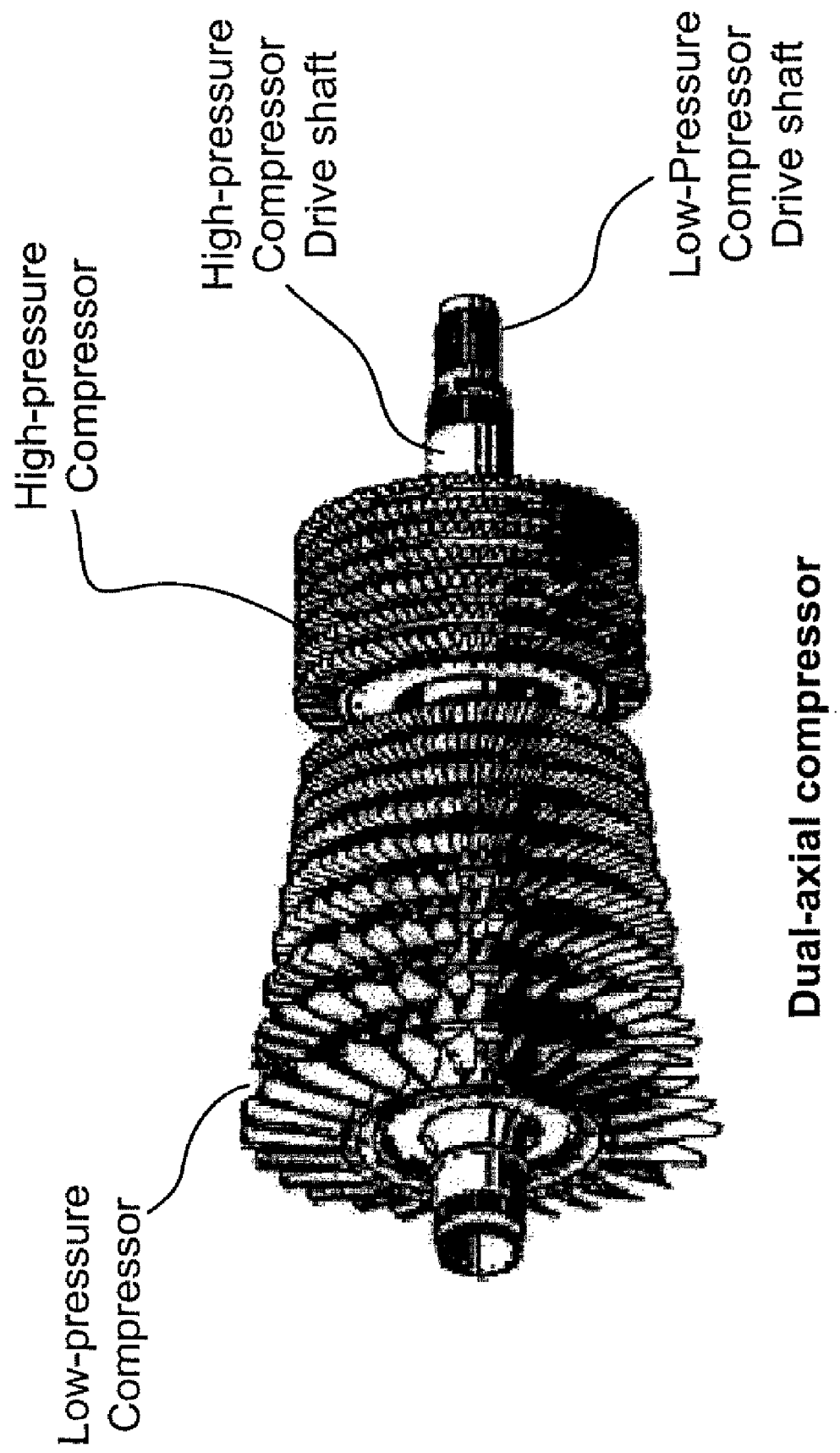
FIG. 20A illustrates an axial-flow compressor in accordance with one embodiment of the invention.
Figure 20B:
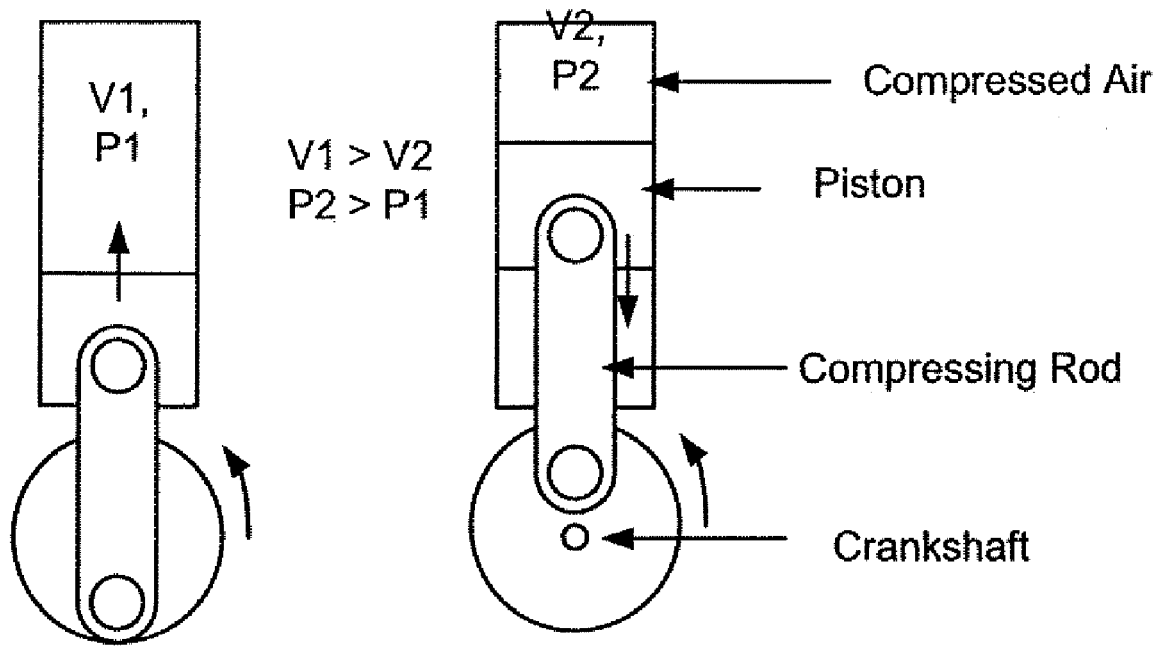
FIG. 20B illustrates a reciprocating compressor in accordance with one embodiment of the invention.
Figure 20C:
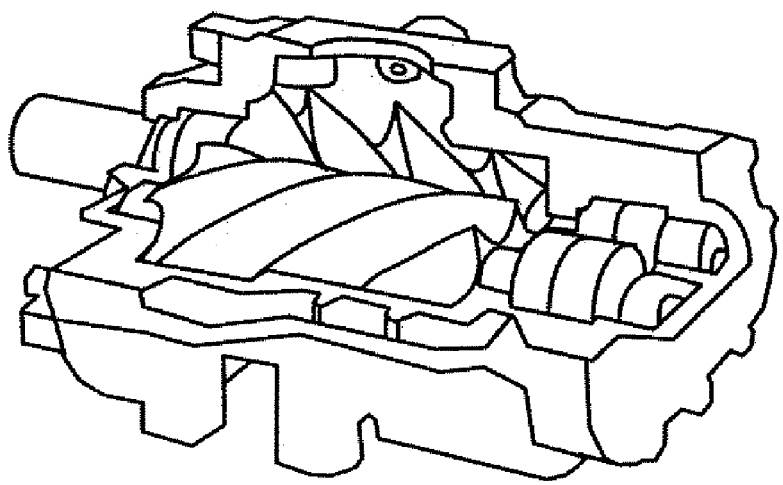
FIG. 20C illustrates a rotary screw compressor in accordance with one embodiment of the invention.
Figure 20D:
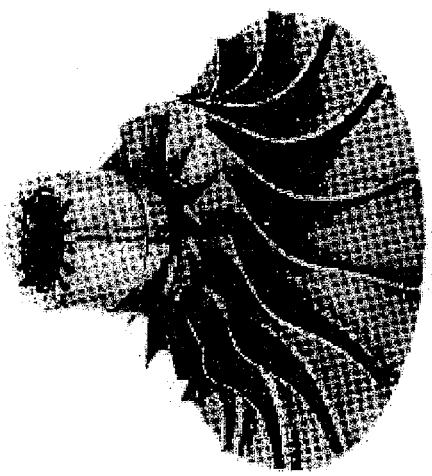
FIG. 20D illustrates a single stage centrifugal compressor in accordance with one embodiment of the invention.
Figure 20D:
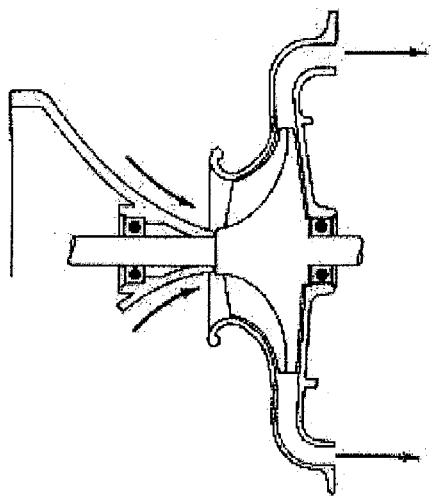
Figure 20E:
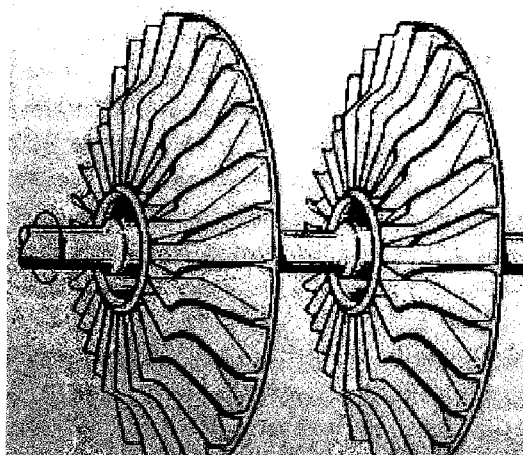
FIG. 20E illustrates a two-stage centrifugal compressor in accordance with one embodiment of the invention.
Figure 20E:
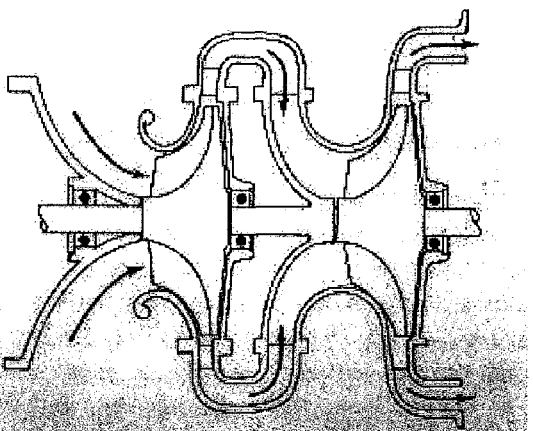

In one embodiment of the present invention, a control system, such as that illustrated at FIG. 15, may be provided to control one or more processes implemented in, and/or by, the various systems and/or subsystems disclosed herein, and/or provide control of one or more process devices contemplated herein for affecting such processes. In general, the control system may operatively control various local and/or regional processes related to a given system, subsystem or component thereof, and/or related to one or more global processes implemented within a system, such as a gasification system, within or in cooperation with which the various embodiments of the present invention may be operated, and thereby adjusts various control parameters thereof adapted to affect these processes for a defined result. Various sensing elements and response elements may therefore be distributed throughout the controlled system(s), or in relation to one or more components thereof, and used to acquire various process, reactant and/or product characteristics, compare these characteristics to suitable ranges of such characteristics conducive to achieving the desired result, and respond by implementing changes in one or more of the ongoing processes via one or more controllable process devices.

The control system generally comprises, for example, one or more sensing elements for sensing one or more characteristics related to the system(s), process(es) implemented therein, input(s) provided therefor, and/or output(s) generated thereby. One or more computing platforms are communicatively linked to these sensing elements for accessing a characteristic value representative of the sensed characteristic(s), and configured to compare the characteristic value(s) with a predetermined range of such values defined to characterise these characteristics as suitable for selected operational and/or downstream results, and compute one or more process control parameters conducive to maintaining the characteristic value with this predetermined range. A plurality of response elements may thus be operatively linked to one or more process devices operable to affect the system, process, input and/or output and thereby adjust the sensed characteristic, and communicatively linked to the computing platform(s) for accessing the computed process control parameter(s) and operating the process device(s) in accordance therewith.

In one embodiment, the control system provides a feedback, feedforward and/or predictive control of various systems, processes, inputs and/or outputs related to the conversion of carbonaceous feedstock into a gas, so to promote an efficiency of one or more processes implemented in relation thereto. For instance, various process characteristics may be evaluated and controllably adjusted to influence these processes, which may include, but are not limited to, the heating value and/or composition of the feedstock, the characteristics of the product gas (e.g. heating value, temperature, pressure, flow, composition, carbon content, etc.), the degree of variation allowed for such characteristics, and the cost of the inputs versus the value of the outputs. Continuous and/or real-time adjustments to various control parameters, which may include, but are not limited to, heat source power, additive feed rate(s) (e.g. oxygen, oxidants, steam, etc.), feedstock feed rate(s) (e.g. one or more distinct and/or mixed feeds), gas and/or system pressure/flow regulators (e.g. blowers, relief and/or control valves, flares, etc.), and the like, can be executed in a manner whereby one or more process-related characteristics are assessed and optimized according to design and/or downstream specifications.

Alternatively, or in addition thereto, the control system may be configured to monitor operation of the various components of a given system for assuring proper operation, and optionally, for ensuring that the process(es) implemented thereby are within regulatory standards, when such standards apply.

In accordance with one embodiment, the control system may further be used in monitoring and controlling the total energetic impact of a given system. For instance, a a given system may be operated such that an energetic impact thereof is reduced, or again minimized, for example, by optimising one or more of the processes implemented thereby, or again by increasing the recuperation of energy (e.g. waste heat) generated by these processes. Alternatively, or in addition thereto, the control system may be configured to adjust a composition and/or other characteristics (e.g. temperature, pressure, flow, etc.) of a product gas generated via the controlled process(es) such that such characteristics are not only suitable for downstream use, but also substantially optimised for efficient and/or optimal use. For example, in an embodiment where the product gas is used for driving a gas engine of a given type for the production of electricity, the characteristics of the product gas may be adjusted such that these characteristics are best matched to optimal input characteristics for such engines.

In one embodiment, the control system may be configured to adjust a given process such that limitations or performance guidelines with regards to reactant and/or product residence times in various components, or with respect to various processes of the overall process are met and/or optimised for. For example, an upstream process rate may be controlled so to substantially match one or more subsequent downstream processes.

In addition, the control system may, in various embodiments, be adapted for the sequential and/or simultaneous control of various aspects of a given process in a continuous and/or real time manner.

In general, the control system may comprise any type of control system architecture suitable for the application at hand. For example, the control system may comprise a substantially centralized control system, a distributed control system, or a combination thereof. A centralized control system will generally comprise a central controller configured to communicate with various local and/or remote sensing devices and response elements configured to respectively sense various characteristics relevant to the controlled process, and respond thereto via one or more controllable process devices adapted to directly or indirectly affect the controlled process. Using a centralized architecture, most computations are implemented centrally via a centralized processor or processors, such that most of the necessary hardware and/or software for implementing control of the process is located in a same location.

A distributed control system will generally comprise two or more distributed controllers which may each communicate with respective sensing and response elements for monitoring local and/or regional characteristics, and respond thereto via local and/or regional process devices configured to affect a local process or sub-process. Communication may also take place between distributed controllers via various network configurations, wherein a characteristics sensed via a first controller may be communicated to a second controller for response thereat, wherein such distal response may have an impact on the characteristic sensed at the first location. For example, a characteristic of a downstream product gas may be sensed by a downstream monitoring device, and adjusted by adjusting a control parameter associated with the converter that is controlled by an upstream controller. In a distributed architecture, control hardware and/or software is also distributed between controllers, wherein a same but modularly configured control scheme may be implemented on each controller, or various cooperative modular control schemes may be implemented on respective controllers.

Alternatively, the control system may be subdivided into separate yet communicatively linked local, regional and/or global control subsystems. Such an architecture could allow a given process, or series of interrelated processes to take place and be controlled locally with minimal interaction with other local control subsystems. A global master control system could then communicate with each respective local control subsystems to direct necessary adjustments to local processes for a global result.

The control system of the present invention may use any of the above architectures, or any other architecture commonly known in the art, which are considered to be within the general scope and nature of the present disclosure. For instance, processes controlled and implemented within the context of the present invention may be controlled in a dedicated local environment, with optional external communication to any central and/or remote control system used for related upstream or downstream processes, when applicable. Alternatively, the control system may comprise a sub-component of a regional an/or global control system designed to cooperatively control a regional and/or global process. For instance, a modular control system may be designed such that control modules interactively control various sub-components of a system, while providing for inter-modular communications as needed for regional and/or global control.

The control system generally comprises one or more central, networked and/or distributed processors, one or more inputs for receiving current sensed characteristics from the various sensing elements, and one or more outputs for communicating new or updated control parameters to the various response elements. The one or more computing platforms of the control system may also comprise one or more local and/or remote computer readable media (e.g. ROM, RAM, removable media, local and/or network access media, etc.) for storing therein various predetermined and/or readjusted control parameters, set or preferred system and process characteristic operating ranges, system monitoring and control software, operational data, and the like. Optionally, the computing platforms may also have access, either directly or via various data storage devices, to process simulation data and/or system parameter optimization and modeling means. Also, the computing platforms may be equipped with one or more optional graphical user interfaces and input peripherals for providing managerial access to the control system (system upgrades, maintenance, modification, adaptation to new system modules and/or equipment, etc.), as well as various optional output peripherals for communicating data and information with external sources (e.g. modem, network connection, printer, etc.).

The processing system and any one of the sub-processing systems can comprise exclusively hardware or any combination of hardware and software. Any of the sub-processing systems can comprise any combination of none or more proportional (P), integral (I) or differential (D) controllers, for example, a P-controller, an I-controller, a PI-controller, a PD controller, a PID controller etc. It will be apparent to a person skilled in the art that the ideal choice of combinations of P, I, and D controllers depends on the dynamics and delay time of the part of the reaction process of the gasification system and the range of operating conditions that the combination is intended to control, and the dynamics and delay time of the combination controller. It will be apparent to a person skilled in the art that these combinations can be implemented in an analog hardwired form which can continuously monitor, via sensing elements, the value of a characteristic and compare it with a specified value to influence a respective control element to make an adequate adjustment, via response elements, to reduce the difference between the observed and the specified value. It will further be apparent to a person skilled in the art that the combinations can be implemented in a mixed digital hardware software environment. Relevant effects of the additionally discretionary sampling, data acquisition, and digital processing are well known to a person skilled in the art. P, I, D combination control can be implemented in feed forward and feedback control schemes.

In corrective, or feedback, control the value of a control parameter or control variable, monitored via an appropriate sensing element, is compared to a specified value or range. A control signal is determined based on the deviation between the two values and provided to a control element in order to reduce the deviation. It will be appreciated that a conventional feedback or responsive control system may further be adapted to comprise an adaptive and/or predictive component, wherein response to a given condition may be tailored in accordance with modeled and/or previously monitored reactions to provide a reactive response to a sensed characteristic while limiting potential overshoots in compensatory action. For instance, acquired and/or historical data provided for a given system configuration may be used cooperatively to adjust a response to a system and/or process characteristic being sensed to be within a given range from an optimal value for which previous responses have been monitored and adjusted to provide a desired result. Such adaptive and/or predictive control schemes are well known in the art, and as such, are not considered to depart from the general scope and nature of the present disclosure.

2) Gas Inlet Mechanism and Upstream Components

Inlet means comprising of one or more conduits is used to carry the gas from the gasification system to the homogenization chamber. As noted above, the upstream components of the system may optionally include one or more chillers, gas/liquid separators, induced draft devices, gas monitoring systems, which may include temperature and pressure controllers, and control valves.

Conduits

The gas is transferred from the gasification system to the homogenization chamber of the invention by way of conduits that are designed to carry the gas at predetermined temperatures and pressures. One skilled in the art will appreciate that these conduits can take the form of tubes, pipes, hoses, or the like.

With reference to FIG. 1, and in accordance with one embodiment of the invention, the gas is transferred to a single homogenization chamber using a single conduit leading from a single gasification system. With reference to FIGS. 4 & 5, and in accordance with embodiments of the invention, the gas can also be transferred using multiple conduits leading from one or more gasification systems simultaneously to one or more homogenization chambers. In one embodiment of the invention, multiple gas conduits deliver gas from multiple gasification systems to multiple homogenization chambers.

Chiller and Gas/Liquid Separator

One skilled in the art would appreciate when it would be required to incorporate one or more chillers and/or one or more gas/liquid separators into the gas homogenization system described herein. Chiller systems are well known in the art and include, but are not limited to, shell and tube or plate and frame heat exchangers or other temperature modification devices. These systems may employ various cooling fluids, such as, cooling water, chilled water, and/or other suitable fluids. Gas/liquid separators are also well known in the art, such as the reservoir-type separator illustrated in FIG. 13.

Induced Draft Device

Figure 14A:
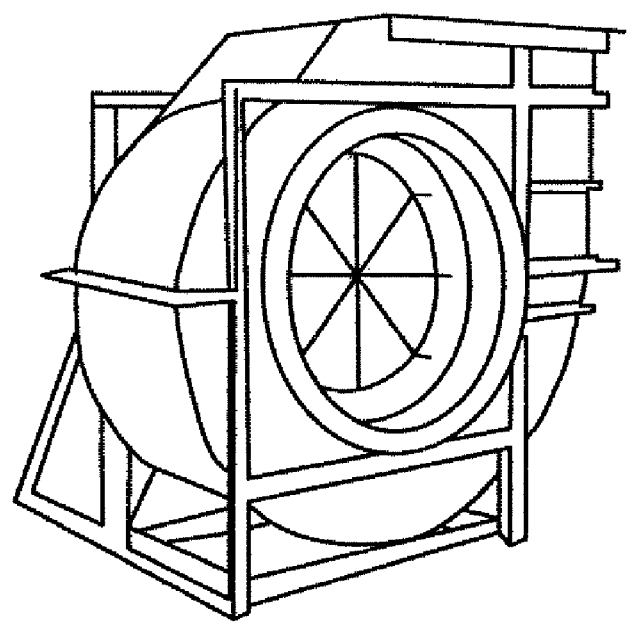
FIG. 14A illustrates a draft induction device configured as a pressure blower, in accordance with one embodiment of the invention.
Figure 14B:
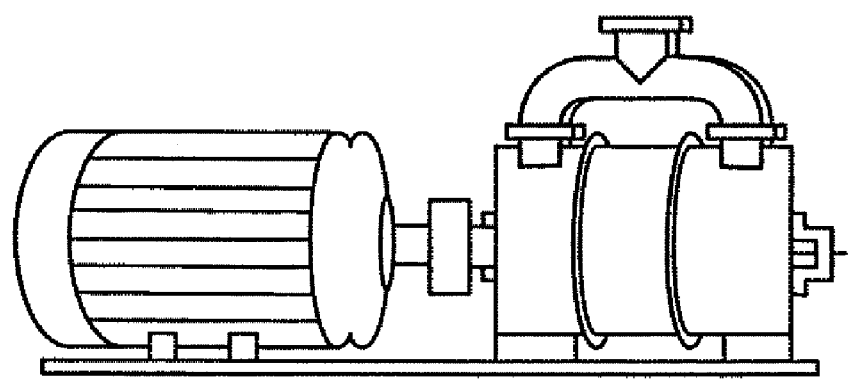
FIG. 14B illustrates a draft induction device configured as a vacuum pump, in accordance with one embodiment of the invention.

As the gas is typically extracted from the gasification system as it is generated, the gas flow is typically non-uniform. When the gasification system is operating at less than atmospheric pressure, an induced draft device may convey the gas through the homogenization chamber. The induced draft device may be located anywhere preceding the homogenization chamber. As would be understood in the field, suitable draft devices include, but are not limited to blower fans and vacuum pumps, or other suitable flow inducing devices. In one embodiment, a pressure blower such as the one in FIG. 14A, functions similar to a centrifugal pump in that the blades of the blower suck air into the middle of the blower and expel air in a radial direction at increased pressure. In another embodiment, the vacuum pump shown in FIG. 14B is designed similar to a blower, but it can operate only when the upstream pressure is substantially a vacuum.

Gas Monitoring System Preceding the Homogenization Chamber

As discussed above, the gas characteristics of the input gas may be monitored within the homogenization chamber or prior to input. In one embodiment, the monitoring system may be part of the inlet means and may comprise automated equipment, such as one or more sensing elements, capable of providing a detailed assessment of the characteristics of the gas. For example, these characteristics can include continuous gas pressure and temperature monitoring plus continuous product gas flow rate and composition monitoring. A worker skilled in the art would readily understand the sampling devices required to collect the above information regarding the gas. For example, temperature can be measured using a thermocouple, or other temperature sensor format; pressure can be measured using an absolute pressure sensor, a gauge pressure sensor, vacuum pressure sensor, differential pressure sensor or other pressure sensor; flow rate can be measured using a flowmeter or other flow rate sensor; gas composition can be measured using a gas composition sensor based on acoustic properties, or other gas composition sensor as would be readily understood.

In one embodiment, a particular sensing element can be configured to measure multiple characteristics of the gas, wherein these types of sensing elements would be readily understood by a worker skilled in the art.

Furthermore, in one embodiment, the monitoring system may include a means for the analysis of gas operatively connected with a feedback system as an integrated, on-line part of a process control system (see section on Control System provided above). The advantages provided by such an integrated on-line gas analysis are finer tuning capabilities of process control and enhanced control and homogenization capabilities for a variety of applications of the gas.

The gas monitoring system comprises sensing element for monitoring gas characteristics thereby determining when characteristics such as gas composition, flow rate, pressure or temperature require adjustment. Different types of such sensing elements are readily available commercially and include, but are not limited, flow meters, thermocouples, velocity meters, pyrometers, gas sensors, gas analyzers, or other detecting and measuring devices.

In one embodiment, for example, once the need to adjust a characteristic, such as, gas pressure is detected, a signal is sent to a response element to adjust a flow valve, which results in a decrease or increase in gas flow rate into the homogenization chamber. Different types of signaling means for generation and transmission of the signal to a response element can be used. For example, the signal can be transmitted using radio transmission, IR transmission, Bluetooth transmission, wired or wireless transmission or other transmission technique as would be readily understood.

In one embodiment of the invention, a controller is operatively coupled to one or more sensing element and response elements associated with gas sampling prior to reaching the homogenization chamber in order to determine control instructions for modification of one or more parameters associated with gas generation. For example a controller can comprise one or more of a variety of types of computing devices, computers, microprocessors, microcontrollers or other computing device format which includes a central processing units (CPU) and peripheral input/output devices to monitor parameters from peripheral devices that are operatively coupled to the controller. For example the peripheral devices can include the one or more sensing elements and/or one or more response elements. These input/output devices can also permit the CPU to communicate and control peripheral devices that are operatively coupled to the controller. The controller can be operatively coupled to a memory device. For example, the memory device can be integrated into the controller or it can be a memory device connected to the computing device via a suitable communication link. The memory device can be configured as an electronically erasable programmable read only memory (EEPROM), electronically programmable read only memory (EPROM), non-volatile random access memory (NVRAM), read-only memory (ROM), programmable read-only memory (PROM), flash memory or any other non-volatile memory for storing data. The memory can be used to store data and control instructions, for example, program code, software, microcode or firmware, for monitoring or controlling the one or more sensing elements which are associated with the homogenization chamber and are coupled to the controller and which can be provided for execution or processing by the CPU. Optionally, the controller also provides a means of converting user-specified operating conditions into control signals to control the response elements coupled to the controller. The controller can receive user-specified commands by way of a user interface, for example, a keyboard, a touchpad, a touch screen, a console, a visual or acoustic input device as is well known to those skilled in this art.

The gas monitoring system is used to control regulated gas production such that it satisfies the general standards of downstream applications. If it does not, the appropriate adjustments can be made to the gasification process to bring the gas into compliance. Alternatively, or in conjunction with the gas monitoring equipment, the gas inlet means may comprise a diverter outlet for releasing non-compliant gas, i.e., gas which does not meet the requirements for the downstream application. In this way, non-compliant gas will be disposed of through, for example, a diverter which may lead the non-compliant gas to a combustor or incinerator, for example, a flare stack as illustrated at FIGS. 1-5. Accordingly, in the event that gas composition diverges excessively from the requirements of a downstream application, gas can be diverted. In one embodiment, the inlet means of the invention includes gas monitoring equipment. In one embodiment, the inlet means includes gas monitoring equipment that functions in cooperation with a diverter.

Pressure Control System

In some embodiments of the invention, the gas inlet means may further comprise a mechanism for controlling the flow rate of the gas into the homogenization chamber, thus controlling the pressure of the gas in the chamber. This pressure control subsystem may comprise conventional valves or shut off systems known in the art. Several non-limiting examples of pressure regulating devices are shown for example in FIGS. 16A-D. The pressure control system responds to signals from the monitoring system and may control the flow rate of the gas as well as direct the gas appropriately. In one embodiment, the pressure control system includes a valve by which compliant and non-compliant gas can be directed to the homogenization chamber and combustor or incinerator or can be relayed to the gasifier of the gasification system, respectively.

As would be understood by the skilled worker, suitable valves for controlling the flow of gas are desirable. FIGS. 17A-D and FIG. 18, provide non-limiting examples of flow regulating devices and control valves, respectively. Such flow regulating devices and valves may increase or reduce the gas flow rate by at least about 10% to about 100%. As noted above, gas flow rate is monitored and adjusted via a controller. For example, in one embodiment of the invention, if the pressure in the system increases to 100%, the pressure control mechanism can send a signal to the gas blower to adjust the blower's revolutions-per-minute (RPM) as required in order to reduce this pressure.

Pressure transmitter mounting and bracketing devices for use with the gas homogenization system are also herein contemplated and are readily available commercially. Non-limiting examples of such are provided at FIG. 19A-K).

3) Regulated Gas Outlet Mechanism and Downstream Components

The gas homogenization system also comprises an outlet means for transferring the regulated gas from the homogenization chamber to downstream applications (e.g., gas engines or gas turbines). The outlet means comprises one or more conduits to carry the regulated gas from the homogenization chamber to downstream applications. The system may optionally include a gas monitoring system, which may include temperature and pressure control mechanisms.

Outlet Conduits

The regulated gas is transferred from the homogenization chamber to the downstream application by way of regulated gas conduits that are designed to carry the gas at predetermined temperatures and pressures. One skilled in the art will appreciate that these conduits can take the form of tubes, pipes, hoses, or the like.

With reference to FIG. 1, and in accordance with one embodiment of the invention, the regulated gas is transferred from a single homogenization chamber using a single conduit to a downstream application. With reference to FIGS. 2, 3 & 4, and in accordance with other embodiments of the invention, the regulated gas can also be transferred using multiple conduits from a single homogenization chamber to multiple downstream applications.

In one embodiment of the invention, multiple homogenization chambers each with a corresponding conduit deliver regulated gas to a common downstream application simultaneously. In one embodiment of the invention, the outlet means includes multiple regulated gas conduits delivering regulated gas from multiple homogenization chambers to multiple downstream applications.

The recycling of regulated gas is also herein contemplated. Regulated gas derived from the homogenization chamber, for example, may be directed to re-enter the system at various suitable upstream location of a complete gasification system, via the use of appropriate conduit systems, as would be readily understood.

Gas Monitoring System

As already discussed, a monitoring system is used to monitor/control the gas either prior to its entry into the homogenization chamber or during its residence in the homogenization chamber. Similarly, a monitoring system can be used to monitor the regulated gas before it is delivered for the downstream application. This can serve to confirm and control the characteristics To this end, the regulated gas outlet means may optionally further comprise one or more sensing elements, response elements and/or control devices which monitor and/or regulate all or some of the characteristics of the regulated gas (i.e., composition, pressure, flow rate, and temperature). A controller, for example, may act through a feedback loop in which the regulated gas is analyzed in real-time and the relevant adjustments made to the system. In one embodiment of the invention, the sensing elements analyze the pressure and flow rate of the regulated gas, and from the data analysed via a controller, a signal is transmitted to slow down the flow of regulated gas or flare the excess gas out of the homogenization chamber. In one embodiment, the sensing elements analyze the temperature of the regulated gas and a controller sends a signal to a heater and/or a chiller to adjust the temperature of the regulated gas to a temperature suitable for the downstream application.

As discussed above the gas monitoring system can comprises one or more controllers associated therewith. In one embodiment a controller is associated with the gas monitoring system which evaluates the gas within the homogenization chamber and another controller is associated with the gas monitoring system which evaluates the gas prior to reaching the homogenization chamber. In this configuration the two controllers can operate independently and can provide instructions to the one or more response elements to which they are connected in order to alter the conditions of the gas at either of the locations being monitored. In one embodiment, these two controllers are operating in a slave configuration, wherein a master controller is operatively coupled to these two controllers and the master controller provides instructions to the two controllers in order to enable a more efficient and streamlines adjustment of the characteristics of the gas at the monitored locations.

In one embodiment of the invention, the gas monitoring system comprises a single controller which is operatively coupled to the one or more sensing elements and response elements associated with the with the gas monitoring system which evaluates the gas within the homogenization chamber and the gas monitoring system which evaluates the gas prior to reaching the homogenization chamber. This configuration can also provide a means for efficient and streamlines adjustment of the characteristics of the gas at the monitored locations, however in this single controller configuration, operative connection with the sensing elements and response elements may be more complex, when compared with a master controller and slave controllers configuration.

Flow and Pressure Regulation

The regulated gas outlet means may further comprise a means for controlling the flow rate of the regulated gas from the homogenization chamber and to a downstream application. Working alternately to, or in conjunction with, the control system operative in the inlet means, the pressure of the homogenization chamber may be controlled. The pressure control in the outlet means may comprise conventional valves or shut off systems known in the art. As discussed above, the flow and pressure control system responds to signals from the monitoring system employed to monitor the characteristics of the regulated gas as it exits the homogenization chamber. For example, the control system may comprise a pressure regulator valve that may be adjusted to control gas flow rate and pressure by way of one or more response elements.

Heater and Gas/Liquid Separator

The regulated gas outlet means may further comprise a means for heating the regulated gas as it exits the homogenization chamber. One skilled in the art would also appreciate when it is advantageous to incorporate a gas/liquid separator into the system of the invention.

Figure 13:
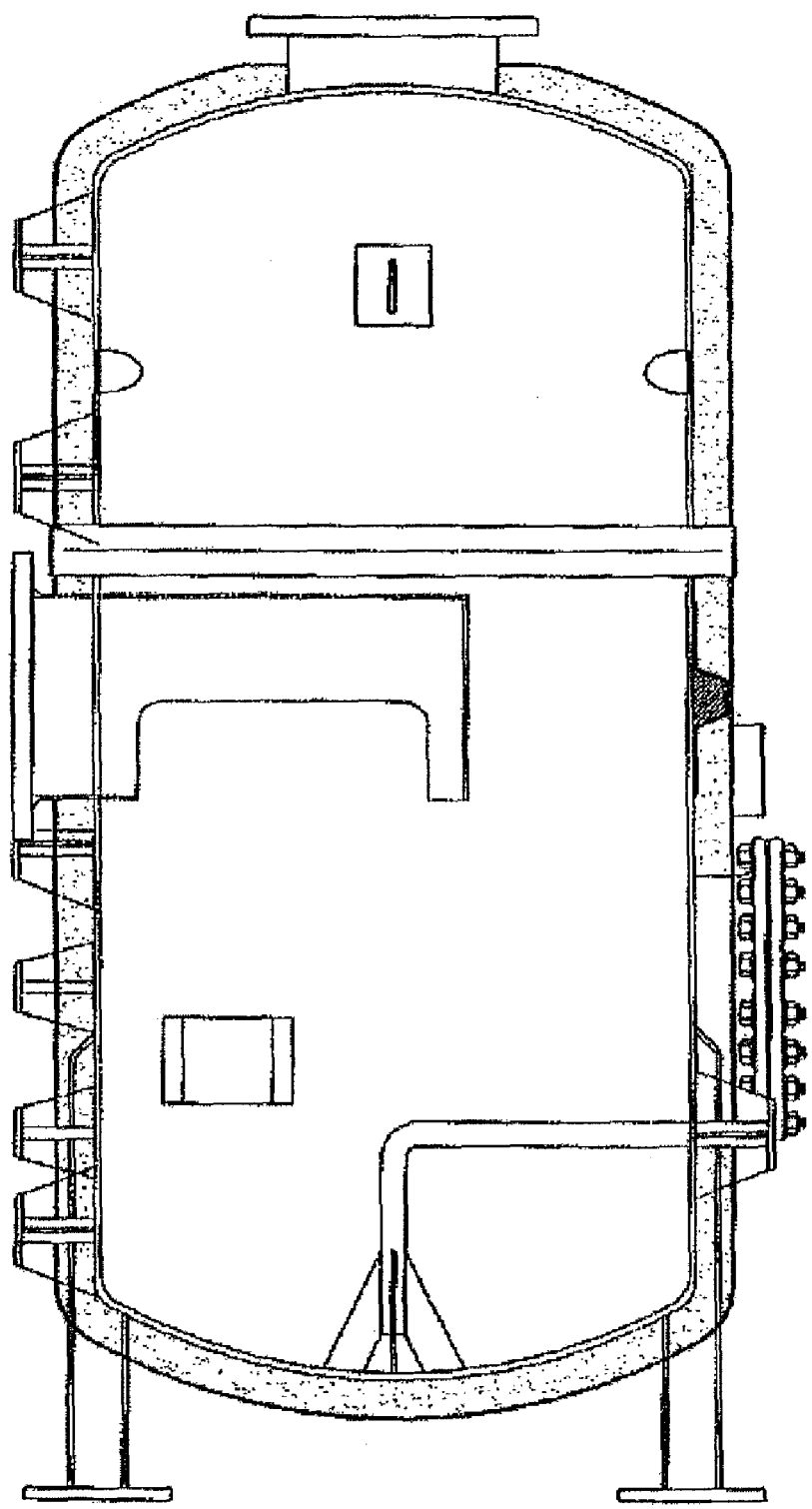
FIG. 13 is an illustration of a gas/liquid separator, in accordance with one embodiment of the invention.

The operational requirements of a downstream application regarding gas temperature and humidity will determine the target temperature that the regulated gas must meet prior to transfer to the downstream application. For example, a gas engine will typically require a temperature of no more than about 40° C. and a relative humidity of no more than about 80% in order to operate efficiently. FIG. 13 provides an illustration of one embodiment of a reservoir-type gas/liquid separator. Non-limiting examples of heaters for use with the system include shell and tube, electric, glycol water heaters or the like. A person skilled in the art will appreciate that the heaters and separators that may be employed with the system are readily available commercially.

Filter

Typically downstream applications such as gas engines and gas turbines are sensitive to trace elements that may enter the gas during any point of the gas production process. In this regard, the system may comprise one or more filters of an appropriate pore size to screen out these potentially interfering contaminants, while substantially limiting the impact that the filter has on gas flow rate. In one embodiment, a filter is associated with the common header to the engines. In one embodiment, each engine gas train has its own filter.

In one embodiment, both of the above-mentioned filtering approaches are used and may be configured as a two stage filtering process.

Pressure Regulating Valves

The regulated gas outlet device may further comprise pressure regulating valve device for controlling the pressure of the regulated gas prior to delivery to the downstream application.

Gas Compressor

One skilled in the art will appreciate that a downstream application will dictate the specific gas characteristics required for the regulated gas. For example, the required gas pressure for the efficient operation of a gas engine will differ from those of a gas turbine. As discussed above, a gas turbine will require a relatively high gas pressure. It is contemplated, therefore, that in those embodiments requiring a high gas pressure, a means for gas pressurization can be included in the homogenization system. Gas pressurization devices are well known in the art and may include a gas compressor of a variety of designs such as axial-flow compressor, reciprocating compressor, rotary screw compressor, centrifugal compressor shown in FIGS. 20 A, B, C, D & E respectively. Other implementations include the diagonal or mixed-flow compressor, the scroll compressor, or other gas pressurization devices, as would be known to a worker skilled in the art.

4) Emergency Exit Port with Control Valve

Figure 21A:
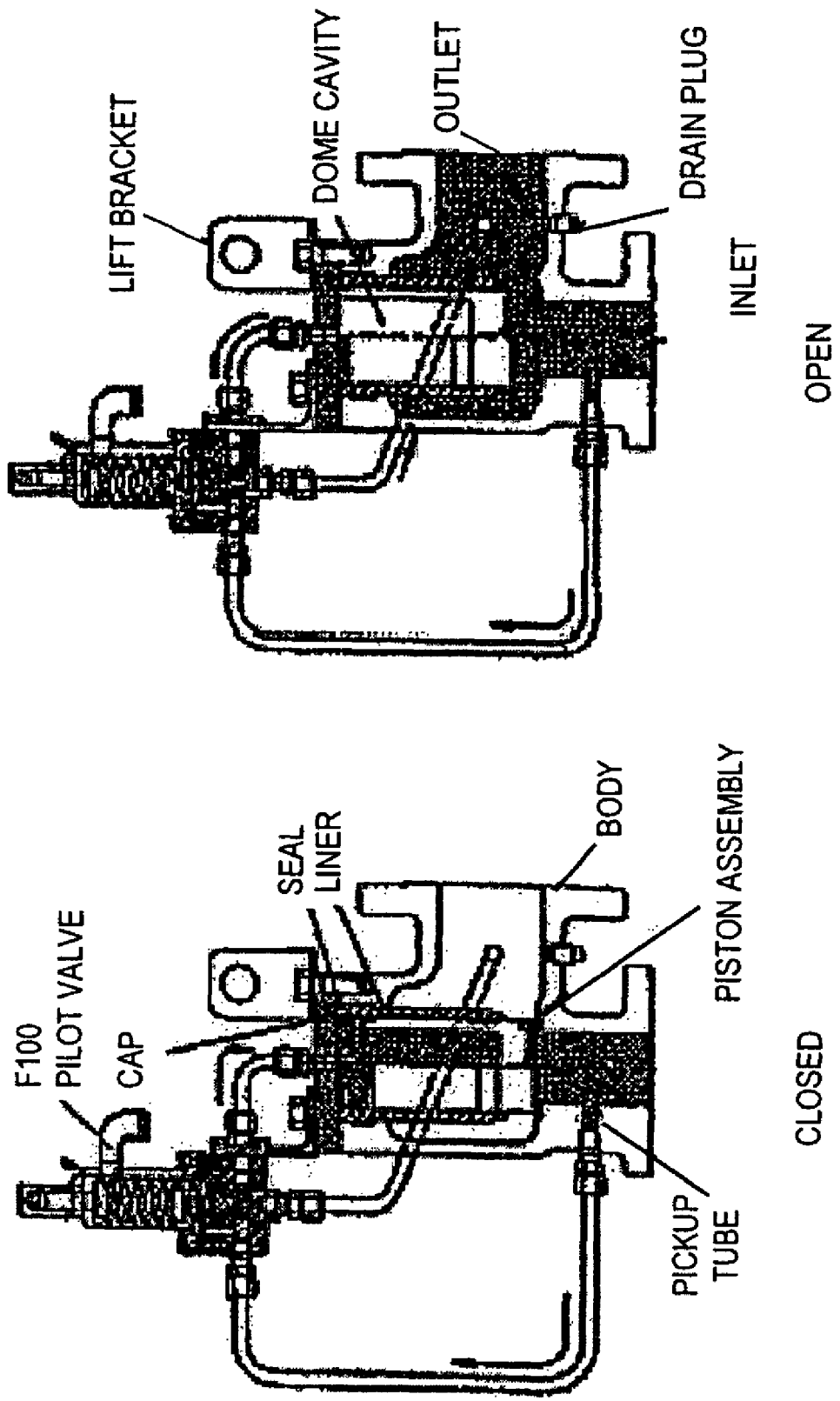
FIG. 21A illustrates relief valve mechanisms of 1.5"×2" through 3"×4, in accordance with embodiments of the invention.
Figure 21B:
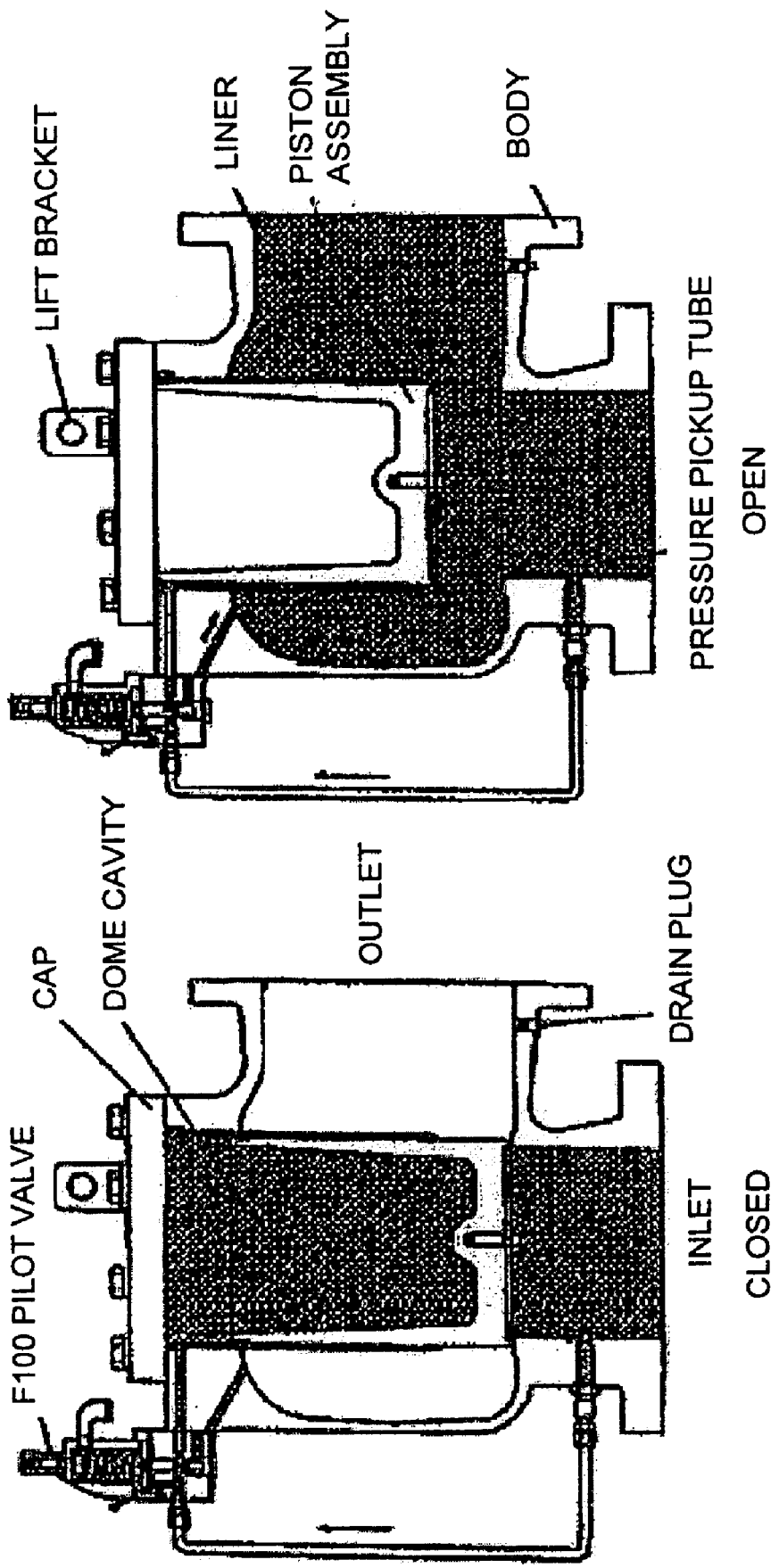
FIG. 21B illustrates relief valve mechanisms of 4"×6" through 12"×16", in accordance with embodiments of the invention.

The pressure control system may additionally comprise one or more emergency exit ports with control valves. When gas flow cannot be reduced fast enough, for instance due to an up-stream operational malfunction, or a downstream failure of a gas engine, an emergency control valve may be opened to release gas through an emergency exit port. Two non-limiting examples of relief valves are shown in FIGS. 21A and B, respectively.

The emergency valve may be opened rapidly so that no significant change (about <1%) in gas pressure may occur. One skilled in the art will appreciate that the emergency exit port and corresponding valve may be located at any point in the homogenization system of the invention. In one embodiment, the emergency port is located in the homogenization chamber. In one embodiment, the emergency port is located in the inlet means. In one embodiment, the emergency port is located in the outlet means.

Assembly of Gas Homogenization System

The assembly of a gas homogenization system may require the provision of various fastening means, connector means, bracketing and/or lifting means, foundation and/or anchoring means, grounding lug means, etc. A person skilled in the art will appreciate that such means are readily available commercially and their installation well understood.

Downstream Applications

The system according to the invention is configured to generate a regulated gas which is substantially a continual and steady stream of gas having defined characteristics. This regulated gas is delivered to one or more downstream applications for subsequent use thereof by these one or more downstream applications. For example a downstream application can be a gas turbine, combustion engine or other suitable application which requires a regulated gas for operation thereof.

Combustion Turbine Engine

In one embodiment of the invention, a downstream application is a combustion turbine engine which combines $O_2$ with CO and $H_2$ to generate $CO_2$, $H_2O$ and energy, wherein the energy is in the form of heat and pressure. As the gas expands during the combustion process, it expands across a multiple stage power turbine to drive an axial flow air compressor and a generator in order to generate make electricity. The fuel gas, namely the regulated gas, must be pressurized to a sufficient level in order to feed the gas turbine as combustion takes place at a pressure approximately equivalent to the compression ratio of the combustion turbine.

The regulated gas can be delivered to one or more combustion turbine engines, and the regulated gas can be either compressed prior to delivery to an engine or the entire gasification process can operated at a predetermined pressure which is sufficient for delivery of the regulated gas at the required pressure. The pressure of the regulated gas can range from about 100-600 psig depending of the compression ratio of the particular combustion turbine engine.

In one embodiment, before entering the fuel system of the combustion turbine engine, the regulated gas may be further filtered in order to collect any trace quantities of particulate matter that may have been picked up in the processing equipment and piping associated with the system.

In one embodiment, a pre-heating system can be employed to pre-heat the cooled and compressed fuel gas if desired. A pre-heating system can be configured to use waste heat from a gas cooling system located at an alternate location within the system. For example, the waste heat can be extracted from upstream in the system for example when the gas is cooled after leaving the gasification process. The waste heat may also be extracted from downstream in the system and may be recovered from the turbines. In one embodiment, the waste heat is extracted from both upstream and downstream of the system.

In one embodiment, pre-heating of the regulated gas may be useful where the gas cooling system cools the regulated gas to a temperature required by a scrubber, and that temperature is below a desirable temperature for the cleaned regulated gas which is the fuel gas to be introduced into the combustion chamber of the combustion turbine engine. In one embodiment, steam injection can be used in association with some combustion turbines engines in order to control NOx formation and this configuration may constitute an alternate to dry emission technology.

Internal Combustion Engine

In one embodiment of the invention, a downstream application is an internal combustion engine. An internal combustion engine can produce energy using a process similar to that discussed above except that the compressor, combustor and gas turbine are replaced by an internal combustion engine. An internal combustion engine may be easier to utilize and may be more cost efficient than a turbine, especially for small-scale gasification electro-conversion units. Air and auxiliary fuel may be fed to the internal combustion engine in a predetermined manner based on the composition of fuel gas, namely the regulated gas.

Environmentally attractive low emission internal combustion engine-generator systems for gasification systems can be provided to greatly improve efficiency and pollution reduction. For example, spark ignition internal combustion engines are advantageous in that such engines are less expensive for very small units and are easier to start and stop than turbines.

In one embodiment of the invention, in order to facilitate production of a desired level of electrical power, particularly during startup, an auxiliary fuel may be used to power the internal combustion engine, wherein this auxiliary fuel may be a hydrogen-rich gas, propane, natural gas, diesel fuel or the like. The amount of auxiliary fuel required may vary depending on the lower heating value of the carbonaceous feedstock being gasified and the power requirements for the overall gasification system, for example.

Fuel Cell Technologies

In one embodiment of the invention, a downstream application is a fuel cell. After removing contaminants, such as PM, HCL and $H_2S$, at relatively high temperatures (SOFC, about 1000° C.; MCFC about 650° C.), the gas from a gasification system can be fed into a gas homogenization system to produce a regulated gas that satisfies the requirements of a high temperature fuel cell (for example, Solid Oxide Fuel Cell (SOFC) or Molten Carbonate Fuel Cells (MCFC)). As stringent contaminant limits may have to be met in order to prevent the degradation of fuel cell performance, the upstream Gas Conditioning System (GCS) configuration may vary to fit the fuel cell operation conditions. The gas and oxidant compositions may also need to be adjusted to optimize the efficiency or output of a high temperature fuel cell.

Molten carbonate fuel cells (MCFC) contain an electrolyte that is a combination of alkali (Li, Na, and K) carbonates stabilized in a $LiAlO_2$ ceramic matrix. Thus, in one embodiment of the invention, the gaseous input fuel mixture includes carbon monoxide, hydrogen, methane, and hydrocarbons, with limits on total hydrocarbons, particulate loading, sulfur (in the form of $H_2S$), ammonia, and halogens (e.g., HCl). At the operating temperature of about 1200° F. (650° C.), the salt mixture is liquid and a good ionic conductor.

The anode process for an MCFC involves a reaction between hydrogen and carbonate ions ($CO_3^-$) from the electrolyte, which produces water and carbon dioxide ($CO_2$), while releasing electrons to the anode. The cathode process combines oxygen and $CO_2$ from the oxidant stream with electrons from the cathode to produce carbonate ions, which enter the electrolyte. If the $CO_2$ content in the fuel gas is insufficient, $CO_2$ can be recycled from the emission stream. In one embodiment of the invention, an MCFC produces excess heat at a temperature which is sufficiently high to be usable in producing high pressure steam that may be fed to a turbine to generate additional electricity. In combined cycle operation (steam turbine powered generation and fuel cell power generation), electrical efficiencies in excess of about 60% are contemplated for mature MCFC systems.

A solid oxide fuel cell (SOFC) uses a hard ceramic electrolyte instead of a liquid and operates at temperatures up to about 1,000° C. (about 1,800° F.). In this type of fuel cell, a mixture of zirconium oxide and calcium oxide forms a crystal lattice, although other oxide combinations have also been used as electrolytes. The solid electrolyte is coated on both sides with specialized porous electrode materials. At a relatively high operating temperature, oxygen ions (with a negative charge) migrate through the crystal lattice.

The fuel gas containing hydrogen and carbon monoxide is passed over the anode while a flow of negatively charged oxygen ions moves across the electrolyte to oxidize the fuel. The oxygen is supplied, usually from air, at the cathode. Electrons generated at the anode travel through an external load to the cathode, completing the circuit that carries the electrical current.

In one embodiment of the invention, generating efficiencies can range up to about 60 percent. Like molten carbonate fuel cells, solid oxide cells may require high operating temperatures that provide the opportunity for "co-generation," i.e., a combined heat and power application using waste heat to generate steam for space heating and cooling, industrial processing, or for use in driving a steam turbine to generate more electricity.

A (high-temperature) fuel cell would consume the hydrogen and (primarily in SOFCs) and carbon monoxide from the gas provided by the system. Methane contained in the fuel gas would be partially reformed in a high-temperature fuel cell, resulting again in hydrogen and carbon monoxide. The gas mixture exiting the fuel cell would likely still include useful quantities of methane and carbon monoxide gases. These hot gases could be directed into the homogenization system of this invention or diverted to more heat exchangers, which could be used for the production of steam that is used in a reaction vessel.

Alternatively, and according to one embodiment of the invention, hot but cleansed gas can be input to a high temperature hydrogen membrane filtering system to split the synthesis gas into two distinct gas streams. One stream is composed of pure hydrogen and the other of pure carbon monoxide (CO). In one embodiment of the invention, carbon monoxide can either be combusted in a gas-fired boiler to facilitate the recovery of carbon dioxide ($CO_2$) and the conversion of its potential energy in steam, or it can be transported to a compressor and bottled. In one embodiment of the invention, the hydrogen ($H_2$) can either be converted into energy in fuel cells or it can be transported to a compressor and then fed into containers holding either/or a graphite nano-fiber storage medium or an anhydrous aluminum storage medium, so that the $H_2$ can be safely stored or transported.

In one embodiment of the invention, the hydrogen feed line can be provided from the high temperature hydrogen membrane filtering system, to fuel cell stacks as a fuel supply to them. Fuel cell stacks of this system are typically of the molten carbonate types that use hydrogen gas at the anode and $CO_2$ at the cathode to produce electricity. The carbon monoxide present in the gas produces extra hydrogen as well as heat (up to about 1500° F.) which can be recovered to produce steam, carbon dioxide and water.

A carbon monoxide line may be provided to direct carbon monoxide from the high temperature hydrogen membrane filtering system to a conventional gas-fired boiler. The gas fired boiler combusts the CO so that $CO_2$ and the potential energy value of the CO manufactured by the gasification system may be recovered more cost effectively.

Some upstream gasification systems will be designed for the input of more than one fuel or feedstock into the boiler, thereby providing versatility for increased amounts of power generation as required or desirable. Non-limiting examples of additional fuel sources include natural gas, as well as the gases obtained from the anaerobic digestion of organic wastes (also referred to as biogas).

As would be apparent to those of skill in the art, depending on the specific electric power generating device selected, it may be beneficial to include other types of fuel, in addition to the gas generated in the gasification system, to maximize the efficiency of the electrical generator. Such optional additional fuels, can include natural gas, oil, and other conventional hydrocarbon-based fuels. It should be noted that the optional fuels are not intended to provide the majority of the BTUs or energy consumed by the electrical generators, but instead are included only when they can enhance the overall efficiency of the system. Thus, additional fuels are typically not required for use with the system.

An alternative configuration, in accordance with one embodiment of the invention, employs a gasification system that allows for the use of molten carbonate fuel cells, together with the production of $CO_2$ and $H_2O$ with greatly reduced emissions of oxides of nitrogen, carbon monoxide or unburned hydrocarbons. Here, carbon monoxide is fed, along with hydrogen, to fuel cells. These fuel cells may be molten carbonate or other types of fuel cells, which consume the carbon monoxide as a valuable fuel.

In one embodiment of the invention, the downstream application includes proton exchange membrane fuel cell (PEMFC) stacks employing cooled pure hydrogen. As in other fuel cells, the chemical energy of the fuel is directly transformed into electricity. Electricity is generated via the following electrochemical reactions:

Anode: $2H_2 \Rightarrow 4H^+ + 4e^-$

Cathode: $O_2 + 4H^+ + 4e^- \Rightarrow 2H_2O$

These reactions typically occur at low temperature (for example, <100° C.) and involve splitting hydrogen into electrons and positive charged hydrogen ions (protons) at the platinum catalytic layer of the anode, passing protons through the proton exchange membrane (electrolyte) and their electrochemical oxidation at the cathode catalyst. If the electrolyte (solid polymer membrane) is saturated with water, a careful control of the moisture of the anode and cathode streams is required. Moreover, low quantities of CO (for example, levels higher than about 1 ppm) and $H_2S$ poison catalyst on the anode may affect hydrogen purity requirements.

As would be apparent to a worker skilled in the art, PEMFCs typically generate more power for a given volume and weight than other types of fuel cells and additionally allow for a rapid start-up. Thus, in accordance with one embodiment of the invention, the contemporary efficiency of the PEMFC stacks reach values of about 35-45%.

In one embodiment, a system is configured to allow the use of hydrogen gas to drive turbines to generate electricity. This is possible without damage to critical internal components from the high combustion temperature of synthesis gas and results in greatly reduced emissions of oxides of nitrogen. In one embodiment, the hydrogen from the high temperature hydrogen membrane may be input to a fogger water injection system where de-ionized water is added before the combination is burned in a gas turbine or internal combustion engine to convert the energy to mechanical force and drive a generator which provides electricity. Here, water acts to limit the internal temperatures and thereby prevents heat damage to critical internal components. In addition, the fogger water injection system makes it possible to operate this invention in locations and/or at times when such alternative fuels may not be readily available in quantity. In addition, the use of the irrigation fogger may markedly lower nitrous oxide emissions caused by the high temperatures of the combustion of synthesis gas and/or alternative fuel mixes.

Polygeneration

In accordance with the invention, the downstream applications may include polygeneration. Thus, the gas from a gasification system can be fed into a gas homogenization system to produce a regulated gas that satisfies the requirements for polygeneration. Polygeneration involves the co-production of electricity and synthetic fuels, which are described in greater detail below, and may be employed in large scale Integrated Gasification Combined Cycle (IGCC) plants using coal. The potential synthetic fuels generated include ethanol, methanol, di-methyl-ether (DME), and Fischer-Tropsch (F-T) liquids (diesel, gasoline).

i) Co-Production of Electricity and Methanol

In one embodiment of the invention, a system based on gas derived from a gasification system allows for the co-production of electricity and methanol, which can be used either as a chemical feedstock or as an energy carrier. As an energy carrier, methanol has a number of potential applications.

Methanol (MeOH) is potentially a cleaner alternative fuel for the future. One attractive possibility is its use in fuel cells for mobile applications. Methanol can be easily reformed into hydrogen and is more easily stored and transported than hydrogen.

Figure 22:
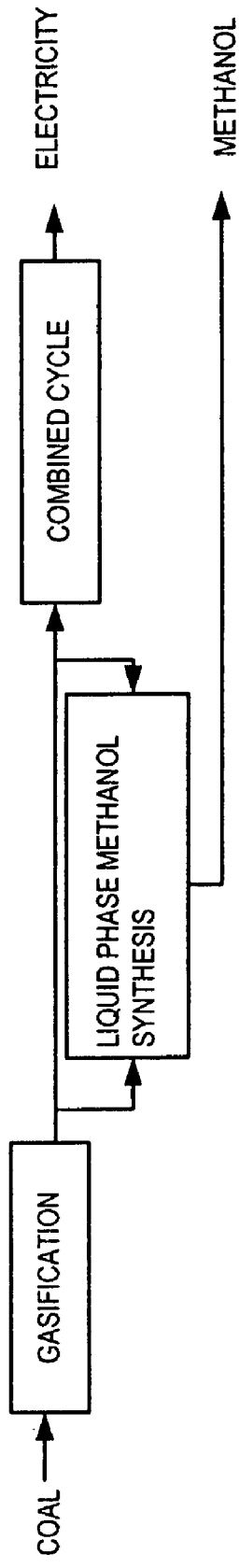
FIG. 22 is a flow diagram of an integrated system combining an Integrated Gasification Combined Cycle (IGCC) power plant and a Liquid Phase Methanol Process (LP-MeOHe) reactor, in accordance with one embodiment of the invention.

In one embodiment of the invention, a system configuration combining the Liquid Phase Methanol Process (LP-MeOHe), and an IGCC power plant is herein contemplated. Typically this system can reach higher synthesis gas conversion levels in a single pass through the reactor and has lower purification costs than a conventional gas phase methanol production technology. In addition, such a system can allow for the production of high-quality methanol from a wider range of gas compositions and specifically from gas mixtures rich in carbon monoxide. In accordance with one embodiment of the invention, FIG. 22 presents the process flow diagram of a methanol/electricity co-production system.

ii) Co-Production of Electricity and Isobutanol

The demand for methyl-t-butyl ether (MTBE) and other tertiary alkyl ethers as gasoline additives has attracted attention to alternative pathways for their production. In one embodiment of the invention, a system for the synthesis of isobutanol-methanol mixtures via CO hydrogenation is contemplated. In one embodiment, the isobutanol/methanol mixture formed in isobutanol synthesis can also react jointly over a catalyst to yield MTBE.

iii) Co-Production of Electricity and Hydrocarbons

In accordance with one embodiment of the invention, a gasification plant can co-produce electricity and Fischer-Tropsch (F-T) fuel liquids. The direct processing of the gas in the F-T reaction eliminates the need for an additional step (water-gas shift) to increase the $H_2/CO$ ratio. The inherent water-gas shift activity possessed by some catalysts, such as iron F-T catalysts, allows the direct processing of low-$H_2$/CO-ratio synthesis gas. The water-gas shift (WGS) reaction occurs simultaneously with the production of hydrocarbons during F-T reaction over iron-based catalysts. These two reactions are:

$$F\text{-TS: } n CO + 2n H_2 \sim (-CH_2-)_n + n H_2O \quad (1)$$

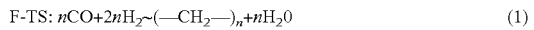

$$WGS: CO + H_2O \sim CO_2 + H_2 \quad (2)$$

The relative extents of the F-T and WGS reactions need to be optimized for the maximum production of hydrocarbons. In one embodiment, the F-T reaction produces a large variety of hydrocarbons ranging from light gases to heavy wax ($>C_{20}$). Among others, clean diesel ($C_{10}$-$C_{15}$) and gasoline ($C_5$-$C_{12}$) can be obtained, which do not contain sulfur or nitrogen, have very low contents of aromatics and exhibit a high Cetane number, which implies the higher capacity of a fuel to auto-ignite.

Figure 23:
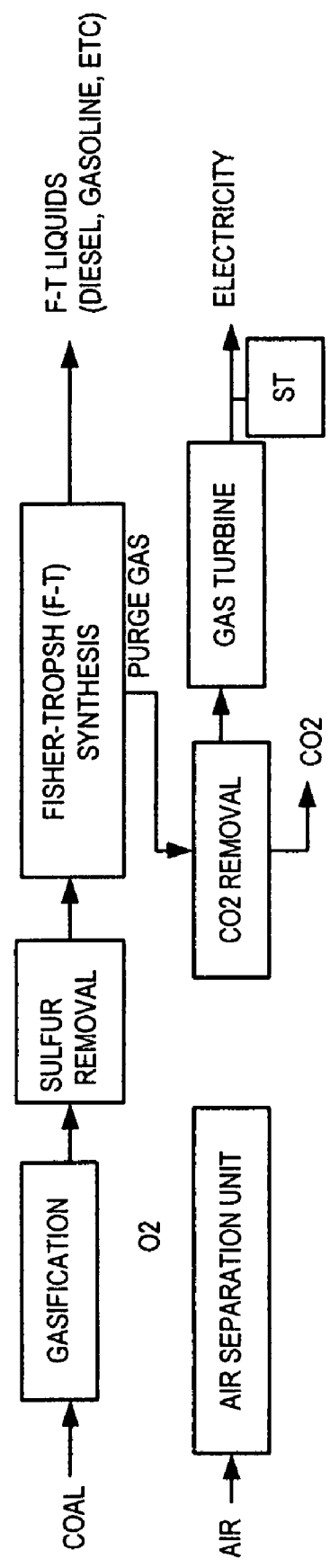
FIG. 23 is a flow diagram of an integrated system, in accordance with one embodiment of the invention, where Integrated Gasification Combined Cycle (IGCC) power plant and Fischer Tropsch (F-T) liquids co-production is used.

In accordance with one embodiment of the invention, FIG. 23 shows an integrated IGCC and F-T liquid co-production system.

Chemical Synthesis

The gas obtained from the gasification of carbonaceous feedstock is also a rich source of chemicals. In accordance with one embodiment of the invention, gases can be recombined into liquid fuels, including high-grade transportation fuels, and a range of petrochemicals that, in turn, serve as feedstocks in the chemicals and refining industries. For example, in contrast to conventional combustion, carbon dioxide exits a gasifier in a concentrated stream rather than diluted in a high volume of flue gas. This allows the carbon dioxide to be captured more effectively and then used for commercial purposes or sequestered.

As noted above, synthesis gas can be used as a building block for chemical synthesis as well as a feedstock for the recovery of pure carbon monoxide and hydrogen. The theoretical $CO:H_2$ ratio is 1 for synthesis of hydrogen, 1 for ethanol production, 0.5 for methanol production, and 0.33 for SNG synthesis. The process is very competitive at a ratio of 1 but it can be modified to produce different ratios, usually at a certain increase in cost. A great number of products can be produced. Non-limiting examples of the major products include:

ethanol (direct from $CO/H_2$ or from methanol)
mixed alcohols (direct from $CO/H_2$ or from methanol)
methanol
SNG via methylation
paraffins and olefins, diesel and gasoline (Fischer-Tropsch synthesis)
benzene, toluene, and xylene (Mobil process from methanol)
ethylene (Mobil process from methanol)
ethylene (from $CO/H_2$ via modified Fischer-Tropsch process, i.e., Ruhrchemie)
ethylene (from FT paraffins via cracking process)
Hydrogen and carbon monoxide by separation i) Ethanol In accordance with the invention, a process for the synthesis of ethanol from gas is contemplated. In one embodiment of the invention, the process involves the catalytic conversion involving the use of specific catalysts at elevated temperatures. The conversion yields a mixture of ethanol, methanol and other higher alcohols and the target product (ethanol) can be obtained at 95% purity by distillation.

In one embodiment of the invention, the process involves a fermentation conversion that takes place at mild temperatures around 37° C. in the presence of specific bacteria.

$$CO + \tfrac{1}{2} H_2O = \tfrac{1}{6} C_2H_5OH + \tfrac{2}{3} CO_2$$

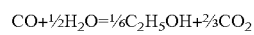

$$H_2 + \tfrac{1}{3} CO_2 = \tfrac{1}{6} C_2H_5OH + \tfrac{1}{2} H_2O$$

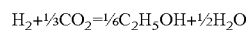

ii) Methanol

In accordance with the invention, a process for the synthesis of methanol from gas is contemplated. In one embodiment of the invention, methanol production from gas involves a catalytic hydrogenation reaction where carbon monoxide and hydrogen react to form methanol. This reaction occurs at 50-100 atm and 250-300° C. for a high selectivity of methanol and is known in the art. The reaction is as follows:

$$CO + 2H_2 \rightarrow CH_3OH$$

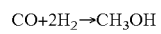

The methanol generated can then be further reacted with CO to produce acetic acid and other derivatives used in the manufacture of a variety of consumer products. In this way, the methanol produced from synthesis gas in turn acts as a valuable feedstock for a variety of other chemicals (e.g., in the manufacture of acetic anhydride, methyl acetate and dimethyl terephthalate). The gases processed by the invention may also be used in the plastics and fertilizer industries.

Methanol is a clean-burning liquid that can be used to power electricity-generating turbines as well as a fuel for automobiles and other vehicles.

iii) Hydrogen

In accordance with the invention, a process for the synthesis of hydrogen from gas is contemplated. In one embodiment of the invention, Hydrogen can be derived commercially from gas in two steps. The synthesis gas is first converted catalytically according to the following equation: $CO + H_2O = CO_2 + H_2$. The second step purifies the hydrogen produced from the first step by low temperature separation, pressure-swing adsorption, or diffusion.

iv) Carbon Monoxide

In accordance with the invention, a process for the synthesis of carbon monoxide from gas is contemplated. In one embodiment of the invention, carbon monoxide can be derived commercially from gas using a separation process. The separation process can be based on condensation and distillation of carbon monoxide in the liquid phase at low temperature or on selective absorption of carbon monoxide.

v) Methane (Substitute Natural Gas or SNG)

In accordance with the invention, a process for the synthesis of methane from gas is contemplated. In one embodiment of the invention, gas can be hydrogenated to methane ($CO+3H_2=CH_4+H_2O$) in the presence of specific catalysts. The conversion can be carried out in a fluidized bed or a liquid-phase process. The catalysts used in the conversion are normally highly selective towards methane and only small amounts of higher hydrocarbons are formed.

vi) Hydrocarbons—Fischer-Tropsch Synthesis

In accordance with the invention, a process for the synthesis of hydrocarbons from gas is contemplated. In one embodiment of the invention, the catalytic hydrogenation of carbon monoxide with catalysts containing iron, cobalt, or ruthenium produces hydrocarbons. The Fischer-Tropsch (F-T) synthesis can provide a wide variety of hydrocarbons ranging from methane to gasoline to diesel to waxes.

F-T technology is a well known art in the chemical and refining industries, most notably to produce gasoline and diesel fuel from gas produced by coal gasification. The process design differences among F-T products are primarily a result of changes to process pressure, temperature and use of custom catalysts, to adjust chemical reactions and produce the desired product.

Typically, it is not possible for the F-T catalyst to produce a single product (e.g. ethanol) with one pass. Therefore, in order to increase the yield of ethanol and in accordance with one embodiment of the invention, it is necessary to separate the products (methanol) by distillation and re-introduce the methanol with the $H_2$ and CO at the compression stage. Several passes are required.

To gain a better understanding of the invention described herein, the following examples are set forth. It will be understood that these examples are intended to describe illustrative embodiments of the invention and are not intended to limit the scope of the invention in any way.

EXAMPLES

Example 1

The following defines characteristics of a homogenization chamber according to one embodiment of the invention.

In one embodiment, a homogenization chamber provides sufficient storage to allow for blending of the product gas so short-term variability in gas quality is substantially minimized, wherein the homogenization chamber is located outside where it will be exposed to snow, rain and wind load.

Functional Requirements

Input gas can be highly toxic and flammable and thus the following required safety features can be considered during the design of the homogenization chamber.

For example, the homogenization chamber is designed to meet following functional requirements.

| | |
|---|---|
| Normal/Maximum inlet temperature | 35 C./40 C. |
| Normal operating pressure | 3.0 psig |
| Normal/Maximum gas inlet flow rate | 7200 $Nm^3$/hr/9300 $Nm^3$/hr |
| Normal/Maximum gas outlet flow rate | 7200 $Nm^3$/hr/9300 $Nm^3$/hr |
| Relative humidity | 60%-100% |
| Storage volume of tank | 290 $m^3$ |
| Operating gas Volume (Range) | 0-290 $m^3$ |
| Mechanical design temperature | −40 C. to 300 C. |
| Mechanical design pressure | 5.0 psig |

For homogenization chamber design the following two conditions are to be considered:
(1) Maximum gas outlet flow with no inlet flow
(2) Maximum gas inlet flow with no outlet flow One embodiment of the gas composition to be stored is defined as follows:

| Gas Composition (v/v), Wet basis | |
|---|---|
| $CH_4$ | 0.03% |
| CO | 18.4% |
| $CO_2$ | 7.38% |
| $H_2$ | 20.59% |
| $H_2S$ | 354/666 ppm |
| H2O | 5.74% |
| HCl | 5 ppm/190 ppm |
| $N_2$ | 47.85% |

In one embodiment of the invention, the homogenization chamber is configured such that the following openings are provided.

One 36" Manhole (Shell)
One 36" Manhole (Roof)
One 18" Flange (for gas Inlet)
One 18" Flange (for gas outlet)
Four 1" flanged nozzles on the top of the homogenization chamber
Two 3" flanged nozzles on the top of the homogenization chamber
Two 4" flanged connections on the top of the homogenization chamber
Two 6" flanged connections on the top of the homogenization chamber
One 2" drain at the bottom of the homogenization chamber In one embodiment of the invention, the homogenization chamber is configured such that the following requirements are met.
1) Provision of all the required openings and manhole covers, blank flanges
2) Provision of all required supports for inspection and maintenance platform, access ladders for inspection.
3) Provision of required lifting hooks and grounding lugs for homogenization chamber.

In one embodiment of the invention, the homogenization chamber is designed in consideration of the following environmental conditions.

| | |
|---|---|
| Elevation above mean sea level | 80 m |
| Latitude | 45° 24' N |
| Longitude | 75° 40' W |
| Average atmospheric pressure | 14.5 psia |
| Maximum summer dry bulb temperature | 38° C. |
| Design summer dry bulb temperature | 35° C. |
| Design summer wet bulb temperature | 29.4° C. |
| Minimum winter dry bulb temperature | −36.11° C. |
| Mean wind velocity | 12.8 ft/sec |
| Maximum wind velocity | 123 ft/sec |

| | |
|---|---|
| Design wind velocity | 100 mph/160 kph |
| Prevailing wind direction | Mainly from south and west |
| Seismic Information | Zone 3 |

Material of Construction
  The material of construction is based on design conditions and gas composition.
Reliability and Maintainability
  Proper access for inspection and maintenance is provided. Homogenization chamber are highly reliable and all of the gaskets and flanges used are of appropriate standards to avoid any failure during operation.
Quality Assurance
  A quality system that ensures that products meet all requirements is followed.
  Each system generally is capable of operating in an industrial environment for many years, with very high reliability and availability. In one embodiment, the system is designed for reliability (including proper de-rating of all components), and that a comprehensive system of inspections and tests are conducted to ensure and demonstrate compliance with all elements of the specification, including interface requirements.
  A homogenization chamber will generally be traceable by serial number. Test data or a Certificate of Conformance, will typically be employed to ensure that the equipment meets all aspects of the Requirement Specification.
  All test and inspection data are maintained by unit serial number.

Example 2

The following defines characteristics of a homogenization chamber according to one embodiment of the invention.

In one embodiment of the invention, a homogenization chamber provides sufficient storage to allow for blending of the gas so that short-term variability in gas quality and pressure is minimized, wherein the homogenization chamber is located outside where it will be exposed to snow rain and wind load.

The homogenization chamber support structure interfaces with a concrete foundation. The homogenization chamber is free-standing and the dimensions of the homogenization chamber are designed to meet mechanical engineering requirements. The gas homogenization chamber typically comprises one single tank, which is erected on-site.

In one embodiment, some water condenses out of the gas, so a bottom drain nozzle is included in the design of the homogenization chamber for this purpose. To assist in draining the homogenization chamber, it is required that the homogenization chamber bottom not be flat, for example the homogenization chamber is configured having a conical bottom with a skirt. In one embodiment, traced/insulated drain piping is used to form the drain flange. The water within the homogenization chamber gravity drains to a floor drain, therefore the homogenization chamber is slightly elevated.

In one embodiment, the homogenization chamber is configured to meet the following functional requirements.

| | |
|---|---|
| Normal/Maximum Inlet Temperature | 35° C./40° C. |
| Normal/Maximum Operating Pressure | 1.2 psig/3.0 psig |
| Normal/Maximum Gas Inlet Flow Rate | 7000 Nm³/hr/8400 Nm³/hr |
| Normal/Maximum Gas Outlet Flow Rate | 7000 Nm³/hr/8400 Nm³/hr |
| Relative Humidity | 60%-100% |
| Storage Volume of Tank | 290 m³ |
| Mechanical Design Temperature | −40° C. to 50° C. |
| Mechanical Design Pressure | 5.0 psig |

In one embodiment, the material of construction of the homogenization chamber considers the gas composition given below, wherein corrosion is to be expected from the water due to the likely content of HCl, and $H_2S$.

| Gas Composition (v/v), Wet basis | |
|---|---|
| $N_2$ | 47.09% |
| $CO_2$ | 7.44% |
| $H_2S$ | 20 ppm |
| H2O | 3.43% |
| CO | 18.88% |
| $H_2$ | 21.13% |
| $CH_4$ | 0.03% |
| HCl | 5 ppm |

In one embodiment of the invention, the homogenization chamber is configured such that the following openings are provided.
  One 36" manhole near the bottom of the homogenization chamber
  One 6" flange at the top for relief
  One 16" flange on the shell for gas inlet
  One 16" flange on the shell for gas outlet
  Six 1" flanges on the shell (2 pressures, 1 temperature, 3 spares)
  One 2" flange at the bottom of the homogenization chamber (drain)
  One 1" flanges on the bottom cone for level switches In one embodiment of the invention, the homogenization chamber is configured such that the following requirements are met.
  1) Provision of all the required openings and manhole covers, and blind flanges for all spare nozzles.
  2) Provision of a ladder to the top of the homogenization chamber allowing safe access, for example with the integration of a railing, which can lead to the roof and relief valve.
  3) Provision of required lifting hooks and anchor bolts.
  4) Provision of a concrete ring wall.
  5) Provision of interior and exterior coatings of the homogenization chamber, if required.
  6) Provision of insulation and heat tracing of the bottom of the homogenization chamber.
  7) Provision of a concrete slab.

Figure 24:
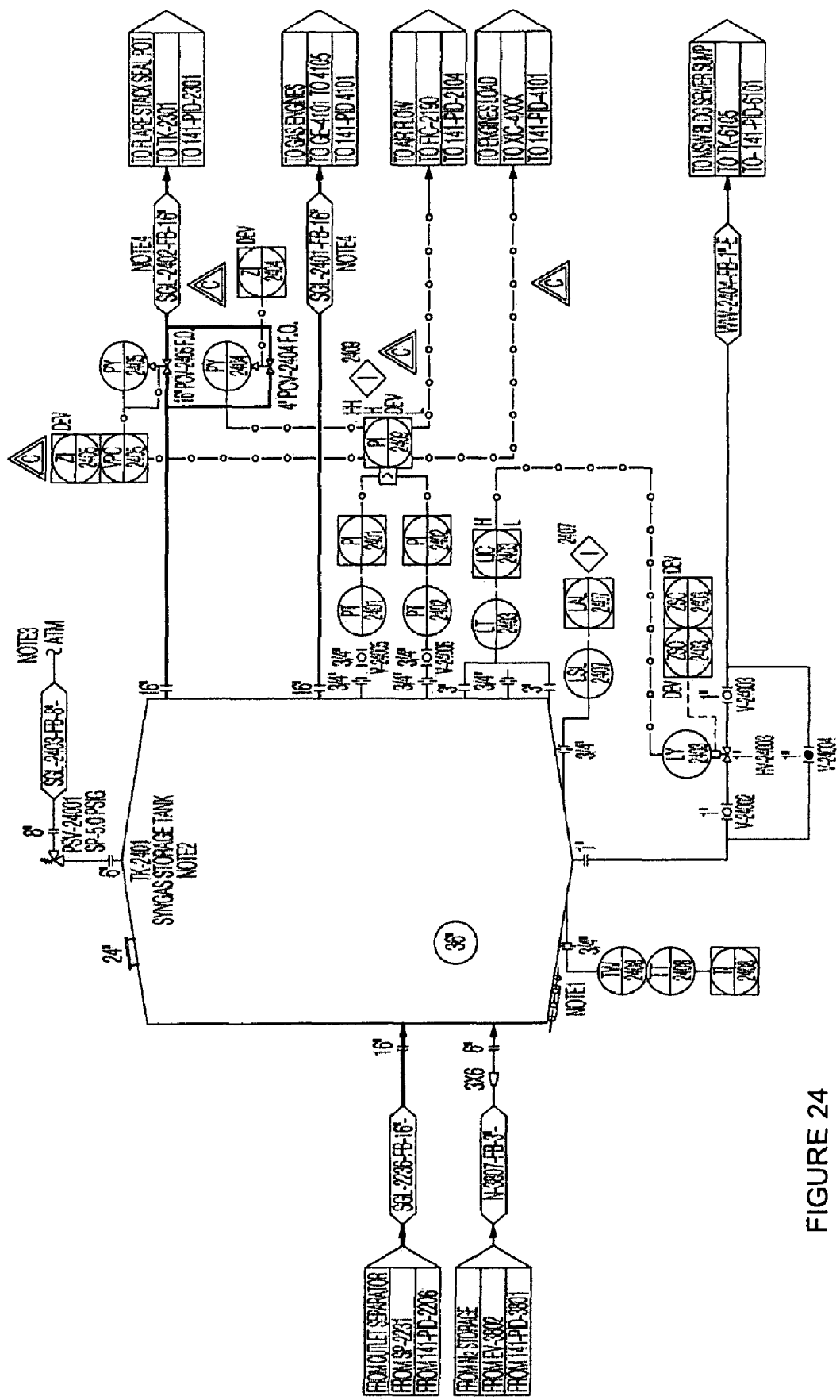
FIG. 24 is an illustration of a constant-volume homogenization chamber, in accordance with an embodiment of the invention.

In one embodiment of the invention, the homogenization chamber is configured according to the specifications defined at FIG. 24.

Materials and Construction
  The homogenization chamber is designed and constructed to operate in a harsh industrial (waste processing) environment. As mentioned above, the material of construction is based on the design conditions and the gas composition. Corrosion from water, HCl, $H_2S$ is considered during selection of materials of construction.

Example 3

The following provides functional requirements for a gas blower according to one embodiment of the invention.

In one embodiment, the gas blower includes a gas cooler and is to be used to withdraw gas from a plasma gasification system. The gas blower is configured to provide adequate suction through all the equipment and piping as per specifications described below.

Functional Requirements

Input gas is flammable and will create an explosive mixture with air, thus, in one embodiment of the invention all service fluid, i.e. seal purge, is done with Nitrogen. In one embodiment of the invention, the blower is operated through a variable speed drive (VSD) within the flow range of 10% to 100%.

Engineering of the system will be done with good engineering practice and following all applicable provincial and national codes, standards and OSHA guidelines. The blower is operated through a variable speed drive (VSD) within the flow range of 10% to 100%.

The gas blower is designed, for example, to meet following functional requirements.

| | |
|---|---|
| Normal gas inlet temperature | 35 C. |
| Normal gas suction pressure | −1.0 psig |
| Normal gas flow rate | 7200 Nm3/hr |
| Maximum gas flow rate | 9300 Nm3/hr |
| Maximum gas suction temperature | 40 C. |
| Normal discharge pressure | 3.0 psig |
| Normal discharge temperature (after gas cooler) | <35 C. |
| Mechanical design pressure | 5.0 psig |
| Relative Humidity of gas at blower inlet | 100% |
| Gas Molecular Weight | 23.3 |
| Cooling water supply temperature (product gas cooler) | 29.5 C. |
| Maximum acceptable gas discharge temperature (after product gas cooler) | 40 C. |
| Turn down ratio | 10% |

In one embodiment of the invention, the gas composition drawn through the system by the gas blower is defined as follows:

| Gas Composition, wet basis(v/v) | |
|---|---|
| $CH_4$ | 0.03% |
| CO | 18.4% |
| $CO_2$ | 7.38% |
| $H_2$ | 20.59% |
| Normal/Max $H_2S$ | 354/666 ppm |
| $H_2O$ | 5.74% |
| Normal/Max HCl | 5 ppm/100 ppm |
| $N_2$ | 47.85% |

To avoid an explosive mixture, in accordance with one embodiment of the invention, the blower is configured such that there is minimal to no air intake from the atmosphere. As the gas can be toxic and flammable, in accordance with one embodiment of the invention, the blower is configured such that there is minimal to no gas leak to the atmosphere. In one embodiment of the invention, the blower has a leak-free shaft seal. In one embodiment, an advanced leak detection system for leak in both directions is provided.

In one embodiment of the invention, the gas blower is configured such that the following requirements are met.
1. Provision of an explosion proof motor with leak-free blower shaft seal.
2. Provision of product gas cooler.
3. Provision of silencer with acoustic box to meet 80 dBA at 1 m noise regulation requirement.
4. Provision of a common base plate for the blower and motor.
5. Provision of an auxiliary oil pump with motor, and all required instrumentations for blower auxiliary system.
6. Provision of all instruments and controls (i.e. low and high oil pressure switch, high discharge pressure and temperature switch, differential temperature and pressure switch). In one embodiment, all switches shall be CSA approved discharge pressure gauge, discharge temperature gauge, oil pressure and temperature gauge. In one embodiment, all instruments shall be wired at common explosion proof junction box and VFD will be controlled by a pressure transmitter installed upstream of the blower.
7. Provision of zero leaks discharge check valve.
8. Provision of equipment safety system to prevent blower from excessive pressure/vacuum/shut off discharge (for example, systems like PRV and recycle line).

Technical Requirements

In one embodiment the blower satisfies the functional requirements of Section 2 and operate at about 600 Volts, 3 phase, 60 Hz.

Environmental

Product gas blower and product gas cooler may be located outside the building where it will be exposed to rain, snow and wind. Thus, in one embodiment, the gas blower is configured to withstand the following environmental conditions.

| | |
|---|---|
| Elevation above mean sea level | 80 m |
| Latitude | 45° 24' N |
| Longitude | 75° 40' W |
| Average atmospheric pressure | 14.5 psia |
| Maximum summer dry bulb temperature | 38° C. |
| Design summer dry bulb temperature | 35° C. |
| Design summer wet bulb temperature | 29.4° C. |
| Minimum winter dry bulb temperature | −36.11° C. |
| Mean wind velocity | 12.8 ft/sec |
| Maximum wind velocity | 123 ft/sec |
| Design wind velocity | 100 mph/160 kph |
| Prevailing wind direction | Mainly from south and west |
| Seismic Information | Zone 3 |

Class of Blower

In one embodiment, the blower is configured to work in an environment where explosive gases may be present in upset conditions. For example, all instruments and electrical devices installed on gas pipes or within about 2 meter distance will be classified for Class 1, zone 2.

Reliability, Maintainability and Spares

The blower shall be highly reliable. Proper access for inspection and maintenance is provided, as is access to isolate and correct faults.

The blower can be operated continuously (24/7). Frequent start/stop operation of the blower during process stabilization are contemplated. Gas blower is capable of working with high reliability even during frequent start/stop.

Quality Assurance

A quality system that ensures that products meet all requirements will be followed.

Each system is capable of operating in an industrial environment for many years, with very high reliability and availability. In one embodiment, the system is designed for reliability (including proper de-rating of all components), and that a comprehensive system of inspections and tests are conducted to ensure and demonstrate compliance with all elements of the specification, including interface requirements.

Materials and Construction

The material of construction is based on design conditions and gas composition. For example, electrical circuit boards, connectors and external components are coated or otherwise protected to minimize potential problems from dirt, moisture and chemicals. Control panels and switches are of robust construction, and are designed to be operated by personnel wearing work gloves.

Control Interfaces

Generally, variable speed drive for the motor control is employed. Motor over-voltage, overload protection etc is included.

Motor status, On/Off operation, speed change is operated and monitored remotely through DCS.

Example 4

Working Specification of a Gas Homogenization System

Gas Storage and Gas Heating

In one embodiment of the invention, the cleaned and cooled gas is stored in the gas storage tank. The purpose of the gas storage tank is to homogenize its composition (low heating value—LHV) and its pressure. The gas is heated on the exit of the gas storage prior to the engines to meet engine temperature requirements.

Composition—LHV

In one embodiment, the gas storage provides enough residence time for the gas to have better blending to avoid any short term heating value fluctuations. This is required because of the varied composition of the waste. With LHV fluctuations, the engine will run and produce the electricity, but it may deviate from its threshold emission limits because of poor combustion or poor fuel to air ratio.

In one embodiment, the volume of the tank is based on a hold up time of about 2 minutes. The 2 minute hold up time is designed to meet the gas engine guaranteed norms on LHV fluctuation specifications of about 1% LHV fluctuation/30 sec. The residence time up to the gas analyzer (upstream of the gas storage tank) is typically about 30 sec (including analysis and feedback). The maximum LHV fluctuation is typically about 10%. Thus, in one embodiment, to average this out and get 3% LHV fluctuation, 1.5 min storage is provided to meet the upper tolerable limit of the gas engine. Accordingly, the 2 min storage allows for some margin.

Pressure

In one embodiment, the storage tank is operated at 2.5 to 3.0 psig to meet gas engine fuel specification. The exiting gas pressure is maintained constant using a pressure control valve. In one embodiment, the gas tank has a design pressure of 5 psig, a relief valve is installed to handle unusual overpressure scenarios.

The 2 min hold up time described above also provides enough storage to reduce pressure fluctuations. In one embodiment, the allowable pressure fluctuation for the engine is 0.145 PSI/sec. In the case of a downstream failure of a gas engine, a buffer may be required (depending on control system response time and 30-35 sec gas resident time) to provide time to slow down the process or to flare the excess gas.

Volume Calculation

In one embodiment, cool gas flow entering the storage tank (26C), is at ~8400 Nm3/hr. That equates to 140 Nm3/min, for 2 min, that is 280 m3 of required storage volume.

Fixed Volume vs. Variable Volume

In one embodiment, a fixed volume tank is chosen over a variable volume tank because pressure fluctuations will not be quick in the process but the possibility of LHV fluctuation is there due to the nature of the waste. For example, a variable volume tank is typically more useful to absorb flow and pressure fluctuation. However if the tank is empty, it will not be helpful in compensating LHV fluctuation. The fixed volume on the other hand, is useful for averaging out LHV fluctuation. Also a fixed volume is typically more reliable than variable volume in terms of its construction and maintenance.

Example 5

Specifications for a Homogenization Chamber

The gas produced from the Plasma Gasification Process (From Plasma Gasification Converter) will be processed in the plant to remove unwanted impurities like acid gases, heavy metals and particulate matter. In one embodiment, the produced clean and dry gas will be utilised in gas engine for power generation. The gas from the converter will be neutralized and partially dehydrated prior to use in gas engines. This cleaned and dry gas will be stored in a Gas Homogenization Chamber for blending of the gas so that short-term variability in gas quality is minimized and constant gas flow is available for downstream applications such as a gas engine.

Engine

In one embodiment, the Gas inlet flow rate to the tank is 8200 Nm3/hr (4825 SCFM) at 35 C (7950 Am3/hr or 4675 ACFM at 1.0 PSIG). In one embodiment of the invention, the storage capacity of an homogenization chamber is equivalent to about 15 minutes of production rate.

Process Requirements

It is expected that fluctuations in gas flow and compositions is mainly due to change in material feed rate and composition, airflow fluctuations and temperature fluctuation inside the converter. Based on experimental data it is known that each torch cycle shall be of approximately 3 minutes. Optimizing cost of gas storage and impact of gas quality and flow fluctuations requires gas storage capacity of 3-5 torch cycles (i.e. 10-15 minute of production).

Considering 9000 m3/hr of maximum flow rate, storage tank maximum capacity is 2300 m3 while operating capacity shall be 0-2050 m3, in accordance with one embodiment of the invention.

Required gas pressure for gas engine is 2.2 psig, so it is necessary to maintain constant pressure of 1.5 psig (approx. 105 mbar) inside the gas storage, in accordance with one embodiment of the invention.

Typically, water drain system is provided inside the gas storage tank for wintertime water vapour condensation.

Process Basis of Design

In one embodiment, gas shall be stored at low pressure that will exclude storage system from pressure vessel standard.

Gas Compositions

In accordance with one embodiment of the invention, gas composition exiting Gas Conditioning System (GCS) is as follows:

| Gas compositions (Wet Basis) | |
|---|---|
| Gas Composition (Wet) | % |
| N2 | 50.414 |
| CO | 17.004 |
| H2 | 18.011 |
| CO2 | 8.809 |
| H2O | 5.734 |
| H2S | <20 ppm |

Gas Specifications
 Lower Flammability Limit: 17.93%
 Higher Flammability Limit: 73.26%

| Specification | Unit | Value |
|---|---|---|
| Gas Density | lb/ft3 | 0.0536 |
| Gas Molecular Weight | Kg/K Mole | 24.2 |
| Gas Viscosity | CP | 0.0253 |
| Gas Temperature | F | 95 |
| Gas Relative Humidity | % | 60 |
| Water Content | % | 3.3-5.7 |

In one embodiment of the invention, the following environmental conditions are considered.

| Environmental Data | | |
|---|---|---|
| Average Elevation above mean sea level | | 250 m |
| Average Atmospheric Pressure | | 14.5 psia |
| Maximum Summer Dry Bulb Temperature | | 100.4° F. |
| Design Summer Dry Bulb Temperature | | 95° F. |
| Design summer Wet Bulb Temperature | | 85° F. |
| Minimum Winter Dry Bulb Temperature | | −33° F. |
| Wind Data | Mean Velocity | 12.8 ft/s |
| | Maximum Velocity | 123 ft/s |
| | Design Velocity (to ANSI A58.1) | 145 ft/s |
| Prevailing Wind Direction - Mainly from South and West | Seismic design | TBD |

Storage Tank Location and Condition

In one embodiment, the Gas Storage shall be located outdoor, where it shall be exposed to rain, snow and sun with condensing environment.
 Design ambient temperature: −40 F
 Snow loading (Extreme snow depth): 150 cm
Alternatives:

In accordance with different embodiments of the invention, five alternatives storage technology selections are provided as follows.
 1) Compression of gas followed by storage in a pressure vessel;
 2) Storage of gas in traditional metal tank at low pressure;
 3) Storage of gas in a gas holder designed from membrane technology;
 4) No gas storage; and
 5) Storage of gas in dry seal gas holder.

Considerations for the use of the above storage technologies are provided below, but are not intended to limit the scope of the invention in any way.

1) Gas Compression and Storage

After closely reviewing this option, the operating cost of the compressor is very high. A gas engine requires gas at low pressure so if gas is compressed it needs to be decompressed before utilizing it for gas engines. Thus, it requires lots of operating cost to compress gas based on compression ratio.

2) Storage in Metal Tanks

Conventional metal storage is an expensive way to store gas at low pressure unless it is really required (mainly when it is compressed). Metal storage tanks are either fabricated in advance or fabricated on-site (Field erected) based on the size of the tank. Some applications require field erected storage tank because of large required capacity. It is very important to store gas properly to avoid any fire hazard. Metal storage tanks are made from various kinds of metals and metal alloys. Most common metal used is carbon steel because it is very cheap, easily available and has good strength. But for corrosive fluids various kind of metal alloys are used based on condition and type of the fluid to be stored.

Application of Metal Storage Tanks:
 (1) Liquid storage;
 (2) Storage of liquid or gas at high pressure; and
 (3) Small or medium capacity storage even high capacity storage for some applications, mainly liquid storage.

Typical Benefits of Storing Gas in a Metal Storage Tank:
 a) Better pressure control i.e. excessive pressure can be handled precisely and safely;
 b) Less Instrumentation required;
 c) Applicable for Full vacuum conditions if design for service;
 d) Better option for wide temperature range; and
 e) More reliable from safety point of view.

Disadvantages of Metal Storage at Low Pressure:
 a) Expensive due to large volume; and
 b) Pressure fluctuation during filling and emptying of the tank with large amount of gas.

There are some regulations for storing hydrocarbon that requires hydrocarbon gases to be stored in pressure vessel and metallic tanks.

3) Storage in Gas Holders (Double Membrane Technology)

Gas Holders are normally used to store natural gas and bio gas. Gas holders can typically store large volume of gas under very low pressure typically less than 14" WG (0.5 PSIG). This system includes two durable membranes. The outer membrane is cable restrained and remains inflated in a fixed position. An inner membrane moves freely as it stores or releases gas generated from the upstream of the storage or released in the down stream of the storage. An air handling system maintains a preset operating pressure between two membranes. This keeps outer membrane in fixed position regard less of inner membrane position. Operating pressure can be changed easily within design range.

While discharging gas from the gas holder a fan provides air to the air chamber (space between two membranes). As the gas is added to the holder, an adjustable pressure relief valve relieves the pressure between the two membranes allowing gas chamber to expand.

Applications of the Double Membrane Gas Holder:
 (1) Biogas intermediate storage; and
 (2) Methane sludge removal in anaerobic process.

Advantages of Double Membrane Gas Holder:
1) Reduced installation costs;
2) Easily handle sudden large amount of gas input or withdrawal of the same; and
3) No regular maintenance required such as painting.

Disadvantage of Gas Storage in a Gas Holder:
1) Not fit for high pressure application (Max 14" W.G-0.5 PSIG);
2) Not suitable for high temperature applications; and
3) Required more instrumentation and control for pressure control of the tank (required more relief valves).

4) No Gas Storage

It is important to know the motive of gas storage. For instance if storing gas that will lead gas engine feed composition and flow variation is not a consideration. It is important to evaluate how much composition variation will occur for an application, how fast a control system will react to those variations, how much composition and flow variation gas engine can tolerate.

From previous experimentation it was found that there can be significant gas composition variation in a process. The gas composition variation is greater than gas engine acceptance range, therefore, a homogenization chamber may be used.

Advantages of not Storing Gas:
1) No capital cost required; and
2) No instrumentation cost.

Disadvantages of not Storing Gas:
1) Unstable gas flow at gas engine;
2) Variable gas composition entering gas engine affecting gas engine performance; and
3) Can not isolate gasification process from gas engine and visa versa.

For some applications, it is recommended to have gas storage to avoid short-term variation in gas composition.

It is clear that dry seal type gas storage system can provide constant gas flow rate and pressure, besides this it is capable of satisfying required operating pressure, volume and temperature conditions.

5) Storage in Gas Holder (Dry Seal)

Dry seal type gas holders are typically a metallic cylinder outside with a central vent in the top. Inside the shell a diaphragm is connected to a metal piston to move diaphragm upward while filling the gas holder and moving down while withdrawing gas from the gas holder. Diaphragm is made up of various materials depending on type of gas to be stored.

Applications of the Dry Seal Holder:
1) Steel industries for intermediate gas storage; and
2) Mining and metallurgical industries to buffer the gas for power generation.

Advantages of the Dry Seal Holder:
1) Dry seal gas holders can handle very large volume of gas (up to 30000 m3);
2) Applicable for very large volume input and/or output;
3) Applicable for comparatively high pressure applications (Up to 2000 mm WG);
4) Low maintenance;
5) 15 to 20 years of service life;
6) No contaminated water removal before entry;
7) Applicable for wide range of temperatures; and
8) Requires lighter foundation.

Disadvantages of the Dry Seal Holder:
1) Not suitable for very high pressure application (above 2000 mm WC); and
2) More instrumentation required for operation.

Functional Description of a Dry Seal Homogenization Chamber in Accordance with One Embodiment of the Invention A Dry-seal gasholder is designed to have a gross (geometric) volume ranging from two hundred cubic meters up to one hundred and sixty-five thousand cubic meters, whilst having a working pressure range between fifteen and one hundred and fifty millibar.

The Dry-seal gasholder is finished with an anti-corrosive treatment to counteract local climatic conditions and also any chemical attack from the stored medium. This anti-corrosive treatment is fully compatible with the sealing membrane and also the environment.

The Dry Seal Gasholder has four major elements:
1. The foundation;
2. The main tank;
3. The piston; and
4. The sealing membrane.

Each of these elements can be divided into various sub-elements and associated accessories.

The Foundation

A concrete and hardcore base designed to withstand the weight of the steel gasholder structure constructed upon it and to withstand dynamic climatic conditions acting upon the gasholder etc.

The Main Tank

The main tank is designed to accommodate the design requirements laid down by the customer and climatic conditions.

There are three main sub-elements to the tank:

Tank Bottom

The tank bottom forms a gas tight seal against the foundation and is "coned up" to facilitate drainage to the periphery. The bottom is covered with steel plates. The outer annular plates are butt welded against backing strips, whilst the infill plates are lap welded on the top side only. Welded to the bottom infill plates Piston Support Structure When the piston is depressurized it rests on a steel framework, which is welded to the bottom plates.

Tank Shell

The shell of the tank is designed to accommodate the imposed loads and the general data supplied by the user. The shell is of butt-welded design and is gas tight for approximately 40% of its lower vertical height (known as the gas space) at which point the seal angle is located. The remaining upper 60% (known as the air space) of the shell has in it various apertures for access and ventilation.

Attached to the shell are various accessories:

Staircase Tower

For external access to the roof of the gasholder and also incorporates access to the inside of the gasholder via the shell access doors. A locked safety gate is usually located at the base of the staircase to prevent any unauthorized access to the gasholder.

Shell Access Doors

Doors located at pertinent points allowing access into the gasholder from the external staircase tower.

Shell Vents

Allow air to be displaced from the inside of the gasholder as the piston rises.

Inlet Nozzle

The connection nozzle allowing the stored gas to enter the gasholder from the supply gas main Outlet Nozzle For the export of the stored gas, this nozzle comes complete with an anti-vacuum grid to protect the sealing membrane during depressurization. Depending on the operational process the inlet & outlet nozzles maybe a shared connection Shell Drains Allow condensates within the gasholder gas space to drain away in seal pots.

The seal pots are designed to maintain the pressure with the gasholder

Shell Manways

Used for maintenance access into the gas space—only used whilst the gasholder is out of service.

Earthing Bosses

To ensure that the gasholder is safe during electrical storms etc

Volume Relief Pipes

Essential fail-safe system to protect the gasholder from over-pressurization once actuated, by the piston fender, the volume relief valves allow the stored gas to escape to atmosphere at a safe height above the gasholder roof. As the volume relief valves open they actuate a limit switch.

Volume Relief Limit Switches

Used to send signals to the control room to confirm the status of the volume relief valves Level Weight System A mechanical counter balance system to ensure that the pistons moments are kept in equilibrium. The level weights which run up and down tracks located on the gasholder shell also actuated limit switches to signal when the gasholder volume has reached pre-defined settings.

Level Weight Limit Switches

Used to send signals to the control room to operate import and export valves etc.

Contents Scale

On the gasholder shell is a painted scale displaying the volume of gas stored within the gasholder. An arrow painted on an adjacent level weight indicates the current status. Also painted on the scale is the location of the piston in relation to the shell access doors.

Seal Angle

Welded to the inside of the shell this angular section is where the sealing membrane attaches to the shell.

Tank Roof

The roof is designed to withstand the local climatic conditions and the possibilities of additional loads such as snow and dust. The roof of the gasholder is of thrust rafter radial construction and has a covering of single sided lap welded steel plates. The roof has various accessories attached including:

Center Vent

Allows air to enter and exit the gasholder as the storage volume changes.

Roof Vents

Small nozzle around the periphery used for the installation of the seal.

Roof Manways

Allows access down to the piston fender when the gasholder is full

Circumferential Hand Railing

Safety hand railing around the outside of the roof.

Radial Walkway

For access from the staircase to the center vent etc.

Volume Relief Valve Actuators

Mechanical arms that operate the volume relief valves once the piston fender reaches a certain level.

Level Weight Pulley Structures

Steel structures mounting the level weight rope pulleys and rope separators.

Load Cell Nozzles

For maintenance access to the load cell instrumentation used for volume recording purposes.

Radar Nozzles

For maintenance access to the radar instrumentation used for volume recording purposes and piston level readings.

Roof Interior Lighting Nozzles

For maintenance access to the gasholders interior lights.

Piston

The gasholder piston moves up and down the inside of the shell as gas enters and exits the gasholder. The weight of the piston (less the weight of the level weights) produces the pressure at which the gasholder will operate. The piston is designed to apply an equally distributed weight to ensure that the piston remains level at all times.

The piston made up of the following sub-elements:

Piston Deck

The outer annular area is formed from butt-welded steel plates resting on steel section rest blocks. Lap welded steel infill plates form a dome profile to withstand the gas pressure in the gas space beneath it. For higher-pressure gasholders the infill plates are lap welded on both sides, where as, low-pressure gasholders are only welded on the topside. The fully welded piston deck forms a gas tight surface, which rests on the piston support structure when the gasholder is depressurized.

The following ancillary items can be found on the piston deck:

Piston Manway

Used for maintenance access below the piston into the gas space—only used whilst the gasholder is out of service.

Load Cell Chain Receptacle

A receptacle for gathering up the load cell chains as the piston rises.

Piston Seal Angle

Welded to the outer topside of the annular plates, this angular section is where the sealing membrane attaches to the piston.

Level Weight Rope Anchors

Equally spaced around the periphery of the piston deck are the connections to which the level weight ropes are fixed.

Piston Fender

The fender is a steel frame structure that is fixed to the piston deck annular plates and acts as a support structure for the abutment plates. Access can be gained to the top of the piston fender from either the shell access doors or roof manways depending on the gasholder volume Attached to the piston fender are the following items:

Piston Walkway

A platform around the top of the piston fender equipped with safety hand railing—used for inspection purposes.

Piston Ladders

Rung ladders complete with safety loops for access to the piston deck from the piston walkway.

Radar Reflector Plates

Used to bounce the radar signal back to the radar instrument for volume indication recording and piston level readings Abutment Plates Fixed to the outside of the piston fender to form a circumferential surface for the sealing membrane to roll against whilst the piston moves during operation.

Piston Torsion Ring

Around the base of the piston fender is a torsion ring which helps keep the piston shape during pressurization. Concrete ballast can be added to the torsion ring to increase the weight of the piston and subsequently be a cost effective way to increase the pressure of the gasholder to the required level.

Sealing Membrane

The seal rolls from the shell to the abutment surface of the piston and vice versa providing the piston with a frictionless self-centering facility. During depressurization the seal also provides a gas tight facility that protects the holder from vacuum damage by blocking the gas outlet nozzle. During commissioning of the gasholder the sealing membrane is set into an operating condition. This setting must be carried out every time the gasholder is depressurized.

| Technical Specification | |
|---|---|
| Characteristics | |
| Working pressure | 103 mbar (±2 mbar) |
| Gross capacity | 2300 m3 |
| Working capacity | 2050 m3 (between 5% & 95% limits) |
| Shell height | 17185 mm |
| Inside shell diameter | 17000 mm |
| Piston stroke | 10200 mm |
| Net steel weight | 150 tones |
| Shell Plates | 6 & 8 mm thick butt welded |
| Seal angle Height | 5435 mm - fabricated from R.S. section Bottom |
| Annular row plates | 8 mm thick - butt-welded to backing strips |
| Infill plates | 6 mm thick - lap welded on sides only |
| Roof Structure Thrust | rafter type - fabricated from R.S. sections |
| Annular row plates | 5 mm thick - lap welded one side only |
| Infill plates | 4 mm thick - lap welded one side only |
| Piston Height | 5285 mm |
| Structure | Fabricated from R.S. sections Annular row plates 8 mm thick - butt-welded to backing supports |
| Infill deck plates | 6 mm thick - lap welded one Section |
| Support structure | Fabricated from R.S. sections |
| Abutment plates | 4 mm thick |
| External staircase | Fabricated from R.S. sections |
| Shell access doors | 3 no. - at various positions above belt angle |
| Roof periphery | handrail Fabricated from R.S. sections |
| Shell manways | 2 no. diametrically opposite 600 mm diameter |
| Piston manways | 1 no. - 600 mm diameter |
| Roof manways | 2 no. diametrically opposite 600 mm Diameter |
| Fittings | |
| Inlet nozzle | 1 no. - 450 mm diameter |
| Outlet nozzle | 1 no. - 450 mm diameter c\w anti-vacuum grid |
| Shell vents | 32 no. |
| Shell condensate drains | 6 no. - 50 mm diameter |
| Volume relief | 2 no. - 200 mm diameter |
| Roof vents | 8 no. - 150 mm diameter |
| Level weights 3 set each comprising of | 1 no. 5000 kg level weight 1 no. level weight guide 1 no. Guard 2 no. Level weight structures 2 no. 22 mm diameters plastic impregnated ropes 2 no. cable sheaves 4 no. jockey pulleys |
| Limit switches | 4 no. - level weight operated and set @ 5%, 10%, 90%, & 95% of piston stroke 1 no. - volume relief pipe operated |
| Load cells | 2 no. - c\w plastic chains |
| Earthing bosses | 4 no. |
| Contents scale | Vertical scale painted on side of shell |

Example 6

A Municipal Solid Waste Gasification Plant

This example provides a Municipal Solid Waste (MSW) plant, in accordance with one embodiment of the invention, including amongst others a gasification system, a gas conditioner and a gas homogenization system.

Process Overview

Figure 25:
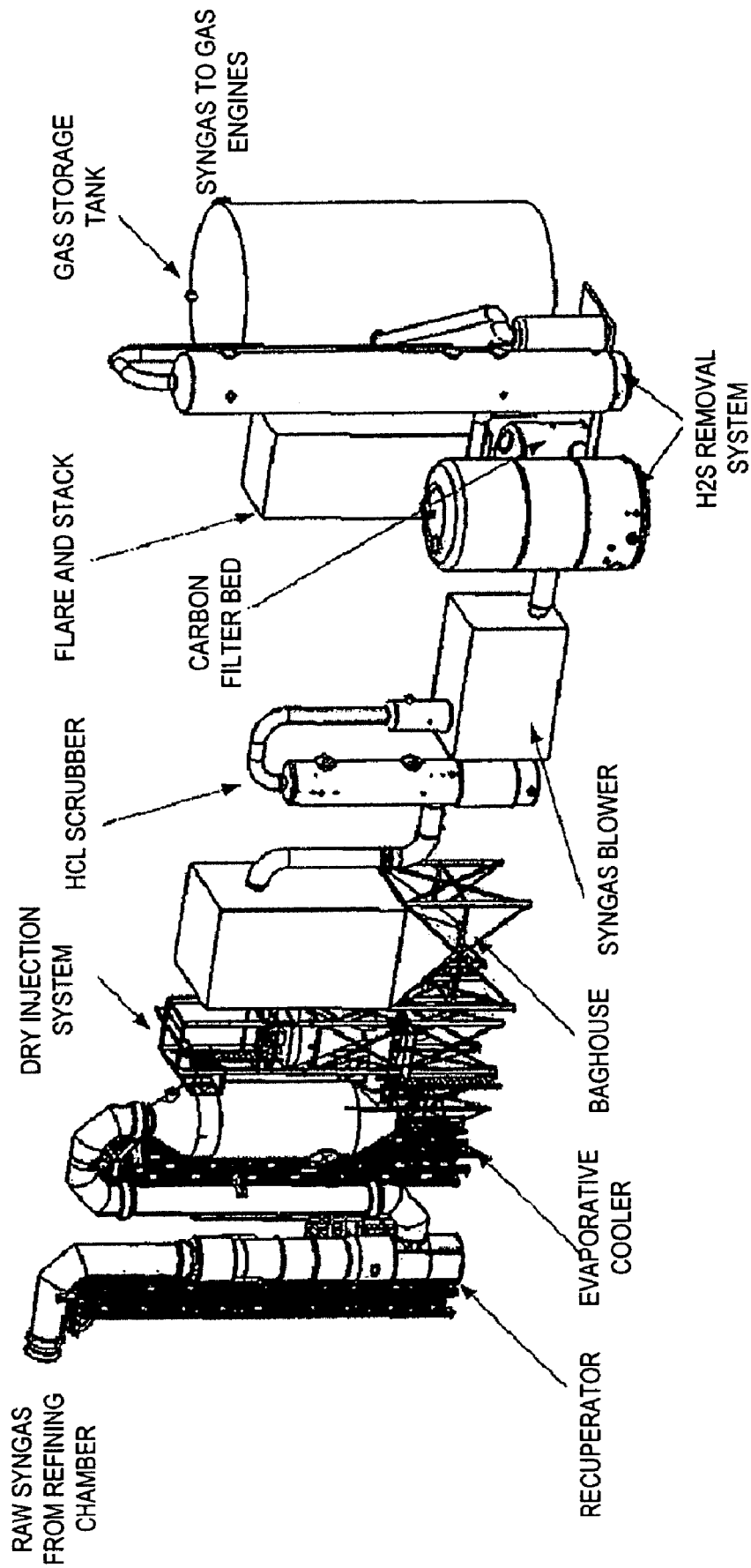
FIG. 25 is an illustration of a Gas Conditioning System (GCS) and a Gas Storage Tank according to one embodiment of the invention.
Figure 26:
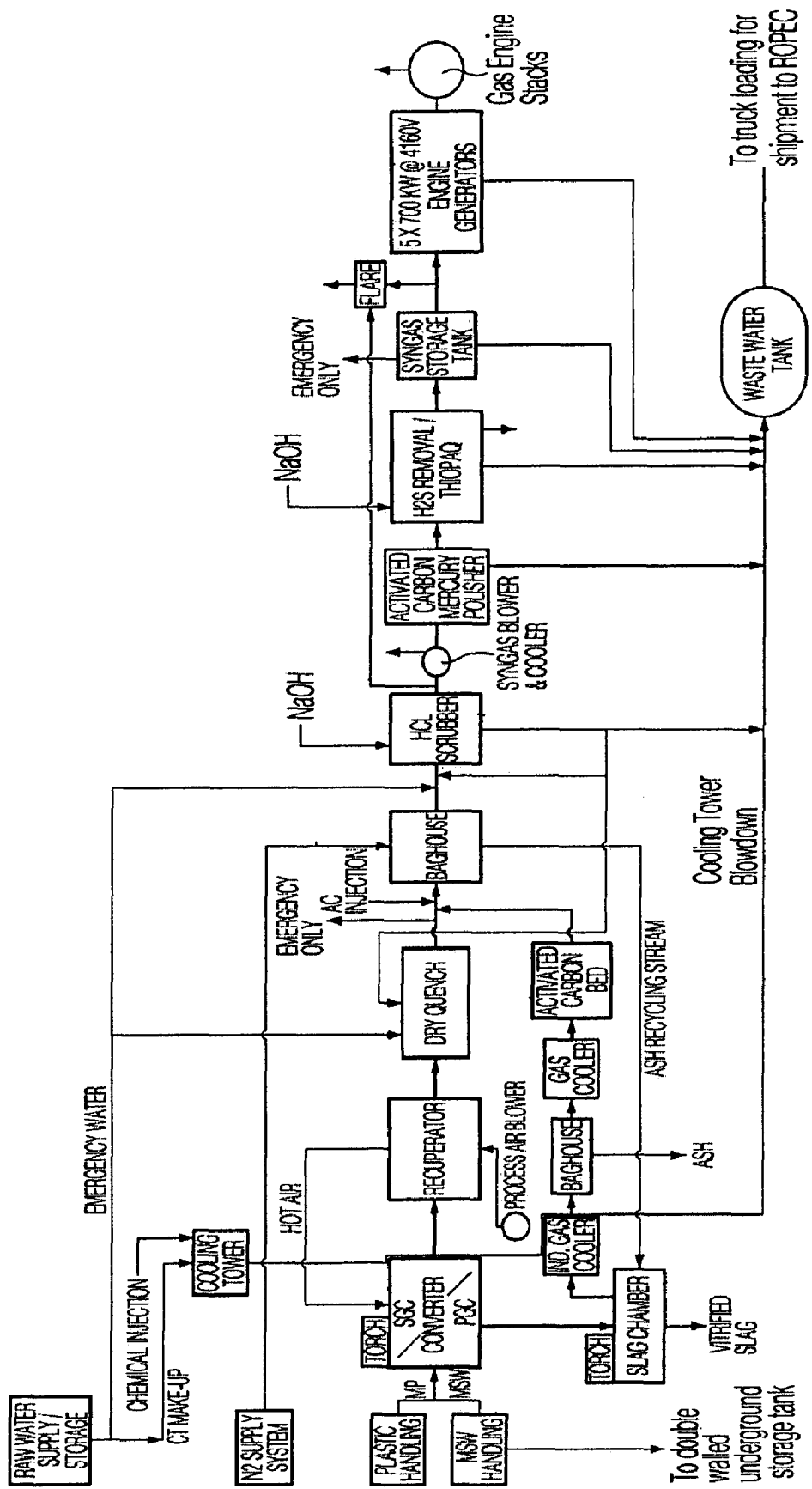
FIG. 26 is a flow diagram of a Municipal Solid Waste (MSW) Plasma Gasification Plant according to one embodiment of the invention.

The raw gas of the gasification system exits the converter and passes through a recuperator (heat exchanger). The recuperator cools the gas and the sensible heat is used to preheat the process air that will be introduced into the converter. The cooled gas then flows into a Gas Conditioning System (GCS), where the gas is further cooled and cleaned of particulates, metals and acid gases sequentially. The GCS in this embodiment comprises a converter gas conditioner and a solid residue gas conditioner. The cleaned and conditioned gas (with desired humidity) is stored in the gas homogenization chamber before being fed into gas engines, from which electricity is generated. The functions of major components (equipment) in the system are illustrated in the following sections (see Table 1), following the sequence that the gas is processed. The equipment figure and process diagram of the MSW gasification plant are presented in FIGS. 25 and 26.

TABLE 1

| Main Function of Subsystem | |
|---|---|
| Subsystem or equipment | Main Function |
| Recuperator | Cool down gas and recover sensible heat |
| Evaporative Cooler | Further cooling down of gas prior to baghouse |
| Dry Injection System | Heavy metal adsorption |
| Baghouse | Particle or dust collection |
| HCL Scrubber | HCL removal and gas cooling/conditioning |
| Carbon Filter Bed | Further mercury removal |
| $H_2S$ Removal System | $H_2S$ removal and elemental sulfur recovery |
| Solid residue gas conditioner | Slag chamber off-gas cleaning and cooling |
| Gas Homogenization System comprising Homogenization Chamber (Storage Tank), Chiller and Gas/Liquid Separator | Gas storage, homogenization, and humidity control |
| Gas Engines | Primary driver for electricity generation |
| Flare Stack | Burning gas during start-up/shut down/emergency |

Recuperator

In order to recover the gas sensible heat, the raw gas exiting from the reformer is cooled by air using a shell-tube type heat exchanger, called a recuperator. The gas flows through the tube side and the air passes through the shell side. The gas temperature is reduced from 1000° C. to 738° C. while increasing the air temperature from ambient to 600° C.

Evaporative Cooler (Stage One Processing)

This system drops Gas temperature to 250° C. via direct injection of water in a controlled manner (adiabatic saturation). This process is also called dry quench in that there is no liquid present in the cooling. The water is atomized and sprayed co-currently into gas stream. When the water is evaporated, it absorbs the sensible heat from gas and decreases the gas temperature to approximately 250° C. before it is fed to the baghouse.

Dry Injection System (Stage One Processing)

Activated carbon has a very high porosity, a characteristic that is conducive to the surface adsorption of large molecular species such as mercury and dioxin. Activated carbon, stored in a hopper, is pneumatically injected into the input gas stream and captured in the baghouse. In this way, the metals and other contaminants are separated from the gas stream. Alternatively other materials such as feldspar, lime, and other sorbents can be injected into the gas stream to control and capture heavy metals & tars found in the input gas stream without blocking it.

Baghouse (Stage One Processing)

Particulate matter and activated carbon with heavy metal on its surface is removed from the Gas in the bag-house. In the baghouse, a filter cake is formed with particulate matter. This filter cake enhances the particulate removal efficiency of the baghouse. Heavy metals like cadmium and lead are in particulate form at this temperature and are also collected in the baghouse with very high collection efficiency. When the pressure drop across the baghouse increases to a certain set limit, nitrogen pulse-jets will be used to clean the bags. The solids falling from the outside surface of the bags are collected in the bottom hopper and are sent to the solid residue conditioner for further conversion or disposal (see solid residue gas conditioner step below).

HCL Scrubber (Stage Two Processing)

The gas exiting from the baghouse (particulate free) is scrubbed in a packed tower to remove HCl in the gas stream by an alkaline solution. Inside the scrubber, it also provides enough contact area to cool down the gas to 35° C. The outlet HCl concentration will reach 5 ppm level. A waste water bleed stream is sent to a waste water storage tank for disposal.

Gas Blower (Stage Two Processing)

A gas blower is required at this point to provide the driving force for the gas throughout the process from the exit of the converter up to the engines. It is located upstream of the mercury polisher because the polisher has a better mercury removal efficiency under pressure. The blower is designed using all upstream vessel design pressure drops. It is also designed to provide the required pressure for downstream equipment pressure losses to have a final pressure of ~2.1 to 3.0 psig in the homogenization chamber.

Carbon Filter Bed (Stage Two Processing)

The gas pressure is boosted by a blower and further cooled by a water-cooled heat exchanger prior to the carbon bed filter which is used as a final polishing device for heavy metal in the gas stream. It is also capable of absorbing other organic contaminants, such as dioxins from the gas stream if present. The carbon bed filter is designed for over 99.0% mercury removal efficiency.

$H_2S$ Removal System (Stage Two Processing)

The Shell Paques Biological technology is selected for $H_2S$ removal. First, gas from the carbon bed filter passes through a scrubber where $H_2S$ is removed from gas by re-circulating an alkaline solution. Then, the sulfide containing solution from the scrubber is sent to the bioreactor for regeneration of alkalinity. The sulphur recovery occurs in the bio-reactor for oxidation of sulphide into elemental sulphur, followed by filtration of sulphur, sterilization of sulphur and bleed stream discharge to meet regulatory requirements. The $H_2S$ removal system is designed for 20 ppm $H_2S$ outlet concentration. Once the input gas exits the $H_2S$ removal system it is then directed to a gas homogenization system comprising amongst other components a chiller, a gas/liquid separator and homogenization chamber.

Solid Residue Gas Conditioner (Stage One Processing)

Ash (may contain activated carbon and metals) from the converter gas conditioner baghouse is purged periodically by nitrogen and conveyed to the solid residue conditioner, where the ash is vitrified. The gas coming out of the solid residue conditioner is directed through the solid residue gas conditioner baghouse to remove particulates and cooled by a heat exchanger before entering an activated carbon bed. The baghouse of the solid residue gas conditioner is also periodically purged based on pressure drop across the system. The solid residue collected in the solid residue gas conditioner baghouse is disposed by appropriate means. The combustible gas exiting from the solid residue gas conditioner (secondary gas stream) is sent back to the converter gas conditioner to fully utilize the recovered energy.

Gas Homogenization System

The gas engine design requires that the gas be of a specific composition range at a specified relative humidity. Therefore, once the cleaned gas exits the $H_2S$ scrubber, it is sub-cooled from 35° C. to 26° C. using a chiller. This will condense some water out of the gas stream. This water will be removed by a gas/liquid separator. This ensures that the gas has a relative humidity of 80% once reheated to 40° C. (engine requirement) after the gas storage prior to being sent to the engines in an embodiment where the output gas is used to power an engine. The cleaned and cooled gas enters a homogenization chamber (for example, a storage tank) designed to hold approximately 2 minutes of output from processing operations, thus blending any variations in "richness" of the gas, to achieve a highly consistent gas quality (a regulated gas) flowing to the engines. The homogenization chamber is operated at 2.2 to 3.0 psig to meet gas engine fuel specifications. Once the regulated gas exits the homogenization chamber, it is heated to the engine requirement and directed to the gas engines.

Gas Engines

Five GE Jenbacher gas engine sets are used to produce electricity based on the scale of the plant. Jenbacher gas engine is a type of reciprocating engine. It is capable of combusting low or medium heating value gas with high efficiency and low emissions. Each gas engine has 1.0 MW capacity. So, the full capacity of electricity generation is 5 MW. However, due to the relatively low gas heating value (as compared to fuels such as natural gas) the engines have been derated to operate around 700 kW at their most efficient operating point.

Flare Stack

An enclosed flare-stack will be used to burn gas during start-up, shut-down and process stabilization phases. Once the process has been stabilized the flare stack will be used for emergency purposes only. The flare stack should achieve 99.99% destruction efficiency.

Example 7

High Level Process Control of Municipal Solid Waste System Comprising a Gas Homogenization System This example provides a high level description of a control strategy for a Municipal Solid Waste (MSW) plant, according to one embodiment of the invention, which includes amongst others a gasification system, a gas conditioner and a gas homogenization system. The high level process control includes control of components of the gas homogenization system. A two phase approach is used with regard to development and implementation of the process control strategy for an MSW plasma gasification plant:

Phase 1: Operation During Start-Up and Commissioning

For start-up and commissioning, a simple front-to-back (or supply-driven) control strategy is used where the converter is run at a fixed feed rate of MSW and process variations are absorbed by the downstream equipment (engines/generators & flare). The plant is operated with a small buffer of excess gas production, requiring a small continuous flare. Gas production beyond this normal amount increases the amount flared and deficient gas production first eats into this buffer, but may eventually require generator power output to be reduced (generators can be operated from 50-100% power output via an adjustable power set point).

The benefits of this control scheme are:

It is less complex. It improves the ability to start-up and commission the plant, and then to make use of the operating data to implement more sophisticated control. It decouples the back-end from the front-end such that problems with one section of the plant are less likely to cascade to the rest of the plant. This increases the uptime and improves the ability to troubleshoot and optimize each part of the process. The small continuous flare eliminates the risk of large visible flame at the flare stack which can occur if the flare is operated in stop/start mode.

Phase 2: Long-Term Operating Strategy

The long-term control strategy for the MSW plant is to achieve back-to-front control (or demand-driven control) where the gas engines/generators at the back-end of the system drive the process. The gas engines consume a certain volume/hr of fuel depending on the energy content of the fuel gas and the electrical power being generated. Therefore the high level goal of the control system is to ensure that adequate MSW/HCF feed enters the system and is converted to gas of adequate energy content to run the generators at full power at all times, while precisely matching gas production to gas consumption such that flaring of gas is eliminated and the electrical power produced per ton of MSW consumed is optimized.

A high-level process control schematic for Phase 2 operation is shown in FIG. 15. Phase 1 operation is a sub-set of the control schematic shown.

Phase 1

Main Process Control Goals a) Stabilize the pressure in the gas homogenization chamber (for example, a storage tank).
b) Stabilize the composition of the gas being generated.
c) Control pile height of material in the converter lower chamber.
d) Stabilize temperatures in the converter lower chamber.
e) Control temperatures in the reformer.
f) Control converter process pressure.

Description of Goals a) Stabilize the Pressure in the Gas Homogenization Chamber.

Typically, gas engines are rather intolerant of changes in supply pressure. The specifications for Jenbacher engines are as follows:
   minimum pressure about 150 mbar (2.18 psig)
   maximum pressure about 200 mbar (2.90 psig)
   allowed fluctuation of fuel gas pressure=+/−10% (+/−17.5 mbar, +/−0.25 psi)
   maximum rate of gas pressure fluctuation=about 10 mbar/sec (0.145 psi/sec)

The engines have an inlet regulator that can handle small disturbances in supply pressure, and the holdup in the piping and gas homogenization chamber act somewhat to deaden these changes, but this remains by necessity the fastest acting control loop on the converter.

The initial Phase 1 pressure control strategy will be based on the operating premise that the converter will be run at sufficient MSW feed rate to generate a small buffer of excess gas production, which will be flared continuously. Therefore the gas homogenization chamber pressure control becomes a simple pressure control loop where the pressure control valves in the line from gas homogenization chamber to the flare are modulated as required to keep homogenization chamber pressure at the desired set point.

b) Stabilize the Composition of the Gas being Generated.

The gas engines can operate over a wide range of fuel values, provided that the rate of change is not excessive. In one embodiment, the allowable rate of change for LHV is <1% fluctuations in gas LHV/30 sec. For $H_2$ based fuels, the fuel gas is adequate with as little as 15% $H_2$ by itself, and the LHV can be as low as about 50 btu/scf (1.86 MJ/nm3). In one embodiment, the LHV for the gas was in the 4.0-4.5 MJ/nm3 range. The system volume and gas homogenization chamber greatly simplify the task of stabilizing the rate of change by providing mixing of about 2 minutes worth of gas production.

In one embodiment, the gas composition is measured by a gas analyzer installed in the inlet of the gas homogenization chamber. Based on this measurement the controller will adjust the fuel-to-air ratio (i.e. slightly increase/decrease MSW feed rate) in order to stabilize the gas fuel value. Increasing either the MSW or HCF feed relative to the air addition increases the fuel value of the gas. Since this control action has a fairly long response time, it will be tuned to only prevent long-term drift, not to respond to short-term variation.

While the HCF is by itself a much richer (~2×LHV) fuel source, it is typically being added in a 1:20 ratio with the MSW, and is not therefore the dominant player in terms of fuel being added to the system. It is uneconomical to add too much HCF to the system. HCF therefore is used as a trim and not as a primary control. HCF is ratioed to the total feed with the ratio adjusted to stabilize the total C exiting the system in the gas, as measured by the gas analyzer. This dampens fluctuations in MSW fuel value.

c) Maintain a Stable Inventory of Material in the Converter

A level control system is required to maintain stable pile height inside the converter. Stable level control is needed to prevent fluidization of the material from process air injection which could occur at low level and to prevent poor temperature distribution through the pile owing to restricted airflow that would occur at high level. Maintaining stable level also maintains consistent converter residence time.

A series of level switches in the primary gasifier measure pile depth. The level switches are microwave devices with a emitter on one side of the converter and a receiver on the other side, which detect either presence or absence of solid material at that point inside the converter.

The inventory in the converter is a function of feed rate and ram motion (and to a lesser degree conversion efficiency. Stage 3 ram sets converter throughput by moving at a fixed stroke length and frequency to discharge ash from the converter. Stage 2 ram follows and moves as far as necessary to push material onto Stage 3 and change the Stage 3 start-of-stage level switch state to "full". Stage 1 ram follows and moves as far as necessary to push material onto Stage 2 and change the Stage 2 start-of-stage level switch state to "full". All rams are then withdrawn simultaneously, and a scheduled delay is executed before the entire sequence is repeated. Additional configuration may be used to limit the change in consecutive stroke lengths to less than that called for by the level switches to avoid excess ram-induced disturbances.

The rams need to be moved fairly frequently in order to prevent over-temperature conditions at the bottom of the converter. In addition, full extension ram strokes to the end of each stage may need to be programmed to occur occasionally to prevent stagnant material from building up and agglomerating near the end of the stage.

d) Stabilize Temperatures in the Converter Lower Chamber

In order to get the best possible conversion efficiency, the material is kept at as high a temperature as possible, for as long as possible. However, temperatures cannot go too high or the material will begin to melt and agglomerate (form clinkers), which: 1) reduces the available surface area and hence the conversion efficiency, 2) causes the airflow in the pile to divert around the chunks of agglomeration, aggravating the temperature issues and accelerating the formation of agglomeration, 3) interferes with the normal operation of the rams, and 4) potentially causes a system shut down due to jamming of the ash removal screw.

The temperature distribution through the pile will also be controlled to prevent a second kind of agglomeration from forming—in this case, plastic melts and acts as a binder for the rest of the material.

Temperature control within the pile is achieved by changing the flow of process air into a given stage (i.e. more or less combustion). The process air flow provided to each stage in the bottom chamber will be adjusted to stabilize temperatures in each stage. Temperature control utilizing extra ram strokes may also be necessary to break up hot spots.

e) Control Temperatures in the Reformer

Plasma torch power is adjusted to stabilize the reformer exit temperatures at the design set point (about 1000° C.). This ensures that the tars and soot formed in the primary gasifier are fully decomposed. Addition of process air into the reformer also bears part of the heat load by releasing heat energy with combustion of gas. The flow rate of process air is adjusted to keep torch power in a good operating range.

f) Control Converter Process Pressure

Converter pressure is stabilized by adjusting the gas blower's speed. At speeds below the blower's minimum operating frequency, a secondary control overrides and adjusts the recirculation valve instead. Once the recirculation valve returns to fully closed, the primary control re-engages.

Phase 2

For Phase 2 operation, all of the process control goals listed above are maintained. However the key new requirements are to eliminate flaring of gas and to optimize the amount of electrical power produced per ton of MSW consumed. This requires that the flow of gas being produced must exactly match the fuel being consumed by the engines. Therefore, back-to-front control (or demand-driven control) must be implemented where the gas engines/generators at the back-end of the system drive the process.

In order to stabilize gas flow out of the converter, process airflow into the converter is increased. Adjusting the rate of MSW or HCF addition to the system eventually changes the gas flow, but with about a 45+ minute residence time and no significant gasification reactions taking place at the point of material entry, there is no chance of a fast response due to these adjustments (it is expected that significant response may take about 15 minutes). Adjusting total airflow provides the fastest possible acting loop to control pressure. In the short term, because of the large inventory of material in the converter, adding more air to the bottom chamber does not necessarily dilute the gas proportionately. The additional air penetrates further into the pile, and reacts with material higher up. Conversely, adding less air will immediately enrich the gas, but eventually causes temperatures to drop and reaction rates/gas flow to decrease.

Total airflow is ratioed to material feed rate (MSW+HCF), so the means of increasing air flow is to boost material feed rate. Controller tuning is set such that the effect of increased air is seen immediately. Controller tuning for feed rate is slower, but the additional feed eventually kicks in and provides the longer term solution to stabilizing gas flow. In one embodiment, temporarily reducing generator power output is required depending on system dynamics to bridge the dead time between increasing the MSW/HCF feed rate and seeing increased gas flow.

We claim:

1. A gas homogenization system for regulating gas characteristics of a gas from a gasification facility, comprising:
    a) one or more gas homogenization chambers, each configured to homogenize a gas from a gasification facility that is substantially free of non gaseous substances, comprising one or more gas inlets and one or more gas outlets;
    b) one or more sensing elements associated with each gas homogenization chamber for monitoring one or more gas characteristics;
    c) one or more response elements associated with each gas homogenization chamber for affecting a change to the one or more gas characteristics; and
    d) one or more process devices operatively connected to the one or more response elements for adjusting the one or more characteristics of the gas to meet requirements of one or more gas engines or one or more gas turbines;
wherein the homogenization chamber is designed to accommodate a residence time sufficient to enable monitoring and regulation of the one or more gas characteristics.

2. The system according to claim 1 further comprising one or more draft induction devices for providing uniform input gas flow to the gas homogenization chambers.

3. The system according to claim 1 further comprising one or more chillers for adjusting the temperature of the gas upstream of the gas homogenization chambers.

4. The system according to claim 1 further comprising one or more gas/liquid separators for adjusting the humidity of the gas upstream of the gas homogenization chambers.

5. The system according to claim 1 further comprising one or more gas conditioning skids for adjusting the temperature and humidity of the gas downstream of the gas homogenization chambers.

6. The system according to claim 1 further comprising one or more filters for removing impurities from the gas downstream of the gas homogenization chambers.

7. The system according to claim 1, each gas homogenization chamber further comprising one or more emergency exit ports.

8. A process for converting an input gas from a gasification process to an output gas suitable for a turbine or gas engine, the process comprising the steps of:
    a) providing an input gas from a gasification process that is substantially free of non-gaseous substances to one or more gas homogenization chambers;
    b) monitoring the gas for at least one of chemical composition, temperature, flow rate, and pressure; and
    c) providing instructions for adjusting the at least one of chemical composition, temperature, flow rate, and/or pressure parameters of the gas thereby producing a regulated an output gas that satisfies the requirements of the turbine or gas engine.

9. The gas homogenization system of claim 1 operatively associated with a control system comprising:

one or more sensing elements configured to sense one or more characteristics of a process, a process device, a process input and/or process output;

one or more response elements configured to affect one or more characteristics of one or more processes within the gas homogenization system; and one or more computing platforms operatively associated with one or more of the sensing elements and one or more of the response elements, the one or more computing platforms configured to receive input signals from at least one sensing element and to provide control signals to at least one response element to either maintain or adjust a process characteristic within the gas homogenization system, wherein the control system is configured to utilize feed-forward control or feed-back control or predictive control or adaptive control or a combination thereof.

* * * * *